United States Patent
Haebel et al.

(10) Patent No.: US 12,054,525 B2
(45) Date of Patent: Aug. 6, 2024

(54) NPY2 RECEPTOR AGONISTS

(71) Applicant: Boehringer Ingelheim International GmbH, Ingelheim am Rhein (DE)

(72) Inventors: Peter Wilhelm Haebel, Mittelbiberach (DE); Albert Brennauer, Biberach (DE); Charlotte Stahl Madsen, Malov (DK); Soren Ljungberg Pedersen, Borup (DK); Stefan Peters, Biberach an der Riss (DE)

(73) Assignee: Boehringer Ingelheim Internatioal GmbH, Ingelheim am Rhein (DE)

( * ) Notice: Subject to any disclaimer, the term of this patent is extended or adjusted under 35 U.S.C. 154(b) by 0 days.

(21) Appl. No.: 18/068,641

(22) Filed: Dec. 20, 2022

(65) Prior Publication Data

US 2023/0340039 A1 Oct. 26, 2023

Related U.S. Application Data

(63) Continuation of application No. 17/093,680, filed on Nov. 10, 2020, now abandoned.

(30) Foreign Application Priority Data

Nov. 11, 2019 (EP) ..................... 19208394

(51) Int. Cl.
C07K 14/47 (2006.01)
A61K 38/00 (2006.01)

(52) U.S. Cl.
CPC .............. *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2007/0135351 A1 | 6/2007 | Conde-Knape et al. | |
| 2015/0152150 A1 | 6/2015 | Oestergaard et al. | |
| 2019/0002520 A1 | 1/2019 | Oh et al. | |
| 2020/0014514 A1 | 1/2020 | Gao et al. | |
| 2020/0140514 A1* | 5/2020 | Briere | A61K 47/542 |

FOREIGN PATENT DOCUMENTS

| | | | |
|---|---|---|---|
| WO | 2005089789 A2 | 9/2005 | |
| WO | 2005077072 | 11/2005 | |
| WO | 2006066024 | 6/2006 | |
| WO | 2008152403 | 6/2008 | |
| WO | 2008101017 | 8/2008 | |
| WO | 2009064298 | 5/2009 | |
| WO | 2010007251 | 6/2010 | |
| WO | 2010070251 A1 | 6/2010 | |
| WO | 2010070252 | 6/2010 | |
| WO | 2010070253 | 6/2010 | |
| WO | 2010070255 | 6/2010 | |
| WO | 2011058165 | 11/2010 | |
| WO | 2011006497 | 1/2011 | |
| WO | 2011033068 | 3/2011 | |
| WO | 2011160630 | 12/2011 | |
| WO | 2011160633 | 12/2011 | |
| WO | 2012168430 | 12/2012 | |
| WO | 2012168431 A2 | 12/2012 | |
| WO | 2012168432 | 12/2012 | |
| WO | 2013092703 | 6/2013 | |
| WO | 2013164483 | 11/2013 | |
| WO | 2014041195 | 3/2014 | |
| WO | 2015067716 | 5/2014 | |
| WO | 2014178018 | 11/2014 | |
| WO | 2015040182 | 3/2015 | |
| WO | 2015055801 | 4/2015 | |
| WO | 2015055802 | 4/2015 | |
| WO | 2015071229 | 5/2015 | |
| WO | 2015071355 | 5/2015 | |
| WO | 2016198682 | 6/2016 | |
| WO | 2016146739 | 9/2016 | |
| WO | 2016166289 | 10/2016 | |
| WO | 2016198624 | 12/2016 | |
| WO | 2017116204 | 12/2016 | |
| WO | WO-2016198682 A1 * | 12/2016 | ............ A61K 38/00 |
| WO | 2017116205 | 7/2017 | |
| WO | 2017192538 A1 | 11/2017 | |
| WO | 2018046719 | 3/2018 | |
| WO | 2018081370 | 5/2018 | |
| WO | 2018081375 A1 | 5/2018 | |
| WO | 2018100134 | 6/2018 | |
| WO | 2018100135 | 6/2018 | |
| WO | 2018172390 A1 | 9/2018 | |
| WO | 2018224630 A1 | 12/2018 | |
| WO | 2019110982 A1 | 6/2019 | |

(Continued)

OTHER PUBLICATIONS

Ahn et al. (Peptides for Youth: The Proceedings of the 20th American Peptide Symposium, 515, DOI: 10.1007/978-0-387-73657-0_224) (Year: 2009).*

Ahn, John S. et al. "Synthesis and Biological Evaluation of PYY(3-36) Analogs Substituted with Alanine" (2009), Advances in Experimental Medicine and Biology, vol. 611, 515-516.

Bak, Annette et al. "Physicochemical and Formulaton Developability Assessment for Therapeutic Peptide Delivery—A Primer" (2015) The AAPS Journal, vol. 17, No. 1, 144-155.

Batterham, Rachel L. et la. Inhibition of Food Intake in Obese Subjects by Peptide YY3-36, (2003) The New England Journal of Medicine, vol. 349, 10, 941-948.

Beck-Sickinger, Annette G. et al. "Complete L-alanine scan of neuropeptide Y reveals ligands binding to Y1 and Y2 receptors with distinguished conformations" (1994), Eur. J. Biochem, vol. 225, 947-958.

Berge, Stephen, M et al. "Pharmaceutical Salts" (1977) Journal of Pharmaceutical Sciences, vol. 66, No. 1, 1-19.

(Continued)

*Primary Examiner* — Sergio Coffa
(74) *Attorney, Agent, or Firm* — Mary Breen Smith

(57) ABSTRACT

The invention relates to PYY analogues having alanine at position 4, lysine at position 7, QRY as the C-terminal end and a half-life extending group. The analogues of the invention are soluble around pH 6 and 7. The invention also relates to pharmaceutical compositions comprising such PYY analogues, and to the medical use of the analogues.

12 Claims, No Drawings

Specification includes a Sequence Listing.

(56) References Cited

FOREIGN PATENT DOCUMENTS

| WO | 2020092191 | | 5/2020 |
|---|---|---|---|
| WO | 2021094259 | A1 | 5/2021 |

OTHER PUBLICATIONS

Bujak, Emil et al. "Reformatting of scFv Antibodies into the scFv-Fc Format and their Downstream Purification", Chapter 20, Monoclonal Antibodies: Methods and Protocols, (2014) vol. 1131, 315-334.
Corrigan, Owen I. "Salt Forms: Pharmaceutical Aspects" (2007) Encyclopedia of Pharmaceutical Technology, 3177-3186.
Fields, Gregg B. et al. "Principles and Practice of Solid-Phase Peptide Synthesis" (2002) Synthetic Peptides, A User's Guide, Second Edition, 93-219.
Gershoni, Jonathan et al. "Epitope Mapping, The First Step in Developing Epitope-Based Vaccines" (2007) Drug Development, vol. 21, 145-156.
Henry, Kelly et al, "Vitamin B12 Conjugation of Peptide YY3-36 Decreases Food Intake, Compared to native Peptide-YY3-36 Upon Subcutaneous Administration in Male Rats" (2015) Endocrinology, vol. 156, 1739-1749.
International Search Report for PCT/EP2020/081513 mailed Nov. 9, 2020.
Koglin, Norman et al. "Novel modified and radiolabeled neuropeptide Y analogues to study Y-receptor subtypes" (2004) Neuropeptides, vol. 38, No. 4. 153-161.
Merkouris, et al. "Supplemental Appendix, Function-Based Selection of TrB Activating Antibodies: Characterization of a Full BDNK Agonist Antibody on Human Neurons", PNAS, Published Jul. 9, 2018, 10 pgs.
Merkouris, Spyros et al., "Fully Human agonist antibodies to TrkB using autocrine cell-based selection from a combinatorial antibody library", (2018) PNAS, vol. 115, No. 30, E7023-E7032.
Roux, Stephane et al. "Elimination and exchange of trifluroacetate counter-ion from cationic peptides: a crtical evaluation of different approaches" (2008), Journal Peptide Science, vol. 14, 354-359.
Wang, Shudan et al. "Therapeutic Potential of a TrkB agonistic antibody for Alzheimer's Disease" (2020) Thernostics, vol. 10, Issue 15, 6854-6874.
European Search Report for EP20189966.3 mailed Feb. 19, 2021, 7 pgs.

* cited by examiner

NPY2 RECEPTOR AGONISTS

SEQUENCE LISTING

The instant application contains a Sequence Listing which has been submitted electronically in XML format and is hereby incorporated by reference in its entirety. Said XML copy, created on Apr. 14, 2023, is named 01-3375-US-2.xml and is 677 kilobytes in size.

FIELD OF THE INVENTION

The present invention relates to PYY analogues that are neuropeptide Y2 (NPY2) receptor agonists, and to their medical use in the treatment and/or prevention of a variety of diseases, conditions or disorders, such as treatment and/or prevention of excess food intake, excess body weight, obesity, metabolic diseases, and other conditions or disorders related to excess body weight or obesity, e.g. diabetes and cardiovascular diseases.

BACKGROUND OF THE INVENTION

Overweight and obesity are defined as abnormal or excessive fat accumulation that presents a risk to health. In this regard, overweight and obesity are major risk factors for a number of chronic diseases, including type 2 diabetes, cardiovascular diseases and cancer. According to the WHO overweight and obesity are no longer considered a problem limited to high income countries but are now dramatically on the rise in low- and middle-income countries. WHO's Global Health Observatory indicate that, in 2016, 39% of women or men aged 18 and over were overweight and 11% of men and 15% of women were obese. Despite long-standing efforts, the number of overweight and obese patients is still growing.

First line therapy for overweight and obese patients comprise diet and exercise but often are not sufficiently efficacious. Second line treatment options are bariatric surgery and pharmacotherapy. Available pharmacological treatments seem to lack in efficacy and/or safety, and only a limited number of approved therapies are available in the US and in Europe.

Therefore, there is still a high medical need for more efficacious and safe treatment options.

NPY (Neuropeptide Y; SEQ ID No:1—human sequence), PYY (Peptide YY; SEQ ID No: 2—human sequence), and PP (Pancreatic Polypeptide; SEQ ID No:3—human sequence) are naturally secreted homologous, 36 amino acid, C-terminally amidated peptides and belong to the PP-fold family of peptides.

Sequence of hPYY (3-36):

Ile Lys Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg Tyr (SEQ ID No:4)

PYY is cleaved to PYY(3-36) by dipeptidyl peptidase IV (DPP IV). PYY(3-36) displays increased selectivity for the neuropeptide Y2 receptor over neuropeptide Y1, Y4 and Y5 receptors as compared to PYY(1-36), albeit some Y1 and Y5 affinity is retained. It is believed that PYY or PYY(3-36) exhibits the feeding suppressive action via activation of the neuropeptide Y2 receptor (*Inhibition of Food Intake in Obese Subjects by Peptide YY$_{3-36}$*, N Engl J Med 2003; 349; 941-8).

However, PYY and also PYY(3-36) have a short half-life in the body and show undesirable chemical or physical properties, e.g. low stability. Further, the pharmacologic effect, e.g. its efficacy as body weight lowering agent, seems limited.

WO2014/178018 discloses PYY analogues and their ability to reduce food intake in mice. WO2011/033068 and WO2011/058165 disclose long acting Y2 receptor agonists. WO2015/071355, WO2016/198682 and WO2020/092191 relate to PYY compounds, which are selective Y2 receptor agonists. PYY compounds are disclosed comprising a covalently attached substituent or modifying group also referred therein as a protracting moiety.

There is a need in the art for further (long acting) PYY analogues selectively acting on the NPY2 receptor. For example, it would be desirable to increase further the solubility of PYY analogues, preferably to increase the solubility around pH 7 and/or around pH 6. This would increase the formulation options for a ready-to-use application and potentially allow combinations with other (peptide) therapeutics to improve their efficacy.

It has been found that the PYY analogues of the present invention generally are soluble around pH 6 and pH 7.

BRIEF SUMMARY OF THE INVENTION

In a first aspect, the invention provides a PYY analogue, wherein the analogue comprises
  i) alanine at the position corresponding to position 4 of hPYY(1-36)
  ii) lysine at the position corresponding to position 7 of hPYY(1-36)
  iii) the sequence QRY at its C-terminal end,
  and wherein a half-life extending group is attached to the epsilon amino group of the lysine at position 7 or of a lysine at positions 6, 10, 11, 14, 17, 21, 22 or 30, or to the carboxylic acid group of the side chain of a aspartate or a glutamate at positions 14 or 30.

In some embodiments, the PYY analogue comprises
  i) alanine at the position corresponding to position 4 of hPYY(1-36)
  ii) lysine at the position corresponding to position 7 of hPYY(1-36)
  iii) glutamate at the position corresponding to position 9 of hPYY(1-36)
  iv) tyrosine at the position corresponding to position 20 of hPYY(1-36)
  v) tryptophan at the position corresponding to position 30 of hPYY(1-36)
  vi) leucine at the position corresponding to position 31 of hPYY(1-36)
  vii) the sequence RQRY (SEQ ID NO: 258) at its C-terminal end,
  and wherein a half-life extending group is attached to the epsilon amino group of the lysine at position 7 or of a lysine at positions 6, 10, 11, 14, 17, 21 or 22, or to the carboxylic acid group of the side chain of a aspartate or a glutamate at position 14.

In some embodiments, the PYY analogue comprises
  i) alanine at the position corresponding to position 4 of hPYY(1-36)
  ii) lysine at the position corresponding to position 7 of hPYY(1-36)
  iii) glutamate at the position corresponding to position 9 of hPYY(1-36)
  iv) tyrosine at the position corresponding to position 20 of hPYY(1-36)
  v) the sequence WLTRQRY (SEQ ID NO: 259) at its C-terminal end, and wherein a half-life extending group is attached to the epsilon amino group of the lysine at position 7 or of a lysine at positions 6, 10, 11, 14, 17, 21, or 22, or to the carboxylic acid group of the side chain of a aspartate or a glutamate at position 14.

In some embodiments, the PYY analogue is in accordance to one of the above embodiments and bears a half-life extending group, which is attached to the epsilon amino group of the lysine at position 7.

In some embodiments of the present invention, the PYY analogue is a compound having the formula:

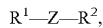

wherein $R^1$ is hydrogen, —C(O)C$_{1-6}$ alkyl, —C(O)C$_6$H$_6$, —C(O)C$_{3-6}$ cycloalkyl, —C(O)C$_{1-6}$ alkyl-C$_{3-6}$ cycloalkyl, or C$_{1-6}$ alkyl or C$_{1-6}$ alkyl-C$_{3-6}$ cycloalkyl:

$R^2$ is OH or NHR$^3$, wherein $R^3$ is hydrogen or C$_{1-3}$ alkyl; and is an amino acid sequence of formula III (SEQ ID NO: 256):

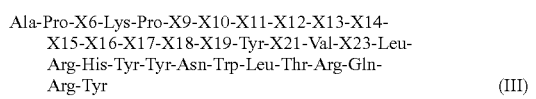

wherein

X6 is selected from the group consisting of Ala and Glu;
X9 is selected from the group consisting of Glu and Gly;
X10 is selected from the group consisting of Ala and Glu;
X11 is selected from the group consisting of Ala, Asp, Glu and Pro;
X12 is selected from the group consisting of Ala and Ser;
X13 is selected from the group consisting of Ala, Glu, Ser, Thr and Pro;
X14 is selected from the group consisting of Ala, Glu and Pro;
X15 is selected from the group consisting of Ala and Glu,
X16 is selected from the group consisting of Ala and Glu;
X17 is selected from the group consisting of Ile, Leu, Thr and Val;
X18 is selected from the group consisting of Glu and Gln;
X19 is selected from the group consisting of Ala, Glu, Arg, Lys, and Gln;
X21 is selected from the group consisting of Glu and Tyr;
X23 is selected from the group consisting of Ala, Glu, Ser and Thr;
and wherein a half-life extending group is attached to the epsilon amino group of the lysine at position 7.

In some embodiments, the half-life extending group consists of a lipophilic substituent X and a linker U, wherein the linker U is attached to the amino acid side chain and X is attached to U, and the linker U consists of one, two or three sub-moieties (U1, U2, U3).

In some embodiments, the lipophilic substituent X is selected from the group consisting of 15-carboxy-pentadecanoyl, 17-carboxy-heptadecanoyl (C18DA) and 19-carboxy-nonadecanoyl, and the linker U consists of one, two or three sub-moieties independently selected from the group consisting of Gly, Glu, γ-Glu, ε-Lys, Ser, and OEG, or independently selected from the group consisting of γ-Glu, and OEG.

In some embodiment the PYY analogue is selected from the compounds 1 to 244 described herein.

In some embodiments the PYY analogue is in the form of a salt, preferably in the form of a pharmaceutically acceptable salt.

The invention further provides a composition comprising a PYY analogue as described herein.

The present invention further provides a PYY analogue for use in a method of medical treatment, e.g. for use in the treatment of obesity and various obesity-related conditions, diseases, or disorders such as type 2 diabetes, NAFLD or NASH.

The invention provides a PYY analogue of the invention for use in a method of treating, inhibiting or reducing weight gain, promoting weight loss and/or reducing excess body weight.

DETAILED DESCRIPTION OF THE INVENTION

Terms, Definitions and Conventions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

Throughout this specification, amino acid positions of the PYY analogues are numbered according to the corresponding position in native human PYY having the sequence shown above.

PYY Analogues

A PYY analogue is a peptide comprising an amino acid sequence corresponding to the amino acid sequence of hPYY (1-36), hPYY(3-36), or hPYY(4-36). In other words a PYY analogue is a peptide, whose structure is related to PYY, in which one or more amino acid residues have been modified when compared to hPYY (1-36), hPYY(3-36), or hPYY(4-36). Possible modifications are substitutions, insertions, or deletions of amino acids at specific positions. A PYY analogue of the invention relates to a peptide that has retained a certain binding affinity (Ki) towards the hNPY2 receptor.

The term "PYY analogue" comprises the peptide itself, i.e., in a non-ionized state, as well as the peptide in ionized state (e.g. when one or more side chains of its amino acids are ionized, i.e. (de)protonated). A PYY analogue in a non-ionized state is also referred to herein as a non-salt form of the PYY analogue.

The term "PYY analogue" may also refer to peptides in which a half-life extending group is attached to one or more amino acids of the peptide. In such cases, a side chain of an amino acid bears a covalently attached half-life extending group.

The term "PPY analogue" also comprises pharmaceutically acceptable salt forms of the PPY analogue, e.g., when the PPY analogue is in an ionized state.

PYY compounds or PYY analogues of the invention may be described by reference to i) the number of the amino acid residue in hPYY(1-36) (SEQ ID NO:2) which corresponds to the amino acid residue which is changed (i.e., the corresponding position in hPYY(1-36), and to ii) the actual change.

The expressions "a position equivalent to" or "corresponding position" are used to characterise the site of change in a variant PYY sequence by reference to hPYY (1-36).

In general throughout the application, when referring to a particular position of a PYY analogue, the position referred to is the position of the PYY analogue corresponding to that particular position of hPYY(1-36).

In the sequence listing, the first amino acid residue of a given sequence is assigned no. 1. This means that e.g. the first amino acid residue of hPYY(3-36), which is isoleucine, is assigned no. 3 in the sequence listings. This position is also referred to as the position corresponding to position 3 of hPYY(1-36).

As used herein, the term "pharmaceutically acceptable salt" is intended to indicate a salt which is not harmful to a patient or subject to which the salt in question is administered. It may suitably be a salt chosen, e.g., among acid addition salts and basic salts. As used herein, "pharmaceutically acceptable salt" refer to derivatives of the disclosed analogues or compounds wherein the parent analogue or compound is modified by making acid or base salts thereof. Examples of acid addition salts include chloride salts, citrate salts and acetate salts. Examples of basic salts include salts, where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)+$, where $R^1$, $R^2$, $R^3$ and $R^4$ independently will typically designate hydrogen or optionally substituted $C_{1-6}$-alkyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", $3^{rd}$ edition, James Swarbrick (Ed.), Informa Healthcare USA (Inc.), NY, USA, 2007, and in *J. Pharm. Sci.* 66: 2 (1977).

The term "agonist" as employed in the context of the invention refers to a substance that activates the receptor type in question, typically by binding to it (i.e. as a ligand).

Each embodiment of the invention described herein may be taken alone or in combination with one or more other embodiments of the invention.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.).

Unless otherwise indicated, reference is made to the L-isomeric forms of the amino acids in question.

Additional abbreviations include the following:
Hyp: 4-hydroxyproline, e.g. (2S,4R)-4-hydroxyproline [also denoted (4R)-4-hydroxy-L-proline]
γ-Glu: γ-glutamic acid [also denoted gGlu]

The term "$C_{1-n}$ alkyl", wherein n is an integer selected from 2, 3, 4, 5 or 6, either alone or in combination with another radical, denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example, the term $C_{3-6}$-cycloalkyl includes cyclopropyl, cyclobutyl, cyclopentyl and cyclohexyl.

"C(O)" or "C(=O)" refers to a carbonyl group.

Nomenclature of compounds:
As an example,
   iVal-APEK(C18DA-gGlu-OEG1-OEG2-)PGE-
      DASPEELQRYYVSLRHYYNALTRQRY-NH$_2$
   (SEQ ID NO: 80), wherein iVal represents 3-methylbutanoyl (—C(O) CH$_2$CH(CH$_3$)$_2$), C18DA represents 17-carboxyheptadecanoyl, gGlu represents L-γ-glutamyl, connected via its amino-group to C18DA and via its γ-carboxy-group to OEG1, and OEG1 represents 2-[2-(2-aminoethoxy)ethoxy]acetoyl, connected via its amino-group to gGlu and via its carboxy-group to OEG2, and OEG2 represents 2-[2-(2-aminoethoxy)ethoxy]acetoyl, connected via its amino-group to OEG1 and via its carboxy-group to ε-amino-group of lysine (K), completely defines the PYY analogue of the following structure (SEQ ID NO: 80):

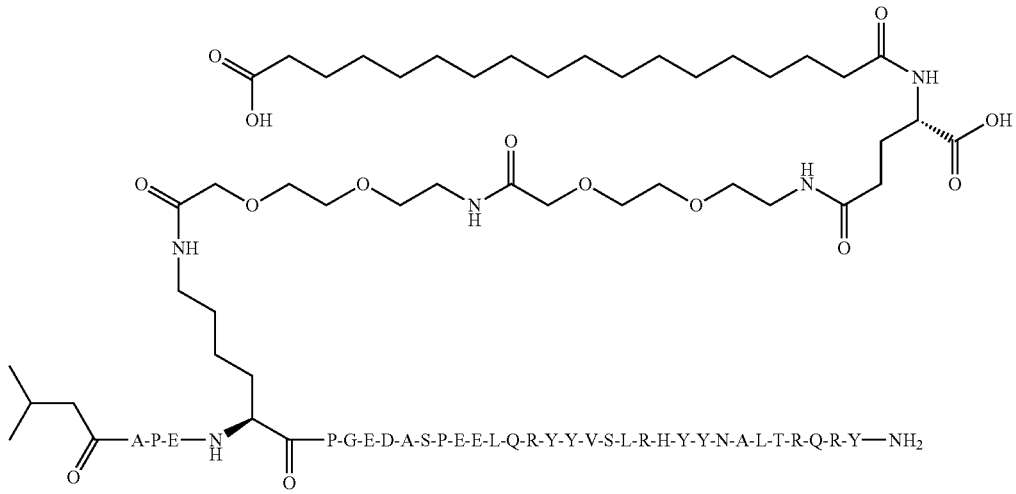

Alternatively, the same compound can be defined in the following way:

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy)acetamido]-[4A,7K,18Q,22V,28Y,30A,31L]hPYY(4-36).

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. weight gain or hyperglycemia) relative to the absence of treatment and is not necessarily meant to imply complete cessation of the relevant disease, disorder or condition.

The terms "prevention" and grammatical variants thereof (e.g., "prevented", "preventing", "prevent") as employed in the present context refer to an approach for hindering or preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of "prevention" may thus be a subject not yet afflicted with the disease or disorder in question. The term "prevention" thus includes inhibiting or slowing the onset of disease relative to the absence of treatment and is not necessarily meant to imply permanent prevention of the relevant disease, disorder or condition.

Half-Life Extending Group

As described herein, a half-life extending group is covalently attached to a functional group of a side chain of an amino acid of the PYY analogue. The half-life extending group comprises or consists of a lipophilic substituent (X) and optionally a linker (U), wherein one end of the linker U (if present) is attached to an amino acid of the PYY analogue and the other end is connected to the lipophilic substituent (-U-X).

Without wishing to be bound by any particular theory, it is thought that such lipophilic substituents (and other classes of half-life extending moieties) bind albumin and other plasma components in the blood stream, thereby shielding the compound of the invention from renal filtration as well as enzymatic degradation and thus possibly enhancing the half-life of the compound in vivo. The lipophilic substituent may also modulate the potency of the compound as an agonist to the NPY2 receptor or other receptors of the NPY receptor family.

The lipophilic substituent X is attached to the linker U via an ester, ether, a sulfonyl ester, a thioester, an amide, an amine, triazole or a sulfonamide. Accordingly, it will be understood that preferably the lipophilic substituent X includes an acyl group, a sulfonyl group, an alkyne, an azide, an N atom, an O atom or an S atom, which forms part of the ester, sulfonyl ester, thioester, triazole, amide, amine or sulfonamide. Preferably, an acyl group, or an O or N atom in the lipophilic substituent X forms part of an amide or ester with the linker U.

The half-life extending group (the linker U thereof, if present) is attached to an amino acid residue of the PYY analogue via an ester, a sulfonyl ester, a thioester, an amide, an amine or a sulfonamide. Accordingly, it will be understood that preferably the half-life extending group (the linker U thereof, if present) includes an acyl group, a sulfonyl group, an N atom, an O atom or an S atom which forms part of the ester, sulfonyl ester, thioester, amide, amine or sulfonamide. Preferably, an acyl group, or an O or N atom in the linker U forms part of an amide or ester with the amino acid residue.

The lipophilic substituent X may comprise a hydrocarbon chain having from 10 to 24 C atoms, e.g. from 14 to 22 C atoms, e.g. from 16 to 20 C atoms. Preferably, it has at least 14 C atoms, and preferably has 20 C atoms or fewer. For example, the hydrocarbon chain may contain 14, 15, 16, 17, 18, 19 or 20 carbon atoms. The hydrocarbon chain may be linear or branched and may be saturated or unsaturated. Furthermore, it can include a functional group at the end of the hydrocarbon chain, e.g. a carboxylic acid group, a sulphonic acid group, or a tetrazole group. From the discussion above it will also be understood that the hydrocarbon chain is preferably substituted with a moiety, which forms part of the attachment to an amino acid residue of the PYY analogue or to the linker U, for example an acyl group, a sulfonyl group, an N atom, an O atom or an S atom.

Most preferably, the hydrocarbon chain is substituted with an acyl group (for the attachment to the linker U), and accordingly the hydrocarbon chain may be part of an alkanoyl group, for example a dodecanoyl, 2-butyloctanoyl, tetradecanoyl, hexadecanoyl, heptadecanoyl, octadecanoyl, nonadecanoyl or eicosanoyl group. These hydrocarbon chains substituted with an acyl group at one end may further be functionalized with a carboxylic acid group at the other end of the chain. Examples of functionalized hydrocarbon chains (e.g. lipophilic substituents X) are 15-carboxy-pentadecanoyl, 17-carboxy-heptadecanoyl and 19-carboxy-nonadecanoyl.

In certain embodiments, the linker moiety U may itself comprise one, two, three or more linked sub-moieties ($U^1$, $U^2$, $U^3$, etc). In some of these embodiments the linker may comprise one or more (e.g. one, two or three) linked amino acid residues, which may each independently be a residue of any naturally occurring or non-naturally occurring amino acid. For example, the linker may comprise one, two or three linked amino acid residues, each of which may independently be a residue of Gly, Pro, Ala, Val, Leu, Ile, Cys, Phe, Tyr, His, Lys, Arg, Gln, Asn, α-Glu, γ-Glu, ε-Lys, Asp, β-Asp, Ser, Thr, Aib, AEA (2-(2-aminoethoxy)acetic acid), AEEEA (2-{2-[2-(2-aminoethoxy)ethoxy]ethoxy}acetic acid), $H_2N$-dPEG(4)-COOH (15-amino-4,7,10,13-tetraoxa-pentadecanoic acid), $H_2N$-dPEG(6)-COOH (1-amino-3,6,9,12,15,18-hexaoxahenicosan-21-oic acid), $H_2N$-dPEG(12)-COOH (1-amino-3,6,9,12,15,18,21,24,27,30,33,36-dodecaoxanonatriacontan-39-oic acid), OEG-OEG (2-[2-(2-{2-[2-(2-aminoethoxy)ethoxy]acetamido}ethoxy)ethoxy]acetic acid), H-Ebes (3-({2-[2-(2-aminoethoxy)ethoxy]ethyl}carbamoyl)propanoic acid), H-DOOA-DIG-OH (2-[({2-[2-(2-aminoethoxy)ethoxy]ethyl}carbamoyl)methoxy]acetic acid), H-TTD-DIG-OH (2-{[(3-{2-[2-(3-aminopropoxy)ethoxy]ethoxy}propyl)carbamoyl]methoxy}acetic acid), H-TTDS-OH (3-[(3-{2-[2-(3- aminopropoxy)ethoxy]ethoxy}propyl)-carbamoyl] propanoic acid), or 8Ado (i.e. 8-amino-3,6-dioxaoctanoyl also denoted OEG herein).

References to γ-Glu, ε-Lys, and β-Asp indicate residues of amino acids which participate in bonds via their side chain carboxyl or amine functional groups. Thus γ-Glu, and β-Asp participate in bonds via their alpha amino and side chain carboxyl groups, while ε-Lys participates via its carboxyl and side chain amino groups. In the context of the present invention, γ-Glu, gGlu and isoGlu are used interchangeably.

In certain embodiments, the linker U comprises or consists of one, two or three independently selected sub-moieties ($U^1$, $U^2$, $U^3$) selected from the group consisting of Ala, Glu, γ-Glu, Gly, ε-Lys, Ser, OEG and OEG-OEG.

Linkers consisting of γ-Glu, γ-Glu-γ-Glu, γ-Glu-OEG, OEG-OEG, γ-Glu-γ-Glu-OEG, γ-Glu-OEG-OEG may be preferred.

Synthesis of PYY Analogues

The invention provides a method of synthesis of a PYY analogue of the invention. The PYY analogues may be manufactured by standard synthetic methods, including standard solid-phase or liquid-phase methodology. Peptides are assembled either stepwise or by merging fragments, and optionally isolated and purified yielding the final peptide product. Synthesis examples are described in numerous publications, including Fields, G. B. et al., "Principles and Practice of Solid-Phase Peptide Synthesis" in Synthetic Peptides, Grant G. A. (ed.), Oxford University Press ($2^{nd}$ edition, 2002).

Embodiments

In a first aspect, the invention provides a PYY analogue, wherein the analogue comprises
  i) alanine at the position corresponding to position 4 of hPYY(1-36)
  ii) lysine at the position corresponding to position 7 of hPYY(1-36)
  iii) the sequence QRY at its C-terminal end,
  and wherein a half-life extending group is attached to the epsilon amino group of the lysine at position 7 or of a lysine at positions 6, 10, 11, 14, 17, 21, 22 or 30, or to the carboxylic acid group of the side chain of a aspartate or a glutamate at positions 14 or 30.

In some embodiments, the PYY analogue comprises glutamate at the position corresponding to position 9 of hPYY(1-36).

In some embodiments, the PYY analogue comprises tyrosine at the position corresponding to position 20 of hPYY(1-36).

In some embodiment, the PYY analogue comprises tryptophan at the position corresponding to position 30 of hPYY(1-36).

In some embodiments, the PYY analogue comprises leucine at the position corresponding to position 31 of hPYY(1-36).

In some embodiments, the PYY analogue comprises arginine or lysine at the position corresponding to position 33 of hPYY(1-36).

In some embodiments, the PYY analogue bears a half-life extending group, which is attached to the epsilon amino group of the lysine at position 7.

In some embodiments of the present invention, the half-life extending group consists of a lipophilic substituent X and a linker U, wherein the linker U is attached to the amino acid side chain, and X is attached to U.

In some embodiments, the lipophilic substituent X is selected from the group consisting of 15-carboxy-pentadecanoyl, 17-carboxy-heptadecanoyl (C18DA) and 19-carboxy-nonadecanoyl.

In some embodiments the linker U comprises one or more sub-moieties, wherein at least one of the sub-moieties is OEG.

In some embodiments the linker U consists of one, two or three sub-moieties (U1, U2, U3), wherein the sub-moiety is independently selected from the group consisting of Gly, Glu, γ-Glu, ε-Lys, Ser and OEG.

In some embodiments, the PYY analogue comprises
  i) alanine at the position corresponding to position 4 of hPYY(1-36)
  ii) lysine at the position corresponding to position 7 of hPYY(1-36)
  iii) glutamate at the position corresponding to position 9 of hPYY(1-36)
  iv) tyrosine at the position corresponding to position 20 of hPYY(1-36)
  v) tryptophan at the position corresponding to position 30 of hPYY(1-36)
  vi) leucine at the position corresponding to position 31 of hPYY(1-36)
  vii) the sequence RQRY (SEQ ID NO: 258) at its C-terminal end,
  and wherein a half-life extending group is attached to the epsilon amino group of the lysine at position 7 or of a lysine at positions 6, 10, 11, 14, 17, 21 or 22, or to the carboxylic acid group of the side chain of a aspartate or a glutamate at position 14.

In some embodiments, the PYY analogue comprises threonine at the position corresponding to position 32 of hPYY(1-36).

In some embodiments, the PYY analogue comprises the sequence WLTRQRY (SEQ ID NO: 259) at its C-terminal end.

In some embodiments, the PYY analogue bears a half-life extending group, which is attached to the epsilon amino group of the lysine at position 7.

In some embodiments, the PYY analogue comprises
  i) alanine at the position corresponding to position 4 of hPYY(1-36)
  ii) lysine at the position corresponding to position 7 of hPYY(1-36)
  iii) glutamate at the position corresponding to position 9 of hPYY(1-36)
  iv) tyrosine at the position corresponding to position 20 of hPYY(1-36)
  v) the sequence WLTRQRY (SEQ ID NO: 259) at its C-terminal end,
  and wherein a half-life extending group is attached to the epsilon amino group of the lysine at position 7 or of a lysine at positions 6, 10, 11, 14, 17, 21, or 22, or to the carboxylic acid group of the side chain of a aspartate or a glutamate at position 14.

In some embodiments, the PYY analogue comprises arginine at the position corresponding to position 25 of hPYY(1-36).

In some embodiments, the PYY analogue bears a half-life extending group, which is attached to the epsilon amino group of the lysine at position 7.

In some embodiments, exactly one half-life extending group is attached to the PYY analogue, said half-life extending group being attached to the epsilon amino group of the lysine at position 7.

In some embodiments of the present invention, the PYY analogue is a compound having the formula:

$$R^1-Z-R^2,$$

wherein $R^1$ is hydrogen, —C(O)C$_{1-6}$ alkyl, —C(O)C$_6$H$_6$, —C(O)C$_{3-6}$ cycloalkyl, —C(O)C$_{1-6}$ alkyl-C$_{3-6}$ cycloalkyl, C$_{1-6}$ alkyl or C$_{1-6}$ alkyl-C$_{3-6}$ cycloalkyl:
$R^2$ is OH or NHR$^3$, wherein $R^3$ is hydrogen or C$_{1-3}$ alkyl; and
Z is a peptide comprising an amino acid sequence of formula I (SEQ ID NO: 254):

Ala-X5-X6-Lys-X8-X9-X10-X11-X12-X13-X14-
X15-X16-X17-X18-X19-Tyr-X21-X22-X23-
X24-Arg-X26-X27-X28-X29-X30-X31-X32-
Arg-Gln-Arg-Tyr (I)

wherein
X5 is selected from the group consisting of Pro and Hyp;
X6 is selected from the group consisting of Ala and Glu;
X8 is selected from the group consisting of Ala, Ile, Pro, Thr, Val and Hyp;
X9 is selected from the group consisting of Glu, Gly, Gln and Pro;
X10 is selected from the group consisting of Ala and Glu;
X11 is selected from the group consisting of Ala, Asp, Glu and Pro;
X12 is selected from the group consisting of Ala, Gly, Ser, Thr and Val;
X13 is selected from the group consisting of Ala, Glu, Ser, Gln, Thr and Pro;
X14 is selected from the group consisting of Ala, Glu, Gly, Pro and Hyp;
X15 is selected from the group consisting of Ala, Glu and Ser;
X16 is selected from the group consisting of Ala, Glu and Ser;
X17 is selected from the group consisting of Ala, Ile, Leu, Thr and Val;
X18 is selected from the group consisting of Glu and Gln;
X19 is selected from the group consisting of Ala, Glu, Arg, Lys and Gln;
X21 is selected from the group consisting of Ala, Glu, Gln and Tyr;
X22 is selected from the group consisting of Ile, Ser, Thr and Val;
X23 is selected from the group consisting of Ala, Glu, Ser and Thr;
X24 is selected from the group consisting of Ala, Ile, Leu, Thr and Val;
X26 is selected from the group consisting of Ala, His and Lys;
X27 is selected from the group consisting of Gln and Tyr;
X28 is selected from the group consisting of His, Trp and Tyr;
X29 is selected from the group consisting of Asn, Trp and Tyr;
X30 is selected from the group consisting of Ala, His, Trp, and Tyr;
X31 is selected from the group consisting of Ala, Ile, Leu and Thr;
X32 is selected from the group consisting of Gln, Leu and Thr;
wherein one to three amino acids of X5, X6, X8-X19, X21-X24 and X26-X32 may be absent,
and wherein a half-life extending group is attached to the epsilon amino group of the lysine at position 7.

In a further embodiment the PYY analogue is according to the previous embodiment, wherein none of X5, X6, X8-X19, X21-X24 and X26-X32 is absent.
In a further embodiment $R^1$ is —C(O)C$_{1-4}$ alkyl, —C(O)C$_{3-5}$ cycloalkyl, —C(O)C$_{1-3}$ alkyl-C$_{3-4}$ cycloalkyl, C$_{1-4}$ alkyl or C$_{1-3}$ alkyl-C$_{3-4}$ cycloalkyl.
In a further embodiment $R^1$ is —C(O)CH$_2$CH(CH$_3$)$_2$, —C(O)CH$_2$-cyclobutyl, —C(O)CH$_2$-cyclopropyl.
It has been found that the PYY analogues of the present invention—bearing alanine at position 4 and lysine at position 7—generally are soluble around pH 6 and pH 7.

Peptide therapeutics are usually provided as pharmaceutical liquid formulation in a pre-filled ready-to-use injection device. These peptide formulations for subcutaneous administration have limited application volumes. Therefore, good solubility of the peptides is a requirement for the application in a ready-to-use injection device.

A further important aspect is the long-term stability and solubility of the peptides in the liquid formulation. A property of fundamental importance for physical stability is the intrinsic solubility (at a given pH value).

A broad pH range, within which a peptide therapeutic is reasonably soluble (solubility window), is also desirable as it allows more flexibility for pharmaceutical formulation development. This flexibility might be desirable as other factors, such as chemical stability, are also pH dependent. In general, a peptide formulation around pH 6.0 is believed to show reduced rates of oxidation (e.g. Cys oxidation, disulphide crosslinking, and oxidation of Trp residues), deamination and aspartate isomerization as compared to a formulation at pH 7. For instance, Bak et al. (A. Bak, D. Leung, S. E. Barrett, S. Forster, E. D. Minnihan, A. W. Leithead, J. Cunningham, N. Toussaint, L. S. Crocker, The AAPS Journal, Vol. 17, No. 1, 2015, p. 144-155) states that oxidation propensity generally lessens at lower pH and suggests maintenance at pH<7 as a strategy for mitigation risks related to oxidation. Therefore, it might be desirable to have the option to formulate around pH 6 in case chemical stability of peptides containing asparagine, aspartate or glutamine, tryptophan, cysteine or methionine is an issue.

Efficacy of obesity therapeutics is limited. However, efficacy might be improved by combining different therapeutic principles. NPY2 receptor agonists seem attractive partners for combination with other weight reducing therapeutics. For example, NPY2 receptor agonists show enhanced weight loss efficacy with GLP-1 receptor agonists (e.g. WO2005/077072, WO2014/178018, WO2018/081370) or amylin (e.g. WO2006/066024, WO2009/064298). Native amylin and many amylin (or calcitonin) analogues comprise a disulphide bridge. Therefore, a fix-dose combination of a PYY analogue with an amylin analogue might benefit from the opportunity to formulate at a lower pH where the disulphide bridge of the amylin analogue potentially shows improved stability (e.g. due to reduced intramolecular disulphide bond crosslinking reactions). This illustrates that the advantage to be able to formulate at a pH below 7 may not (only) be due to a higher stability of the NPY analogue but may lie therein that the combination partner shows improved stability (or solubility) at a lower pH.

Therefore, to enable co-formulation development with a diverse range of partners, it is highly desirable to identify NPY2 receptor agonists with a wide solubility window.

Increased solubility, however, should not come at the cost of reduced activity or potency. It was surprisingly found that the alanine at position 4 increases solubility around pH 6 in the PYY analogues of the invention with no or only small negative effects on activity or potency or other important properties (e.g. chemical or physical stability).

Long in-vivo half-life is also a beneficial property for agents to reduce food intake in overweight or obese patients. Compounds with a long-acting profile (as compared to the very short in-vivo half-life of native (human) PYY) reducing the frequency of administration are desirable.

In one aspect, the invention relates to PYY analogues being NPY2 receptor agonists.

In one aspect, the invention relates to PYY analogues showing selectivity towards the NPY receptor subtype Y2 as compared to Y receptor subtypes Y1, Y4 and Y5.

In one aspect, the invention relates to PYY analogues with extended half-live, e.g. with longer half-life than the half-life of hPYY(3-36). For example, the PYY analogues of the invention are suitable for once weekly administration.

Additionally or alternatively, the invention relates to PYY analogues having high chemical and/or physical stability, e.g. around pH 6 or pH 7.

Further, more specific embodiments are defined below:

In a further embodiment of the present invention, the PYY analogue is a compound having the formula:

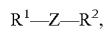

wherein $R^1$ is hydrogen, —C(O)C$_{1-6}$ alkyl, —C(O)C$_6$H$_6$, —C(O)C$_{3-6}$ cycloalkyl, —C(O)C$_{1-6}$ alkyl-C$_{3-6}$ cycloalkyl, or C$_{1-6}$ alkyl or C$_{1-6}$ alkyl-C$_{3-6}$ cycloalkyl;

$R^2$ is OH or NHR$^3$, wherein $R^3$ is hydrogen or C$_{1-3}$ alkyl; and

Z is an amino acid sequence of formula II (SEQ ID NO: 255):

Ala-X5-X6-Lys-X8-X9-X10-X11-X12-X13-X14-
X15-X16-X17-X18-X19-Tyr-X21-X22-X23-
X24-Arg-X26-Tyr-X28-X29-X30-X31-X32-Arg-
Gln-Arg-Tyr  (II)

wherein

X5 is selected from the group consisting of Pro and Hyp;
X6 is selected from the group consisting of Ala and Glu;
X8 is selected from the group consisting of Ala, Pro and Hyp;
X9 is selected from the group consisting of Gln, Gly, Glu and Pro;
X10 is selected from the group consisting of Ala and Glu;
X11 is selected from the group consisting of Ala, Asp, Glu and Pro;
X12 is selected from the group consisting of Ala, Gly and Ser;
X13 is selected from the group consisting of Ala, Glu, Ser, Thr and Pro;
X14 is selected from the group consisting of Ala, Glu, Pro and Hyp;
X15 is selected from the group consisting of Ala, Glu and Ser;
X16 is selected from the group consisting of Ala, Glu and Ser;
X17 is selected from the group consisting of Ile, Leu, Thr and Val;
X18 is selected from the group consisting of Gln and Glu;
X19 is selected from the group consisting of Ala, Glu, Arg, Lys and Gln
X21 is selected from the group consisting of Ala, Glu, Gln and Tyr;
X22 is selected from the group consisting of Ile, Ser, Thr and Val;
X23 is selected from the group consisting of Ala, Glu, Ser and Thr;

X24 is selected from the group consisting of Ala, Ile, Leu, Thr and Val;
X26 is selected from the group consisting of Ala, His and Lys;
X28 is selected from the group consisting of Trp and Tyr;
X29 is selected from the group consisting of Asn and Tyr;
X30 is selected from the group consisting of His, Trp, and Tyr;
X31 is selected from the group consisting of Ala, Ile and Leu;
X32 is selected from the group consisting of Gln and Thr;
and wherein a half-life extending group is attached to the epsilon amino group of the lysine at position 7.

In some embodiments in line with the embodiment described immediately above, the half-life extending group consists of a lipophilic substituent X and a linker U, wherein the linker U is attached to the amino acid side chain, and X is attached to U, and wherein the lipophilic substituent X is selected from the group consisting of 15-carboxy-pentadecanoyl, 17-carboxy-heptadecanoyl (C18DA) and 19-carboxy-nonadecanoyl, and the linker U consists of one, two or three sub-moieties (U1, U2, U3), wherein the sub-moiety is independently selected from the group consisting of Gly, Glu, γ-Glu, ε-Lys, Ser and OEG.

In some embodiments of the present invention, the PYY analogue is a compound having the formula:

wherein $R^1$ is hydrogen, —C(O)C$_{1-6}$ alkyl, —C(O)C$_6$H$_6$, —C(O)C$_{3-6}$ cycloalkyl, —C(O)C$_{1-6}$ alkyl-C$_{3-6}$ cycloalkyl, or C$_{1-6}$ alkyl or C$_{1-6}$ alkyl-C$_{3-6}$ cycloalkyl;

$R^2$ is OH or NHR$^3$, wherein $R^3$ is hydrogen or C$_{1-3}$ alkyl; and

Z is an amino acid sequence of formula III (SEQ ID NO: 256):

Ala-Pro-X6-Lys-Pro-X9-X10-X11-X12-X13-X14-
X15-X16-X17-X18-X19-Tyr-X21-Val-X23-Leu-
Arg-His-Tyr-Tyr-Asn-Trp-Leu-Thr-Arg-Gln-
Arg-Tyr  (III)

wherein

X6 is selected from the group consisting of Ala and Glu;
X9 is selected from the group consisting of Glu and Gly;
X10 is selected from the group consisting of Ala and Glu;
X11 is selected from the group consisting of Ala, Asp, Glu and Pro;
X12 is selected from the group consisting of Ala and Ser;
X13 is selected from the group consisting of Ala, Glu, Ser, Thr and Pro;
X14 is selected from the group consisting of Ala, Glu and Pro;
X15 is selected from the group consisting of Ala and Glu;
X16 is selected from the group consisting of Ala and Glu;
X17 is selected from the group consisting of Ile, Leu, Thr and Val;
X18 is selected from the group consisting of Glu and Gln;
X19 is selected from the group consisting of Ala, Glu, Arg, Lys, and Gln;
X21 is selected from the group consisting of Glu and Tyr;
X23 is selected from the group consisting of Ala, Glu, Ser and Thr;
and wherein a half-life extending group is attached to the epsilon amino group of the lysine at position 7.

In further embodiments, the PYY analogue is a compound according to formula I to III, wherein at least two amino acids from X6, X10, X11, X13 and X23 are selected from the group consisting of Asp and Glu.

In further embodiments, the PYY analogue is a compound according to any of the previous embodiments, wherein only one of X6, X10 and X15 is Ala.

In a further embodiment of the present invention, the PYY analogue is a compound having the formula:

$R^1—Z—R^2$, wherein $R^1$ is hydrogen, $—C(O)C_{1-6}$ alkyl, $—C(O)C_6H_6$, $—C(O)C_{3-6}$ cycloalkyl, $—C(O)C_{1-6}$ alkyl-$C_{3-6}$ cycloalkyl, or $C_{1-6}$ alkyl or $C_{1-6}$ alkyl-$C_{3-6}$ cycloalkyl:

$R^2$ is OH or $NHR^3$, wherein $R^3$ is hydrogen or $C_{1-3}$ alkyl; and

Z is an amino acid sequence of formula IV (SEQ ID NO: 257):

Ala-Pro-X6-Lys-Pro-Glu-X10-X11-Ala-X13-X14-Glu-Glu-X17-Gln-X19-Tyr-Tyr-Val-X23-Leu-Arg-His-Tyr-Tyr-Asn-Trp-Leu-Thr-Arg-Gln-Arg-Tyr    (IV)

wherein
X6 is selected from the group consisting of Ala and Glu;
X10 is selected from the group consisting of Ala and Glu;
X11 is selected from the group consisting of Ala, Asp and Glu;
X13 is selected from the group consisting of Ala, Glu, Ser, and Thr;
X14 is selected from the group consisting of Ala, Pro and Hyp;
X17 is selected from the group consisting of Ile and Leu;
X19 is selected from the group consisting of Arg, Lys, and Gln;
X23 is selected from the group consisting of Ala, Glu, and Ser;
and wherein a half-life extending group is attached to the epsilon amino group of the lysine at position 7.

In a further embodiment, the PYY analogue is a compound according to formula IV, wherein at least 2 amino acid from X6, X10, X11, X13 and X23 are selected from Asp or Glu.

In further embodiments, the PYY analogue is a compound according to formula IV, wherein only one of X6, and X10 is Ala.

In further embodiments, the PYY analogue is a compound according to any of the previous embodiments, wherein X6 is Ala.

In further embodiments, $R^1$ is hydrogen, $—C(O)C_{1-6}$ alkyl, $—C(O)C_{3-6}$ cycloalkyl, or $C_{1-6}$ alkyl.

In further embodiments, $R^1$ is hydrogen or $—C(O)C_{1-6}$ alkyl.

In further embodiments, $R^1$ is hydrogen or $—C(O)C_{1-4}$ alkyl.

In more specific embodiments, $R^1$ is $—C(O)CH_2CH(CH_3)_2$.

In more specific embodiments, $R^2$ is $NH_2$.

In some embodiments of the present invention, the PYY analogue is a compound having the formula:

$R^1—Z—R^2$, wherein $R^1$ and $R^2$ are defined as in any of the definitions above; and Z is an amino acid sequence selected from Table 1:

TABLE 1

| Compound | Sequence | SEQ ID NO |
|---|---|---|
| 1 | APEKPEEDAQPEELQEYYVSLRHYYNWLTRQRY | 5 |
| 2 | AHypEKPEEDASPEELQRYYVSLRHYYNWLTRQRY | 6 |
| 3 | APEKPEEEASPAELQRYYVSLRHYYNWLTRQRY | 7 |

TABLE 1-continued

| Compound | Sequence | SEQ ID NO |
|---|---|---|
| 4 | APEKPEEDASPEELQRYYVSLRHYYNWLQRQRY | 8 |
| 5 | APEKPEEEVSPEELQRYYVSLRHYYNWLTRQRY | 9 |
| 6 | APEKPEEEASPEELQRYYVSARHYYNWLTRQRY | 10 |
| 7 | APEKPEEDASPEELQAYYVSLRHYYNWLTRQRY | 11 |
| 8 | APEKPEEDASEEELQQYYVSLRHYYNWLTRQRY | 12 |
| 9 | APEKPEEDASPEEIQRYYVELRHYYNWLTRQRY | 13 |
| 10 | APEKPEADASPEETQRYYVSLRHYYNWLTRQRY | 14 |
| 11 | APEKPEEDASPEEIQQYYVSLRHYYNWLTRQRY | 15 |
| 12 | APEKPEEDAPGEELQRYYVSLRHYYNWLTRQRY | 16 |
| 13 | APEKPEEDAAPEELQQYYVSLRHYYNWLTRQRY | 17 |
| 14 | APEKPEADATPEELQRYYVSLRHYYNWLTRQRY | 18 |
| 15 | APEKPEEDASPEEIQRYEVSLRHYYNWLTRQRY | 19 |
| 16 | APEKPEEDASPEETQRYYVTLRHYYNWLTRQRY | 20 |
| 17 | APEKPEEDASPAELQRYYVSLRHYYNWLTRQRY | 21 |
| 18 | APEKPEEDAEPEELQQYYVSLRHYYNWLTRQRY | 22 |
| 19 | APEKPEADASPEELQQYYVSLRHYYNWLTRQRY | 23 |
| 20 | APEKPEEDAAPEELQRYYVELRHYYNWLTRQRY | 24 |
| 21 | APEKPEEDASPEELQKYYVSLRHYYNWLTRQRY | 25 |
| 22 | APEKPEEDASPEELQRYYTSLRHYYNWLTRQRY | 26 |
| 23 | APAKPEEDASPEEIQRYYVSLRHYYNWLTRQRY | 27 |
| 24 | APEKPEEDASPEELQRYYVSLRKYYNWLTRQRY | 28 |
| 25 | APEKPEEEASAEELQRYYVSLRHYYNWLTRQRY | 29 |
| 26 | APEKPPEDATPEELQRYYVSLRHYYNWLTRQRY | 30 |
| 27 | APEKPPEDAEPEELQRYYVSLRHYYNWLTRQRY | 31 |
| 28 | APEKPEEDTSPEELQRYYVELRHYYNWLTRQRY | 32 |
| 29 | APEKPEAPASPEELQRYYVELRHYYNWLTRQRY | 33 |
| 30 | APEKPEADASEEELQRYYVSLRHYYNWLTRQRY | 34 |
| 31 | APEKPEEDASPEETQRYYVALRHYYNWLTRQRY | 35 |
| 32 | APEKPEEDTSPEELQRYEVSLRHYYNWLTRQRY | 36 |
| 33 | APEKPEEPASPEELQRYYVELRHYYNWLTRQRY | 37 |
| 34 | APEKPEEDASPEELQRYYVSTRHYYNWLTRQRY | 38 |
| 35 | APEKPEEDAAPEETQRYYVSLRHYYNWLTRQRY | 39 |
| 36 | APEKAEEDAEPEELQRYYVSLRHYYNWLTRQRY | 40 |
| 37 | APEKPEEDASPEETQRYEVSLRHYYNWLTRQRY | 41 |
| 38 | APEKPPEDASPEELQRYYVALRHYYNWLTRQRY | 42 |
| 39 | APEKPPADAEPEELQRYYVSLRHYYNWLTRQRY | 43 |
| 40 | APEKPEEDATPEETQRYYVSLRHYYNWLTRQRY | 44 |
| 41 | APEKPEEEATPEELQRYYVSLRHYYNWLTRQRY | 45 |

TABLE 1-continued

| Compound | Sequence | SEQ ID NO |
|---|---|---|
| 42 | APEKPEEAASPEELQRYYVSTRHYYNWLTRQRY | 46 |
| 43 | APEKPEAPASPEELQRYYVSLRHYYNWLTRQRY | 47 |
| 44 | APEKPEEEASPEELQRYYVSLRHYYNWITRQRY | 48 |
| 45 | APEKPEEEASPESLQRYYVSLRHYYNWLTRQRY | 49 |
| 46 | APEKPEEEASPEELQRYYVSLRHYYNWLTRQRY | 50 |
| 47 | APEKPPADASPEELQRYYVSLRHYYNWLTRQRY | 51 |
| 48 | APEKPEEDTEPEELQRYYVSLRHYYNWLTRQRY | 52 |
| 49 | APEKPEEDASPEELQQYYVELRHYYNWLTRQRY | 53 |
| 50 | APEKPEEDASAEELQRYYVSLRHYYNWITRQRY | 54 |
| 51 | APEKAEEEASPEELQRYYVSLRHYYNWLTRQRY | 55 |
| 52 | APEKAEEDASEEELQRYYVSLRHYYNWLTRQRY | 56 |
| 53 | APEKPEADASPEEIQRYYVSLRHYYNWLTRQRY | 57 |
| 54 | APEKPEEDASPEELQRYYVSLRHYYNWLTRQRY | 58 |
| 55 | APEKPEEDASPEEAQRYYVSLRHYYNWLTRQRY | 59 |
| 56 | APEKPEADAEPEELQRYYVSLRHYYNWLTRQRY | 60 |
| 57 | APEKPEEDASAEEIQRYYVSLRHYYNWLTRQRY | 61 |
| 58 | APEKPEEDASPEELQQYYVSLRHYYNWLTRQRY | 62 |
| 59 | APEKPEEDASPEETEQYYVSLRHYYNWLTRQRY | 63 |
| 60 | APEKPEEAASPEELEQYYVSLRHYYNWLTRQRY | 64 |
| 61 | APEKPPEDASPEEIQRYYVSLRHYYNWLTRQRY | 65 |
| 62 | APEKPGEDASPEELERYYVSLRHYYNWLTRQRY | 66 |
| 63 | APEKPEEDASPEELQRYYVSLRAYYNWLTRQRY | 67 |
| 64 | APEKPGEDASPEELQRYYVVSLRHYYNWLTRQRY | 68 |
| 65 | APEKPEEDASPEELQRYYVEIRHYYNWLTRQRY | 69 |
| 66 | APEKPEEDASAEETQRYYVSLRHYYNWLTRQRY | 70 |
| 67 | APEKPEEDSAPEELQRYYVSLRHYYNWLTRQRY | 71 |
| 68 | APEKPEEEASPEELQAYYVSLRHYYNWLTRQRY | 72 |
| 69 | APEKPEEDSSAEELQRYYVSLRHYYNWLTRQRY | 73 |
| 70 | APEKPEEAASPEELQRYEVSLRHYYNWLTRQRY | 74 |
| 71 | APEKPEEEASPSELQRYYVSLRHYYNWLTRQRY | 75 |
| 72 | APEKPEEEGSPEELQRYYVSLRHYYNWLTRQRY | 76 |
| 73 | APEKPEEEASPEELQRYYVSLRAYYNWLTRQRY | 77 |
| 74 | APEKPEEDASAEELQRYYVALRHYYNWLTRQRY | 78 |
| 75 | APEKPEEDASAEELQRYYVTLRHYYNWLTRQRY | 79 |
| 76 | APEKPGEDASPEELQRYYVSLRHYYNALTRQRY | 80 |
| 77 | APEKPEEDASEEELQRYYVELRHYYNWLTRQRY | 81 |
| 78 | APEKPEEDAEPEELQQYYVTLRHYYNWLTRQRY | 82 |
| 79 | APEKPEEEASEEELQRYYVSLRHYYNWLTRQRY | 83 |
| 80 | APEKPEEEASPEETQRYYVSLRHYYNWLTRQRY | 84 |
| 81 | APEKPEEDASPEELQRYYVSIRHYYNWLTRQRY | 85 |
| 82 | APEKPEEDASPEALQRYYVALRHYYNWLTRQRY | 86 |
| 83 | APEKPEADASPAELQRYYVSLRHYYNWLTRQRY | 87 |
| 84 | APEKPEEDASPEEIQRYYVSLRHYYNWLTRQRY | 88 |
| 85 | APEKPEEDASPEELQRYAVSLRHYYNWLTRQRY | 89 |
| 86 | APEKPEADASPEELQRYEVSLRHYYNWLTRQRY | 90 |
| 87 | APEKPEEDSSPAELQRYYVSLRHYYNWLTRQRY | 91 |
| 88 | APEKPPEDASPEELQRYYVELRHYYNWLTRQRY | 92 |
| 89 | APEKPEEEAEPEELQRYYVELRHYYNWLTRQRY | 93 |
| 90 | APEKPEEDASPEELQRYEVSLRHYYNWLTRQRY | 94 |
| 91 | APEKPEEDAPAEELQRYYVELRHYYNWLTRQRY | 95 |
| 92 | APEKPEEDTSPEELQRYYVSLRHYYNWLTRQRY | 96 |
| 93 | APEKPEEDASAEELQKYYVSLRHYYNWLTRQRY | 97 |
| 94 | APEKPEEDASPEETQRYYVELRHYYNWLTRQRY | 98 |
| 95 | APEKPEEDASPAEIQRYYVSLRHYYNWLTRQRY | 99 |
| 96 | APEKPEADASPEELQRYYVSLRHYYNWLTRQRY | 100 |
| 97 | APEKPEEDASPEELQRYYVALRHYYNWLTRQRY | 101 |
| 98 | APEKPEEDASPEELQRYYSALRHYYNWLTRQRY | 102 |
| 99 | APEKPEEDAEAEELQRYYVSLRHYYNWLTRQRY | 103 |
| 100 | APAKPPEDASPEELQRYYVSLRHYYNWLTRQRY | 104 |
| 101 | APEKPEEDATPEELQRYYVELRHYYNWLTRQRY | 105 |
| 102 | APEKPEEDASPEELQRYYVTLRHYYNWLTRQRY | 106 |
| 103 | APAKPEEDASEEELQRYYVSLRHYYNWLTRQRY | 107 |
| 104 | APEKPEEDASAEELQRYYVSLRHYYNWLTRQRY | 108 |
| 105 | APEKPEEDAEPEELQEYYVSLRHYYNWLTRQRY | 109 |
| 106 | APAKPEEDATPEELQRYYVSLRHYYNWLTRQRY | 110 |
| 107 | APEKPEEDASPEELQKYYVALRHYYNWLTRQRY | 111 |
| 108 | APEKPEEDASPEELQRYYVELRHYYNWLTRQRY | 112 |
| 109 | APEKPEEAASPEELQRYYVSLRHYYNWLTRQRY | 113 |
| 110 | APEKPEEDAEPEEIQRYYVSLRHYYNWLTRQRY | 114 |
| 111 | APEKPEEDAEPEELQRYYVELRHYYNWLTRQRY | 115 |
| 112 | APEKPEEDATPEELQRYYVSLRHYYNWLTRQRY | 116 |
| 113 | APEKAEEDATPEELQRYYVSLRHYYNWLTRQRY | 117 |
| 114 | APEKPEEDASPEELQRYYVSLRHYHWYLTRQRY | 118 |
| 115 | APEKPEEEASPEALQRYYVSLRHYYNWLTRQRY | 119 |
| 116 | APEKPEEDAAAEELQRYYVSLRHYYNWLTRQRY | 120 |
| 117 | APAKPEEDASPEELQRYYVALRHYYNWLTRQRY | 121 |
| 118 | APEKPEEDASAAELQRYYVSLRHYYNWLTRQRY | 122 |

TABLE 1-continued

| Compound | Sequence | SEQ ID NO |
|---|---|---|
| 119 | APEKPEEEASPEELQRYYVTLRHYYNWLTRQRY | 123 |
| 120 | APEKPGEDAEEEELQEYYVSLRHYYNWLTRQRY | 124 |
| 121 | APAKPEADASPEELQRYYVSLRHYYNWLTRQRY | 125 |
| 122 | APEKPEEDAAPEELQRYYVSLRHYYNWLTRQRY | 126 |
| 123 | APEKPEEDASPEELQRYYVSLRHYWYHLTRQRY | 127 |
| 124 | APEKPEEDAAPEEIQRYYVSLRHYYNWLTRQRY | 128 |
| 125 | APEKPGEDASPEELQRYYVSLRHYYNWATRQRY | 129 |
| 126 | APAKPEEDSSPEELQRYYVSLRHYYNWLTRQRY | 130 |
| 127 | APAKPEEDASAEELQRYYVSLRHYYNWLTRQRY | 131 |
| 128 | APEKPEEDAPAEEIQRYYVSLRHYYNWLTRQRY | 132 |
| 129 | APEKPEEDASPEETQRYYTALRHYYNWLTRQRY | 133 |
| 130 | APEKPEEDTSAEELQRYYVSLRHYYNWLTRQRY | 134 |
| 131 | APEKAEEDASPEELQRYYVELRHYYNWLTRQRY | 135 |
| 132 | APEKPEEDASPEELQKYYVTLRHYYNWLTRQRY | 136 |
| 133 | APEKPEEDASPEEVQRYYVELRHYYNWLTRQRY | 137 |
| 134 | APEKPEEDASPEEIQRYYTELRHYYNWLTRQRY | 138 |
| 135 | APEKPEADASPEELQRYYVELRHYYNWLTRQRY | 139 |
| 136 | APEKPEADSSPEELQRYYVSLRHYYNWLTRQRY | 140 |
| 137 | APEKPEEDASPEELQRYYVSLRHYYNWITRQRY | 141 |
| 138 | APAKPEEDASPEELQQYYVSLRHYYNWLTRQRY | 142 |
| 139 | APEKPEEESSPEELQRYYVSLRHYYNWLTRQRY | 143 |
| 140 | APEKPGEDASPEELEQYYVSLRHYYNWLTRQRY | 144 |
| 141 | APEKPEEAASPEELQRYYVSARHYYNWLTRQRY | 145 |
| 142 | APEKPPEASPEELQRYYVSLRHYYNWLTRQRY | 146 |
| 143 | APEKPEEDATPEELQRYYVALRHYYNWLTRQRY | 147 |
| 144 | APEKAEEDASPEELQQYYVSLRHYYNWLTRQRY | 148 |
| 145 | APEKPEEDSSPEEIQRYYVSLRHYYNWLTRQRY | 149 |
| 146 | APEKPEEEASPEELQRYYVSTRHYYNWLTRQRY | 150 |
| 147 | APEKPEEDASPEETQKYYVSLRHYYNWLTRQRY | 151 |
| 148 | APEKPEEDAPAEELQRYYVSLRHYYNWLTRQRY | 152 |
| 149 | APEKPEEASPEELQRYYVELRHYYNWLTRQRY | 153 |
| 150 | APEKPEEDAEPEELQKYYVSLRHYYNWLTRQRY | 154 |
| 151 | APEKPEAEASPEELQRYYVSLRHYYNWLTRQRY | 155 |
| 152 | APEKAEEDASPEEIQRYYVSLRHYYNWLTRQRY | 156 |
| 153 | APEKVEEEASPEELQRYYVSLRHYYNWLTRQRY | 157 |
| 154 | APEKPEEEASPEELQRYEVSLRHYYNWLTRQRY | 158 |
| 155 | APEKPEEDASPEETQRYYVSLRHYYNWLTRQRY | 159 |
| 156 | APEKPEEDASEEELEQYYVSLRHYYNWLTRQRY | 160 |
| 157 | APAKPEEDASPEETQRYYVSLRHYYNWLTRQRY | 161 |
| 158 | APEKPEEDASPEELQRYYVSLRHYWNYLTRQRY | 162 |
| 159 | APEKPEADASPEELEQYYVSLRHYYNWLTRQRY | 163 |
| 160 | APEKPEADAEPEELQRYYTSLRHYYNWLTRQRY | 164 |
| 161 | APEKPEEDATPEELQQYYVSLRHYYNWLTRQRY | 165 |
| 162 | APEKPEEDASPEELQRYEVSLRAYYNWLTRQRY | 166 |
| 163 | APEKPEEAASPEELQRYYVALRHYYNWLTRQRY | 167 |
| 164 | APEKPEEDASEEELQEYYVSLRHYYNWLTRQRY | 168 |
| 165 | APEKPEEDASPEELQRYQVSLRHYYNWLTRQRY | 169 |
| 166 | APEKPPADASPEELQRYYVELRHYYNWLTRQRY | 170 |
| 167 | APEKPEEDASPEELQQYEVSLRHYYNWLTRQRY | 171 |
| 168 | APEKPEEDAEPEELQRYYVSLRHYYNWITRQRY | 172 |
| 169 | APEKPEEEASPEELQRYYVALRHYYNWLTRQRY | 173 |
| 170 | APEKPEEEASPEELEQYYVSLRHYYNWLTRQRY | 174 |
| 171 | APEKPEEDATPEEIQRYYVSLRHYYNWLTRQRY | 175 |
| 172 | APEKPEEDAEPEELQRYYVALRHYYNWLTRQRY | 176 |
| 173 | APAKPEEDASPEELQRYYVELRHYYNWLTRQRY | 177 |
| 174 | APAKPEEDAEPEELQRYYVSLRHYYNWLTRQRY | 178 |
| 175 | APEKPEEDAAPEELQRYYVALRHYYNWLTRQRY | 179 |
| 176 | APEKPEEDASEEELQRYYVSLRHYYNWLTRQRY | 180 |
| 177 | APEKPEEDSSPEELQRYYVELRHYYNWLTRQRY | 181 |
| 178 | APEKPEEDATPEETERYYVSLRHYYNWLTRQRY | 182 |
| 179 | APAKPEEDASPAELQRYYVSLRHYYNWLTRQRY | 183 |
| 180 | APEKPEEDASPEETQQYYVSLRHYYNWLTRQRY | 184 |
| 181 | APEKPEADASPEELQRYYVALRHYYNWLTRQRY | 185 |
| 182 | APEKPEEDGSPEELQRYYVELRHYYNWLTRQRY | 186 |
| 183 | APEKPPEDASPEELQRYYVSLRHYYNWLTRQRY | 187 |
| 184 | APEKPEEAASPEELQRYYVTLRHYYNWLTRQRY | 188 |
| 185 | APEKPEEEASPEELQRYYVELRHYYNWLTRQRY | 189 |
| 186 | APEKPEEDASAEELQRYYVELRHYYNWLTRQRY | 190 |
| 187 | APEKPEEDASPEELQRYYVSLRHQYNWLTRQRY | 191 |
| 188 | APEKPEEDAEPEELQRYYVSLRHYYNWLTRQRY | 192 |
| 189 | APEKPEEDASEALQRYYVSLRHYYNWLTRQRY | 193 |
| 190 | APEKPEEEAPPEELQRYYVSLRHYYNWLTRQRY | 194 |
| 191 | APEKPEEDASPEELQRYYISLRHYYNWLTRQRY | 195 |
| 192 | APEKPEEDAPAELQRYYVSLRHYYNWLTRQRY | 196 |
| 193 | APEKPEEDASEEIQRYYVSLRHYYNWLTRQRY | 197 |
| 194 | AHypEKPEEDASPEELQRYYVSLRHYYNWTLRQRY | 198 |
| 195 | APEKPEEDASPEALQRYYVELRHYYNWLTRQRY | 199 |

TABLE 1-continued

| Compound | Sequence | SEQ ID NO |
|---|---|---|
| 196 | APAKPPEDAEPEELQRYYVSLRHYYNWLTRQRY | 200 |
| 197 | APAKPEADASPEELQRYYVELRHYYNWLTRQRY | 201 |
| 198 | APEKPEEDAEPEALQRYYVSLRHYYNWLTRQRY | 202 |
| 199 | APEKPEEDAEPEETQRYYVSLRHYYNWLTRQRY | 203 |
| 200 | APEKHypEEDASPEELQRYYVSLRHYYNWLTRQRY | 204 |
| 201 | APEKPQEDAEPEELQEYYVSLRHYYNWLTRQRY | 205 |
| 202 | APEKPEEDAAPEELQKYYVSLRHYYNWLTRQRY | 206 |
| 203 | APAKPEEDASPEELQRYYVSLRHYYNWLTRQRY | 207 |
| 204 | APEKPEEEASPEEVQRYYVSLRHYYNWLTRQRY | 208 |
| 205 | APEKPEEEASPEELQKYYVSLRHYYNWLTRQRY | 209 |
| 206 | APEKPEEDASPEELEQYEVSLRHYYNWLTRQRY | 210 |
| 207 | APAKPEADAEPEELQRYYVSLRHYYNWLTRQRY | 211 |
| 208 | APEKPEEDASEEETQRYYVSLRHYYNWLTRQRY | 212 |
| 209 | APEKPEEDSEPEELQRYYVSLRHYYNWLTRQRY | 213 |
| 210 | APEKIEEEASPEELQRYYVSLRHYYNWLTRQRY | 214 |
| 211 | APEKPEEDATAEELQRYYVSLRHYYNWLTRQRY | 215 |
| 212 | APEKPEEDTAPEELQRYYVSLRHYYNWLTRQRY | 216 |
| 213 | APEKPEEETSPEELQRYYVSLRHYYNWLTRQRY | 217 |
| 214 | APEKPEEDASEEELQRYYVALRHYYNWLTRQRY | 218 |
| 215 | APEKPEEDASPAELQRYYVELRHYYNWLTRQRY | 219 |
| 216 | APAKPEEDASPEELEQYYVSLRHYYNWLTRQRY | 220 |
| 217 | APEKPEEDASPAELQRYYVALRHYYNWLTRQRY | 221 |
| 218 | APEKPEEDSSPEELQRYYVALRHYYNWLTRQRY | 222 |
| 219 | APEKPEEEAAPEELQRYYVSLRHYYNWLTRQRY | 223 |
| 220 | APEKPEEEAASAEELQRYYVSLRHYYNWLTRQRY | 224 |
| 221 | APEKPEEDAPEELQRYYVSLRHYYNWLTRQRY | 225 |
| 222 | APEKPEEDASAEELQQYYVSLRHYYNWLTRQRY | 226 |
| 223 | APEKPEEEAAEPEELQRYYVSLRHYYNWLTRQRY | 227 |
| 224 | APEKPGEEASPEELEQYYVSLRHYYNWLTRQRY | 228 |
| 225 | APEKPGEDAEPEELEQYYVSLRHYYNWLTRQRY | 229 |
| 226 | APEKPEEAASPEETQRYYVSLRHYYNWLTRQRY | 230 |
| 227 | APEKAEEDASPEELEQYYVSLRHYYNWLTRQRY | 231 |
| 228 | APEKPEEDASPEELQQYYVSLRAYYNWLTRQRY | 232 |
| 229 | APEKPEEDASPEELQRYYVSARHYYNWLTRQRY | 233 |
| 230 | APEKPEEDASPEEIQRYYVALRHYYNWLTRQRY | 234 |
| 231 | APEKPEEDATPEELQKYYVSLRHYYNWLTRQRY | 235 |
| 232 | APAKPPEDASPEELQRYYVELRHYYNWLTRQRY | 236 |
| 233 | APEKPEEAASPEELQQYYVSLRHYYNWLTRQRY | 237 |
| 234 | APAKPEEEASPEELQRYYVSLRHYYNWLTRQRY | 238 |
| 235 | APEKPEEDASHypEELQRYYVSLRHYYNWLTRQRY | 239 |
| 236 | APEKPEEEAPAEELQRYYVSLRHYYNWLTRQRY | 240 |
| 237 | APEKPEEDASPEELQRYYVEVRHYYNWLTRQRY | 241 |
| 238 | APEKTEEEASPEELQRYYVSLRHYYNWLTRQRY | 242 |
| 239 | APEKPEEDASEEELQRYEVSLRHYYNWLTRQRY | 243 |
| 240 | APEKPEEDASPEALQRYYVSLRHYYNWLTRQRY | 244 |
| 241 | APEKPEEEASPEEIQRYYVSLRHYYNWLTRQRY | 245 |
| 242 | APEKPEADASAEELQRYYVSLRHYYNWLTRQRY | 246 |
| 243 | APEKPEEEASPEELQQYYVSLRHYYNWLTRQRY | 247 |
| 244 | APEKPEEDAEPAELQRYYVSLRHYYNWLTRQRY | 248 | and wherein a half-life extending group is attached to the epsilon amino group of the lysine at position 7 or of a lysine at positions 6, 10, 11, 14, 17, 21 or 22, or to the carboxylic acid group of the side chain of an aspartate or a glutamate at position 14.

In an embodiment of the present invention, the PYY analogue is a compound having the formula:

$$R^1\text{—}Z\text{—}R^2,$$

wherein $R^1$ and $R^2$ are as defined above;

Z is an amino acid sequence of selected from Table 1; and wherein a half-life extending group is attached to the epsilon amino group of the lysine at position 7 and consists of a lipophilic substituent X and a linker U, wherein the linker U is attached to the amino acid side chain and X is attached to U, and the linker U consists of one, two or three sub-moieties (U1, U2, U3).

In some embodiments, the lipophilic substituent, X is selected from the group consisting of 15-carboxy-pentadecanoyl, 17-carboxy-heptadecanoyl (C18DA) and 19-carboxy-nonadecanoyl.

In some embodiments the linker U consists of one, two or three sub-moieties ($U^1$, $U^2$, $U^3$) independently selected from the group consisting of Gly, Glu, γ-Glu, ε-Lys, Ser and OEG, or independently selected from the group consisting of γ-Glu and OEG.

In certain embodiments, the linker U is selected from the group consisting of γ-Glu, γ-Glu-γ-Glu, γ-Glu-OEG, OEG-OEG, γ-Glu-γ-Glu-OEG, γ-Glu-OEG-OEG.

In specific embodiments, the half-life extending group is C18DA-γ-Glu-OEG-OEG-, i.e.

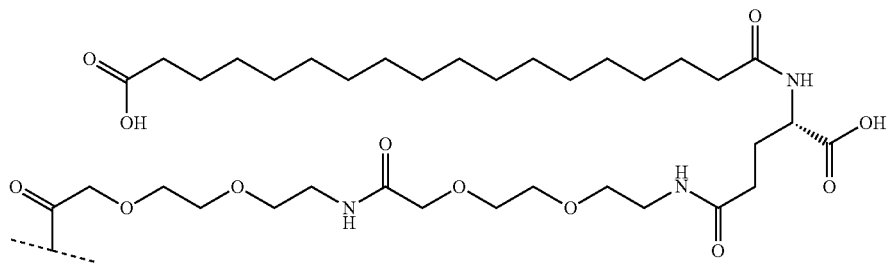

In some embodiments of the present invention, the PYY analogue is a compound selected from the group consisting of compound 1 to compound 244 as defined below.

In some embodiments, the PYY analogue has a maximum of 15 amino acid modifications as compared to hPYY(3-36).

In some embodiments, the PYY analogue has a maximum of 14 amino acid modifications as compared to hPYY(3-36).

In some embodiments, the PYY analogue has a maximum of 13 amino acid modifications as compared to hPYY(3-36).

In some embodiments, the PYY analogue has a maximum of 12 amino acid modifications as compared to hPYY(3-36).

In some embodiments, the PYY analogue has a maximum of 11 amino acid modifications as compared to hPYY(3-36).

In some embodiments, the PYY analogue has between 7 and 15 (i.e. 7, 8, 9, 10, 11, 12, 13, 14 or 15) amino acid modifications as compared to hPYY(3-36).

In some embodiments, the PYY analogue has between 8 and 14 (i.e. 8, 9, 10, 11, 12, 13 or 14) amino acid modifications as compared to hPYY(3-36).

In some embodiments, the PYY analogue has between 5 and 13 (i.e. 5, 6, 7, 8, 9, 10, 11, 12 or 13) amino acid modifications as compared to hPYY(3-36).

In some embodiments, the PYY analogue has between 7 and 13 (i.e. 7, 8, 9, 10, 11, 12 or 13) amino acid modifications as compared to hPYY(3-36).

In some embodiments, the PYY analogue has between 8 and 13 (i.e. 8, 9, 10, 11, 12 or 13) amino acid modifications as compared to hPYY(3-36).

In some embodiments, the PYY analogue has between 9 and 13 (i.e. 9, 10, 11, 12 or 13) amino acid modifications as compared to hPYY(3-36).

In some embodiments, the PYY analogue has between 10 and 13 (i.e. 10, 11, 12 or 13) amino acid modifications as compared to hPYY(3-36).

In some embodiments, the PYY analogue has between 8 and 12 (i.e. 8, 9, 10, 11 or 12) amino acid modifications as compared to hPYY(3-36).

In some embodiments, the PYY analogue has between 9 and 12 (i.e. 9, 10, 11 or 12) amino acid modifications as compared to hPYY(3-36).

In some embodiments, the PYY analogue has between 10 and 12 (i.e. 10, 11 or 12) amino acid modifications as compared to hPYY(3-36).

In some embodiments, the PYY analogue has between 9 and 11 (i.e. 9, 10 or 11) amino acid modifications as compared to hPYY(3-36).

In some embodiments, the PYY analogue has between 11 and 12 (i.e. 11 or 12) amino acid modifications as compared to hPYY(3-36).

In some embodiments, the PYY analogue or compound of the above-mentioned embodiments is in the form of a salt, preferably in the form of a pharmaceutically acceptable salt.

The PYY analogues of the invention are able to bind to the human NPY2 receptor (hNPY2-R).

Binding to biological receptors can be measured by appropriate assays known in the art. For instance, binding of PYY analogues to the NPY2 receptor can be evaluated by radio-ligand binding competition assays, e.g. as described in Example 1, below.

In some embodiments of compounds of the present invention, the binding affinity (Ki) towards hNPY2 receptor is below 100 nM (e.g. 0.01 to 100 nM).

In some embodiments of compounds of the present invention, the binding affinity (Ki) towards hNPY2 receptor is below 50 nM (e.g. 0.01 to 50 nM).

In some embodiments of compounds of the present invention, the binding affinity (Ki) towards hNPY2 receptor is below 10 nM (e.g. 0.01 to 10 nM).

In some embodiments of compounds of the present invention, the binding affinity (Ki) towards hNPY2 receptor is below 5 nM (e.g. 0.01 to 5 nM).

In some embodiments of compounds of the present invention, the binding affinity (Ki) towards hNPY2 receptor is below 2 nM (e.g. 0.01 to 2 nM).

The PYY analogues of the invention activate the human NPY2 receptor, i.e. they are NPY2 agonists.

In general, it is preferred to use a biological assay which measures intracellular signalling caused by binding of the compound to the relevant receptor. Activation of the NPY2 receptor by compounds of the invention (which behave as agonists of the receptor) reduces cAMP concentrations effecting intracellular signalling pathways. Thus, reduction of cAMP or any other suitable parameter in cells expressing the receptor can be used to monitor agonist activity towards the receptor. The skilled person will be aware of suitable assay formats, and examples are provided below.

$EC_{50}$ values may be used as a numerical measure of agonist potency at a given receptor. An $EC_{50}$ value is a measure of the concentration of a compound required to achieve half of that compound's maximal activity in a particular assay, e.g. in the assay as described in Example 2, below.

In some embodiments of compounds of the present invention, the $EC_{50}$ towards hNPY2 receptor is below 100 nM (e.g. 0.001 to 100 nM).

In some embodiments of compounds of the present invention, the $EC_{50}$ towards hNPY2 receptor is below 50 nM (e.g. 0.001 to 50 nM).

In some embodiments of compounds of the present invention, the $EC_{50}$ towards hNPY2 receptor is below 10 nM (e.g. 0.001 to 10 nM).

In some embodiments of compounds of the present invention, the $EC_{50}$ towards hNPY2 receptor is below 5 nM (e.g. 0.001 to 5 nM).

In some embodiments of compounds of the present invention, the $EC_{50}$ towards hNPY2 receptor is below 2 nM (e.g. 0.001 to 2 nM).

As mentioned above the PYY analogues or compounds of the present invention are generally soluble around pH 7 and 6. There are several techniques known to the skilled person in the art how to determine solubility. One such experiment is described below under Example 3. If specific solubility in mg/ml is provided herein, it is referred to the solubility determination as in Example 3.

In some embodiments, the solubility of the PYY analogues or compounds of the invention is greater than 1.0 mg/ml around pH 6 (e.g. at pH 6.1±0.2).

In some embodiments, the solubility of the PYY analogues or compounds of the invention is greater than 3.0 mg/ml around pH 6 (e.g. at pH 6.1±0.2).

In some embodiments, the solubility of the PYY analogues or compounds of the invention is greater than 5.0 mg/ml around pH 6 (e.g. at pH 6.1±0.2).

In some embodiments, the solubility of the PYY analogues or compounds of the invention is equal to or greater than 7.0 mg/ml around pH 6 (e.g. at pH 6.1±0.2).

In some embodiments, the solubility of the PYY analogues or compounds of the invention is equal to or greater than 8.0 mg/ml around pH 6 (e.g. at pH 6.1±0.2).

In some embodiments, the solubility of the PYY analogues or compounds of the invention is greater than 1.0 mg/ml around pH 7 (e.g. at pH 6.8±0.2).

In some embodiments, the solubility of the PYY analogues or compounds of the invention is greater than 5.0 mg/ml around pH 7 (e.g. at pH 6.8±0.2).

In some embodiments, the solubility of the PYY analogues or compounds of the invention is greater than 7.0 mg/ml around pH 7 (e.g. at pH 6.8±0.2).

In some embodiments, the solubility of the PYY analogues or compounds of the invention is equal to or greater than 8.0 mg/ml around pH 7 (e.g. at pH 6.8±0.2).

In some embodiments, the solubility of the PYY analogues or compounds of the invention is greater than 1.0 mg/ml around pH 6 (e.g. at pH 6.1±0.2) and around pH 7 (e.g. at pH 6.8±0.2).

In some embodiments, the solubility of the PYY analogues or compounds of the invention is greater than 3.0 mg/ml around pH 6 (e.g. at pH 6.1±0.2) and around pH 7 (e.g. at pH 6.8±0.2).

In some embodiments, the solubility of the PYY analogues or compounds of the invention is greater than 5.0 mg/ml around pH 6 (e.g. at pH 6.1±0.2) and around pH 7 (e.g. at pH 6.8±0.2).

In some embodiments, the solubility of the PYY analogues or compounds of the invention is greater than 6.0 mg/ml around pH 6 (e.g. at pH 6.1±0.2) and around pH 7 (e.g. at pH 6.8±0.2).

In some embodiments the PYY analogues or compounds of the invention have favourable pharmacokinetic properties. In this regard, in some embodiments of the invention, the in-vivo half-life of the PYY analogues or compounds is at least 3 hours in the mouse (NMRI mice, see measurement described in Example 5). In some embodiments, the in-vivo half-life is at least 5 hours in the mouse. In some embodiments, the in-vivo half-life is at least 7 hours in the mouse. In some embodiments, the in-vivo half-life is at least 10 hours in the mouse.

The invention further provides a composition comprising a PYY analogue as described above. The composition may be a pharmaceutical composition, and may comprise a pharmaceutically acceptable carrier, excipient or vehicle.

The invention further provides a method for the synthesis of a PYY analogue as described above. The method may comprise the steps of synthesising the peptide by solid-phase or liquid-phase methodology, and optionally isolating and/or purifying the final product.

Method of Treatment

The present invention is directed to PYY analogues or a compound according to the above-mentioned embodiments, which are useful in the prevention and/or treatment of a disease and/or condition associated with or modulated by NPY2 receptor activity, including but not limited to the treatment and/or prevention of obesity and various obesity-related conditions, diseases, or co-morbidities, such as type 2 diabetes and NASH (non-alcoholic steatohepatitis).

The compounds described herein find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, and may have a beneficial effect on glucose control and/or on circulating cholesterol levels, being capable of lowering circulating LDL levels and increasing HDL/LDL ratio. Thus, the compounds of the invention can be used for direct or indirect therapy of any condition caused or characterised by excess body weight, such as the treatment and/or prevention of obesity, morbid obesity, obesity linked inflammation, obesity linked gallbladder disease, and obesity related sleep apnea. They may also be used for the prevention of conditions or treatment of obesity associated co-comorbidities caused or characterised by inadequate glucose control or dyslipidaemia (e.g. elevated LDL levels or reduced HDL/LDL ratio), Type 2 diabetes, metabolic syndrome, hypertension, atherogenic dyslipidemia, and cardiovascular diseases such as atherosclerosis, coronary heart disease, peripheral artery disease, stroke or microvascular disease, and cancer. Their effects in these conditions may be as a result of or associated with their effect on body weight, or may be independent thereof.

As mentioned above the PYY analogues or compounds according to the above mentioned embodiments are useful in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or co-morbidities, such as type 2 diabetes, hypertension, dyslipidemia, sleep apnea, cardiovascular disease, hepatic steatosis, non-alcoholic fatty liver disease (NAFLD), non-alcoholic steatohepatitis (NASH) and cancer. The subject may be affected by obesity accompanied by at least one weight-related co-morbid condition, such as type 2 diabetes, hypertension, dyslipidemia, sleep apnea, cardiovascular disease, hepatic steatosis, NAFLD and NASH. It will be understood that the PYY analogues may thus be administered to subjects affected by conditions characterised by inadequate control of appetite or otherwise over-feeding, such as binge-eating disorder and Prader-Willi syndrome. It will be clear that the analogues can be used for treatment of combinations of the conditions described.

Thus, the invention provides a PYY analogue for use in a method of medical treatment, e.g. for treating, inhibiting or reducing weight gain, promoting weight loss and/or reducing excess body weight. Treatment may be achieved, for example, by control of appetite, feeding, food intake, caloric intake and/or energy expenditure.

The invention also provides a PYY analogue of the invention for use in a method of treating obesity as well as associated diseases, disorders and health conditions, including, but not limited to, morbid obesity, obesity prior to surgery, obesity-linked inflammation, obesity-linked gallbladder disease and obesity related sleep apnea and respiratory problems, degeneration of cartilage, osteoarthritis, and reproductive health complications of obesity or overweight such as infertility. The subject may be affected by obesity accompanied by at least one weight-related co-morbidity, such as type 2 diabetes, hypertension, dyslipidemia, sleep apnea, cardiovascular disease, cancer, hepatic steatosis, NAFLD and NASH.

The invention also provides a PYY analogue of the invention for use in a method of prevention or treatment of conditions mentioned above.

Accordingly, the present invention relates to a PYY analogue or a compound according to the above-mentioned embodiments for use as a medicament.

Furthermore, the present invention relates to the use of a PYY analogue or a compound according to the above-mentioned embodiments for the treatment and/or prevention of a disease and/or condition associated with or modulated by NPY2 receptor activation. Furthermore, the present invention relates to the use of a PYY analogue or a compound according to the above mentioned embodiments for the treatment and/or prevention of obesity and various obesity-related conditions, diseases, or co-morbidities, such as type 2 diabetes and NASH (non-alcoholic steatohepatitis) and others as mentioned above.

In a further aspect the present invention relates to the use of a PYY analogue or a compound according to the above mentioned embodiments for the preparation of a medicament for the treatment and/or prevention of above-mentioned diseases and conditions.

In a further aspect the present invention relates to methods for the treatment or prevention of above mentioned diseases and conditions, which method comprises the administration of an effective amount of a PYY analogue or a compound according to the above-mentioned embodiments to a human being.

The dose range of the compounds of general formula 1 applicable per week is usually from 0.01 to 100 mg for humans (subcutaneous administration).

The actual pharmaceutically effective amount or therapeutic dosage will usually depend on factors known by those skilled in the art such as age and weight of the patient, route of administration and severity of disease. In any case, the compounds will be administered at dosages and in a manner, which allows a pharmaceutically effective amount to be delivered based upon patient's unique condition.

Combination Therapy

A PYY analogue of the invention may be administered as part of a combination therapy together with another active agent for the treatment of the disease or disorder in question, e.g. an anti-obesity agent, an anti-diabetic agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus, a peptide of the invention may be used in combination with an anti-obesity agent of known type. The anti-obesity agent may be a GIP or GLP-1 receptor agonist (including GLP-1 or a GLP-1 analogue, exendin-4 or an exendin-4 analogue, any other GLP-1 receptor agonist including Liraglutide (Saxenda™), Semaglutide, Dulaglutide, Albiglutide, MK-8521, or a glucagon-GLP-1 dual agonist (e.g. HM-12525, SAR-425899, MEDI-0382, NN-9277 or as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802, WO2016/166289), oxyntomodulin or an oxyntomodulin analog (e.g. TT-401) or a GLP-1/GIP dual agonist (e.g. Tirzepatide or as described in WO2013/164483), or a GLP-1/GIP/glucagon triple agonists (e.g. NN-9423 or as described in WO2015/067716, WO2016/198624, WO2017/116204, WO2017/116205, WO2018/100134, WO2018/100135).

The anti-obesity agent may be amylin or an amylin analogue, e.g. pramlintide, NN-9838, or an amylin (or calcitonin) analogue disclosed in WO2012/168430, WO2012/168431, WO2012/168432, WO2015/040182, WO2015/071229, WO2016/146739, WO2018/046719, or WO2018/172390.

Alternatively, the anti-obesity agent may be Orlistat™, Sibutramine™, phentermine, a melanin concentrating hormone receptor 1 antagonist, CCK, leptin analogue, a GOAT inhibitor, a ghrelin-receptor antagonist, a further neuropeptide Y (NPY) analogue, a NPY4 receptor agonist, a NPY5 receptor antagonist, a cannabinoid receptor 1 antagonist, a beta-3 agonist, a lipase inhibitor, Human proIslet Peptide (HIP), a melanocortin receptor 4 agonist, as well as analogues thereof.

Moreover, a peptide of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including Liraglutide (Victoza™), Semaglutide, Dulaglutide, Albiglutide, MK-8521, or a glucagon-GLP-1 dual agonist (e.g. HM-12525, SAR-425899, MEDI-0382, NN-9277 or as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195, WO2015/055801, WO2015/055802, WO2016/166289), oxyntomodulin, or an oxyntomodulin analog (e.g. TT-401), or a SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™ Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, and lixisenatide (Lyxumia™)

According to more specific embodiments, the PYY analogue of the present invention is administered as part of a combination therapy together with a GLP-1 receptor agonist selected from the group consisting of Liraglutide, Semaglutide, Dulaglutide and Albiglutide or a glucagon-GLP-1 dual agonist described in WO2011/006497, WO2014/041195, WO2015/055801, WO2015/055802, WO2016/166289 or an amylin receptor agonist selected from the group consisting of pramlintide or an amylin analogue disclosed in WO2012/168430, WO2012/168431, WO2012/168432, WO2015/040182, WO2016/146739, or WO2018/046719.

A peptide of the invention may further be used in combination with medications targeting cardiovascular diseases treating hypertension, dyslipidemia, inflammation and platelet function. The medication treating hypertension can be selected from the group including, but not limited to, an angiotensin-converting enzyme inhibitor, an angiotensin II receptor blocker, a diuretic, a beta-blocker or a calcium channel blocker.

A peptide of the invention may still further be used in combination with an anti-dyslipidemia agent of known type, including, but not limited to, a statin, a fibrate, a niacin, a PSCK9 (Proprotein convertase subtilisin/kexin type 9) inhibitor, or a cholesterol absorption inhibitor.

A peptide of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™ Lansoprazole™, Dexlansoprazole™, Esomeprazole™, Pantoprazole™, Rabeprazole™ Zolpidem™, Alpidem™, Saripidem™ or Necopidem™.

In addition, with regard to anti-inflammatory treatment, a peptide of the invention may be beneficial if administered in combination with an anti-inflammatory agent of known type, including, but not limited to:
  steroids and corticosteroids, such as beclomethasone, methylprednisolone, betamethasone, prednisone, dexamethasone, and hydrocortisone;
  non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);
  COX II inhibitors, such as rofecoxib and celecoxib;
  preparations of interferon beta (e.g. interferon beta-la or interferon beta-1b);
  and certain other compounds, such as 5-aminosalicylic acid and prodrugs and pharmaceutically acceptable salts thereof.

Preparation
General Procedure for Solid Phase Synthesis of Peptides

All peptides were synthesized by standard Fmoc-based solid phase peptide chemistry on a Tentagel S RAM resin (loading 0.23-0.25 mmol/g, bead size 90 μm) supplied by Iris Biotech GmbH or Rapp Polymere GmbH.

The following protected amino acids were used: Fmoc-Ala-OH, Fmoc-Arg(Pbf)-OH, Fmoc-Asn(Trt)-OH, Fmoc-Asp(tBu)-OH, Fmoc-Gln(Trt)-OH, Fmoc-Glu(tBu)-OH, Fmoc-Glu-OtBu, Fmoc-Gly-OH, Fmoc-His(Trt)-OH, Fmoc-Ile-OH, Fmoc-Leu-OH, Fmoc-Lys(Boc)-OH, Fmoc-Lys(Dde)-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH. The L-form of the amino acid building blocks was utilized if not specified otherwise. The modular half-life extending group was built up by solid-phase peptide synthesis (SPPS) using protected building blocks such as, but not limited to, 18-(tert-butoxy)-18-oxooctadecanoic acid (C18DA(tBu)), 2-[2-[2-[[2-[2-[2-(9H-fluoren-9-ylmethoxycarbonyl-amino)ethoxy]ethoxy]acetyl]amino]ethoxy]ethoxy]acetic acid (Fmoc-OEG-OEG-OH), 2-[2-[2-(9H-fluoren-9-ylmethoxycarbonylamino)ethoxy]ethoxy] acetic acid (Fmoc-OEG-OH) and Fmoc-Glu-OtBu.

The amino acids, Fmoc-Glu-OtBu, Oxyma and DIC, were purchased from standard suppliers, e.g. Bachem, Novabiochem, ABCR, Iris Biotech GmbH, Sigma-Aldrich. 18-(Tert-butoxy)-18-oxooctadecanoic acid (C18DA(tBu)) was supplied by Cool Pharm Ltd. or AstraTech, 2-[2-[2-[[2-[2-[2-(9H-Fluoren-9-ylmethoxycarbonyl-amino)ethoxy]ethoxy]acetyl]amino]ethoxy]ethoxy]acetic acid (Fmoc-OEG-OEG-OH) was supplied by ABCR GmbH & CO. KG or Iris Biotech GmbH, 2-[2-[2-(9H-fluoren-9-ylmethoxycarbonylamino)ethoxy]ethoxy] acetic acid (Fmoc-OEG-OH) was supplied by Combi Blocks Inc., Iris Biotech GmbH or Hangzhou APIChem Technology Co., Ltd. 3-Methylbutanoic acid was supplied by Sigma-Aldrich GmbH.

Assembly of peptides started from the C-terminus by stepwise chain elongation towards the N-terminus according to the respective sequences until the N-terminal capping group was reached. Deprotection of the side chain of the branching amino acid, e.g. Lys(Dde), was followed by assembly of the half-life extending group.

The PYY analogues were obtained as TFA salts from the cleavage/deprotection or from the HPLC purification. The trifluoroacetate can be exchanged by common procedures, such as resin-ion exchange procedures, e.g. as disclosed in Roux, St. et al. J. Pept. Sci. 2008; 14: 354-359.

Synthesis Method 1 (S01)

Peptides were synthesized by microwave-assisted solid-phase peptide synthesis (SPPS) on a CEM Liberty Blue Peptide Synthesizer at 0.25 mmol scale on Tentagel S RAM resin using the Fmoc strategy.

Standard coupling of amino acids was performed with 4 eq of suitably protected amino acid in DMF (0.2 mol/l, 5 ml), 4 eq of Oxyma in DMF (1 mol/l, 1 ml) and 8 eq DIC in DMF (1 mol/l, 2 ml) at 90° C. for 4 min. Fmoc-Arg(Pbf)-OH was coupled 2 times at 90° C. for 4 min, Fmoc-His(Trt)-OH was coupled 2 times at 50° C. for 12 min and Fmoc-Glu-OtBu was coupled 4 times at 50° C. for 12 min. Fmoc-OEG-OH, Fmoc-OEG-OEG-OH and C18DA(tBu) were coupled 2 times for 4 min at 90° C. Capping of the N-terminus was achieved by coupling 3-methylbutanoic acid 3 times at 90° C. for 4 min.

$N^\alpha$Fmoc deprotection was performed with 20% piperidine/DMF (10 ml) for 1 min at 90° C. Deprotection of the Lys(Dde)-group was carried out 2 times with 5% hydrazine hydrate in DMF (10 ml) for 3 min at 90° C.

Raw products were washed on resin with DCM and dried prior to cleavage. Cleavage from resin and deprotection was performed with a mixture of 95% TFA/water (10 ml) and triisopropylsilane (250 μl) for 40 min at 42° C. Crude peptides were precipitated with cold diethyl ether, dissolved in 50% acetonitrile/water and purified by preparative HPLC (P01).

Synthesis Method 2 (S02)

Peptides were synthesized by SPPS on a MultiSynTech SYRO II at 0.2 mmol scale.

Standard coupling of amino acids was achieved by using 4 eq of suitably protected amino acids dissolved in 0.5 mol/l Oxyma-DMF solution (0.5 mol/l, 1.6 ml) and 4.5 eq DIC (0.5 mol/l, 1.8 ml) in DMF. Fmoc-Phe-OH was dissolved in 0.5 mol/l Oxyma-NMP and 4 eq were used for coupling (0.5 mol/l, 1.6 ml).

Coupling time of the first 15 amino acids starting from the C-terminus was 2 h at RT. Subsequent couplings were realized by double coupling (2×2 h at RT). Capping of the N-terminus was achieved by coupling with 3-methylbutanoic acid (2×2 h at RT). Deprotection of Lys(Dde)-group was carried out selectively using 5% hydrazine in DMF (5×5 min at RT, 4 ml) followed by coupling of 4 eq Fmoc-OEG-OEG-OH (3×2 h at RT), 4 eq Fmoc-Glu-OtBu and 4 eq C18DA(tBu) (2×2 h at RT).

$N^\alpha$ Fmoc deprotections were performed using 40% piperidine in NMP (4 ml) for 3 min followed by 20% piperidine in NMP (4 ml) for 15 min at RT.

Peptides were cleaved from resin and side-chains deprotected by adding 15 ml 95:2:1:2 TFA:DODT:TES:water for 4 h at RT or 45 min at 45° C. The peptides were precipitated with cold diethyl ether, dissolved in acetonitrile/water and purified by preparative HPLC(P02).

Synthesis Method 3 (S03)

Peptides were synthesized using microwave-assisted SPPS on a Biotage Alstra Synthesizer at 0.2 mmol scale.

Standard coupling of amino acids was achieved by using 5 eq of suitably protected amino acid dissolved in 0.5 mol/l Oxyma-DMF solution (0.5 mol/l, 2 ml) and 5 eq DIC in DMF (0.5 mol/l, 2 ml). Coupling of the first 15 amino acids starting from the C-terminus was achieved by heating for 5 min to 75° C. Subsequent couplings were realized by double coupling (2×5 min at 75° C.).

$N^\alpha$ Fmoc deprotections were carried out using 20% piperidine in DMF for 30 sec followed by 20% piperidine for 3 min at 75° C.

Special conditions were used for: coupling of Fmoc-His (Trt)-OH (2×12 min at 50° C.) and subsequent Fmoc-deprotection at RT (20% piperidine in DMF for 3 min followed by 20% piperidine in DMF for 10 min); coupling of Fmoc-Glu-OtBu (2×6 min at 75° C.) and Fmoc-Arg(Pbf)-OH (2×5 min at 75° C.); coupling of Fmoc-Asp(tBu)-OH and subsequent Fmoc-deprotection at RT (20% piperidine in DMF for 3 min followed by 20% piperidine in DMF for 10 min); Dde deprotection with 5% hydrazine in DMF (5×5 min at RT); coupling of 4 eq Fmoc-OEG-OEG-OH (3×10 min at 75° C.) and 2.5 eq C18DA(tBu) (2×10 min at 75° C.).

Cleavage from resin and side-chain deprotection was performed by adding 8 ml 95:2:1:2 TFA:DODT:TES:water for 4 hours at RT or 45 min at 45° C. Crude peptides were precipitated with cold diethyl ether, dissolved in 50% acetonitrile/water and purified by preparative HPLC (P02).

Purification Method 1 (P01)

Crude peptides were purified by reversed phase chromatography using an Agilent preparative HPLC-MS System with preparative pumps G1361A, a diode array detector G1315B, a mass-spectrometer G1956B and a fraction collector CTC PAL IFC. A Waters XSelect CSH Prep C18 column (130 Å, 5 µm, OBD, 30 mm×150 mm) served as stationary phase. The mobile phase was run with a gradient of buffer A (0.1% TFA in $H_2O$) and buffer B (0.1% TFA in ACN, gradient: 20-42% over 44 min) at a flow rate of 50 ml/min at 40° C. The relevant fractions were pooled and lyophilized. The final product was characterized by analytical HPLC-MS (A01).

Purification Method 2 (P02)

Crude peptides were purified by reversed phase HPLC using a Waters preparative HPLC with C8 column (Reprosil Gold 200 Å, 5 µm, 40 mm×250 mm), preparative pumps (waters 2545), UV/VIS detector (Waters 2489) and a Waters fraction collector III. The mobile phase was run with a gradient of buffer A (0.1% TFA in $H_2O$) and buffer B (0.1% TFA in ACN, gradient: 35-45% B over 10 min) at a flow rate of 50 ml/min at RT. Relevant fractions were analysed, pooled and lyophilized. The final product was characterized by analytical UPLC-MS (A02).

Analytical Method 1 (A01)

Peptide purity and mass were determined by analytical HPLC-MS on a Kinetex C8 column (Phenomenex, 100 Å, 2.6 µm, 4.6 mm×150 mm) using a Waters Acquity HPLC System equipped with 3100 Mass Detector. Analysis was performed by gradient elution with buffer A (0.3% TFA in $H_2O$) and buffer B (0.24% TFA in ACN) at a temperature of 40° C. Details of the gradient and flow rates are summarized in the table below. Retention times and masses were recorded.

| Method | A01 | Gradient/ Solvent Time [min] | % Sol [Water 0.3% TFA (v/v)] | % Sol [ACN 0.24% TFA (v/v)] | Flow [ml/min] | Temp [° C.] |
|---|---|---|---|---|---|---|
| Device description: | Waters Acquity with 3100 MS | 0.0 | 65.0 | 35.0 | 0.5 | 40.0 |
| Column: | Kinetex C8_4.6 × 150 mm_2.6 µm | 15.0 | 45.0 | 55.0 | 0.5 | 40.0 |
| Column producer: | Phenomenex | 16.0 | 10.0 | 90.0 | 1.0 | 40.0 |
| | | 17.01 | 65.0 | 35.0 | 1.0 | 40.0 |
| | | 18.0 | 65.0 | 35.0 | 1.0 | 40.0 |

Analytical Method 2 (A02)

Analytical UPLC-MS was performed on a Waters Acquity class H using a Waters Acquity UPLC C18 column (peptide CSH™ 130A, 1.7 µm, 2.1 mm×100 mm) and a gradient flow of buffer C (0.3% TFA in $H_2O$) and buffer D (10% $H_2O$+ 0.3% TFA in ACN; 38-48% D over 14 min) connected to a SQ Detector 2 (ESI, Waters).

List of Abbreviations

ACN: acetonitrile
Boc: tert-butyloxycarbonyl
C18DA(tBu): 18-(tert-butoxy)-18-oxooctadecanoic acid
DPBS: Dulbecco's phosphate-buffered saline
DCM: dichloromethane
DIC: diisopropylcarbodiimide
DIPEA: diisopropylethylamine
Dde: (4,4-dimethyl-2,6-dioxocyclohex-1-ylidene)ethyl
DMF: N,N-dimethylformamid
DODT: 3,6-dioxa-1,8-octanedithiol
Fmoc: 9H-fluoren-9-ylmethoxycarbonyl
Fmoc-OEG-OH: 2-[2-[2-(9H-fluoren-9-ylmethoxycarbonylamino)ethoxy]ethoxy] acetic acid
Fmoc-OEG-OEG-OH: 2-[2-[2-[[2-[2-[2-(9H-fluoren-9-ylmethoxycarbonyl-amino)ethoxy]ethoxy]acetyl]amino]ethoxy]ethoxy]acetic acid
HTRF: homogeneous time resolved fluorescence
IBMX: 3-isobutyl-1-methylxanthine
iVal: 3-methylbutanoyl (isovalerianoyl)

MRT: mean residence time
NMP: 1-methyl-pyrrolidine-2-one
Oxyma: 2-cyano-2-(hydroxyimino)acetic acid ethyl ester
OEG: 2-[2-(2-aminoethoxy)ethoxy]acetic acid
Pbf: 2,2,4,6,7-pentamethyldihydrobenzofuran-5-sulfonyl
Rt: retention time
RT: room temperature
SPPS: solid-phase peptide synthesis
tBu: tert-butyl
Trt: trityl
TES: triethylsilane
TFA: trifluoroacetic acid The following compounds were synthesised. All compounds were obtained as TFA salts:

Compound 1

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13Q,18Q,19E,22V,28Y,30W,31L]hPYY(4-36) iVal-APEK (C18DA-gGlu-OEG1-OEG2-) PEEDAQPEELQEYYVSLRHYYNWLTRQRY-NH2 (sequence and structure below disclosed as SEQ ID NO: 5)

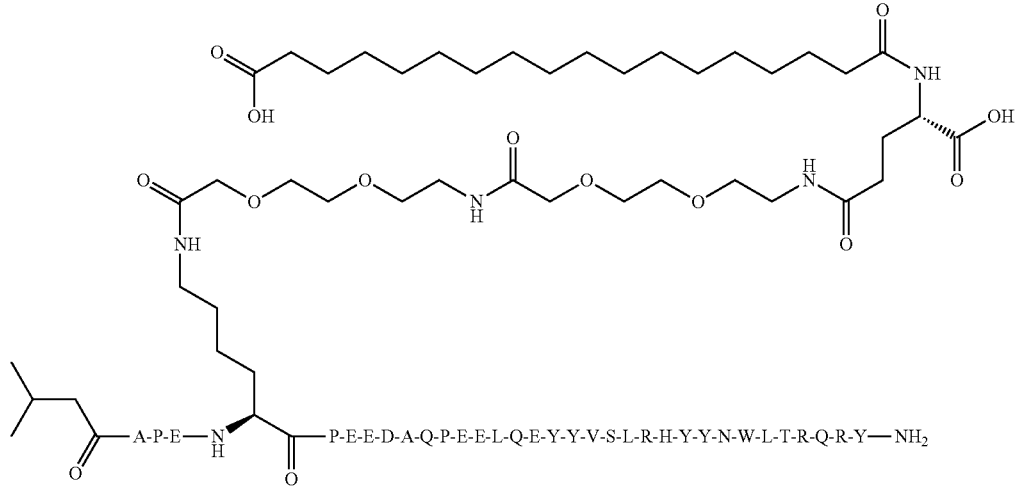

MW (calculated): 5001.6 Da
Synthesis and purification methods: S01; P01
LCMS: A01; Rt: 10.17 min; m/3: 1668.0 m/4: − m/5: -

Compound 2

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,5Hyp,7K,9E,18Q,22V,28Y,30W,31L]hPYY(4-36) iVal-AHypEK (C18DA-gGlu-OEG1-OEG2-) PEEDASPEELQRYYVSLRHYYNWLTRQRY-NH2 (SEQ ID NO: 6)

MW (calculated): 5003.6 Da
Synthesis and purification methods: S01; P01
LCMS: A01; Rt: 9.29 min; m/3: 1668.0 m/4: − m/5: -

Compound 3

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,15A,18Q,22V,28Y,30W,31L]hPYY(4-36) iVal-APEK (C18DA-gGlu-OEG1-OEG2-) PEEEASPAELQRYYVSLRHYYNWLTRQRY-NH2 (SEQ ID NO: 7)

MW (calculated): 4943.6 Da
Synthesis and purification methods: S01; P01
LCMS: A01; Rt: 9.86 min; m/3: − m/4: 1237.0 m/5: -

Compound 4

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,28Y,30W,31L,32Q]hPYY(4-36) iVal-APEK (C18DA-gGlu-OEG1-OEG2-) PEEDASPEELQRYYVSLRHYYNWLQRQRY-NH2 (SEQ ID NO: 8)

MW (calculated): 5014.6 Da
Synthesis and purification methods: S01; P01
LCMS: A01; Rt: 9.31 min; m/3: 1672.0 m/4: − m/5: -

Compound 5

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,12V,18Q,22V,28Y,30W,31L]hPYY(4-36) iVal-APEK (C18DA-gGlu-OEG1-OEG2-) PEEEVSPEELQRYYVSLRHYYNWLTRQRY-NH2 (SEQ ID NO: 9)

MW (calculated): 5029.7 Da
Synthesis and purification methods: S01; P01
LCMS: A01; Rt: 10.02 min; m/3: − m/4: 1258.0 m/5: -

Compound 6

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,18Q,22V,24A,28Y,30W,31L]hPYY(4-36) iVal-APEK(C18DA-gGlu-OEG1-OEG2-)PEEEASPEELQRYYVSARHYYNWLTRQRY-NH2 (SEQ ID NO: 10)

MW (calculated): 4959.6 Da
Synthesis and purification methods: S01; P01
LCMS: A01; Rt: 9.32 min; m/3: – m/4: 1241.0 m/5: -

Compound 7

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,19A,22V,28Y,30W,31L]hPYY(4-36) iVal-APEK(C18DA-gGlu-OEG1-OEG2-)PEEDASPEELQAYYVSLRHYYNWLTRQRY-NH2 (SEQ ID NO: 11)

MW (calculated): 4902.5 Da
Synthesis and purification methods: S01; P01
LCMS: A01; Rt: 10.00 min; m/3: – m/4: 1226.0 m/5: -

Compound 8

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,18Q,19Q,22V,28Y,30W,31L]hPYY(4-36) iVal-APEK(C18DA-gGlu-OEG1-OEG2-)PEEDASEEELQQYYVSLRHYYNWLTRQRY-NH2 (SEQ ID NO: 12)

MW (calculated): 4991.6 Da
Synthesis and purification methods: S02; P02
LCMS: A02; Rt: 12.75 min; m/3: 1665.3 m/4: 1248.9 m/5: 999.2

Compound 9

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17I,18Q,22V,23E,28Y,30W,31L]hPYY(4-36) iVal-APEK(C18DA-gGlu-OEG1-OEG2-)PEEDASPEEIQRYYVELRHYYNWLTRQRY-NH2 (SEQ ID NO: 13)

MW (calculated): 5029.6 Da
Synthesis and purification methods: S01; P01
LCMS: A01; Rt: 9.60 min; m/3: 1677.0 m/4: – m/5: -

Compound 10

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,17T,18Q,22V,28Y,30W,31L]hPYY(4-36) iVal-APEK(C18DA-gGlu-OEG1-OEG2-)PEADASPEETQRYYVSLRHYYNWLTRQRY-NH2 (SEQ ID NO: 14)

MW (calculated): 4917.5 Da
Synthesis and purification methods: S01; P01
LCMS: A01; Rt: 9.21 min; m/3: – m/4: 1230.0 m/5: -

Compound 11

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17I,18Q,19Q,22V,28Y,30W,31L]hPYY(4-36) iVal-APEK(C18DA-gGlu-OEG1-OEG2-)PEEDASPEEIQQYYVSLRHYYNWLTRQRY-NH2 (SEQ ID NO: 15)

MW (calculated): 4959.6 Da
Synthesis and purification methods: S01; P01
LCMS: A01; Rt: 9.79 min; m/3: – m/4: 1241.0 m/5: -

Compound 12

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13P,14G,18Q,22V,28Y,30W,31L]hPYY(4-36) iVal-APEK(C18DA-gGlu-OEG1-OEG2-)PEEDAPGEELQRYYVSLRHYYNWLTRQRY-NH2 (SEQ ID NO: 16)

MW (calculated): 4957.6 Da
Synthesis and purification methods: S01; P01
LCMS: A01; Rt: 10.87 min; m/3: – m/4: 1240.0 m/5: -

Compound 13

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,18Q,19Q,22V,28Y,30W,31L]hPYY(4-36) iVal-APEK(C18DA-gGlu-OEG1-OEG2-)PEEDAAPEELQQYYVSLRHYYNWLTRQRY-NH2 (SEQ ID NO: 17)

MW (calculated): 4943.6 Da
Synthesis and purification methods: S01; P01
LCMS: A01; Rt: 10.70 min; m/3: – m/4: 1237.0 m/5: -

Compound 14

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,13T,18Q,22V,28Y,30W,31L]hPYY(4-36) iVal-APEK(C18DA-gGlu-OEG1-OEG2-)PEADATPEELQRYYVSLRHYYNWLTRQRY-NH2 (sequence and structure below disclosed as SEQ ID NO: 18)

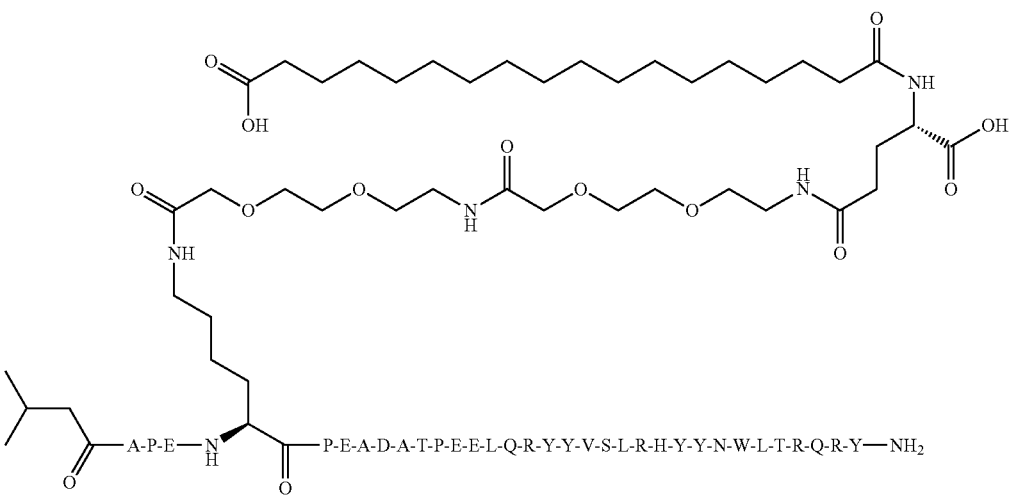

MW (calculated): 4943.6 Da
Synthesis and purification methods: S01; P01
LCMS: A01; Rt: 9.96 min; m/3: 1648.0 m/4: – m/5: -

Compound 15

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17I,18Q,21E,22V,28Y,30W,31L]hPYY(4-36) iVal-APEK(C18DA-gGlu-OEG1-OEG2-)PEEDASPEEIQRYEVSLRHYYNWLTRQRY-NH2 (SEQ ID NO: 19)

MW (calculated): 4953.5 Da
Synthesis and purification methods: S01; P01
LCMS: A01; Rt: 9.22 min; m/3: 1652.0 m/4: – m/5: -

Compound 16

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17T,18Q,22V,28Y,30W,31L]hPYY(4-36) iVal-APEK(C18DA-gGlu-OEG1-OEG2-)PEEDASPEETQRYYVTLRHYYNWLTRQRY-NH2 (SEQ ID NO: 20)

MW (calculated): 4989.6 Da
Synthesis and purification methods: S01; P01
LCMS: A01; Rt: 9.28 min; m/3: – m/4: 1248.0 m/5: -

Compound 17

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,15A,18Q,22V,28Y,30W,31L]hPYY(4-36) iVal-APEK(C18DA-gGlu-OEG1-OEG2-)PEEDASPAELQRYYVSLRHYYNWLTRQRY-NH2 (SEQ ID NO: 21)

MW (calculated): 4929.6 Da
Synthesis and purification methods: S01; P01
LCMS: A01; Rt: 9.77 min; m/3: 1643.0 m/4: – m/5: -

Compound 18

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,19Q,22V,28Y,30W,31L]hPYY(4-36) PEEDAEPEELQQYYVSLRHYYNWLTRQRY-NH2 (SEQ ID NO: 22)

MW (calculated): 5001.6 Da
Synthesis and purification methods: S01; P01
LCMS: A01; Rt: 10.27 min; m/3: – m/4: 1251.0 m/5: -

Compound 19

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,18Q,19Q,22V,28Y,30W,31L]hPYY(4-36) iVal-APEK (C18DA-gGlu-OEG1-OEG2-) PEADASPEELQQYYVSLRHYYNWLTRQRY-NH2 (SEQ ID NO: 23)

MW (calculated): 4901.5 Da
Synthesis and purification methods: S01; P01
LCMS: A01; Rt: 9.90 min; m/3: 1634.0 m/4: – m/5: -

Compound 20

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,18Q,22V,23E,28Y,30W,31L]hPYY(4-36) iVal-APEK (C18DA-gGlu-OEG1-OEG2-) PEEDAAPEELQRYYVELRHYYNWLTRQRY-NH2 (SEQ ID NO: 24)

MW (calculated): 5013.6 Da
Synthesis and purification methods: S01; P01
LCMS: A01; Rt: 10.72 min; m/3: – m/4: 1253.0 m/5: -

Compound 21

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,19K,22V,28Y,30W,31L]hPYY(4-36) iVal-APEK (C18DA-gGlu-OEG1-OEG2-) PEEDASPEELQKYYVSLRHYYNWLTRQRY-NH2 (SEQ ID NO: 25)

MW (calculated): 4959.6 Da
Synthesis and purification methods: S01; P01
LCMS: A01; Rt: 9.62 min; m/3: – m/4: 1241.0 m/5: -

Compound 22

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22T,18Q,22V,28Y,30W,31L]hPYY(4-36) iVal-APEK (C18DA-gGlu-OEG1-OEG2-) PEEDASPEELQRYYTSLRHYYNWLTRQRY-NH2 (SEQ ID NO: 26)

MW (calculated): 4989.6 Da
Synthesis and purification methods: S01; P01
LCMS: A01; Rt: 9.63 min; m/3: 1664.0 m/4: – m/5: -

Compound 23

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,17I,18Q,22V,28Y,30W,31L]hPYY(4-36) iVal-APAK (C18DA-gGlu-OEG1-OEG2-) PEEDASPEEIQRYYVSLRHYYNWLTRQRY-NH2 (sequence and structure below disclosed as SEQ ID NO: 27)

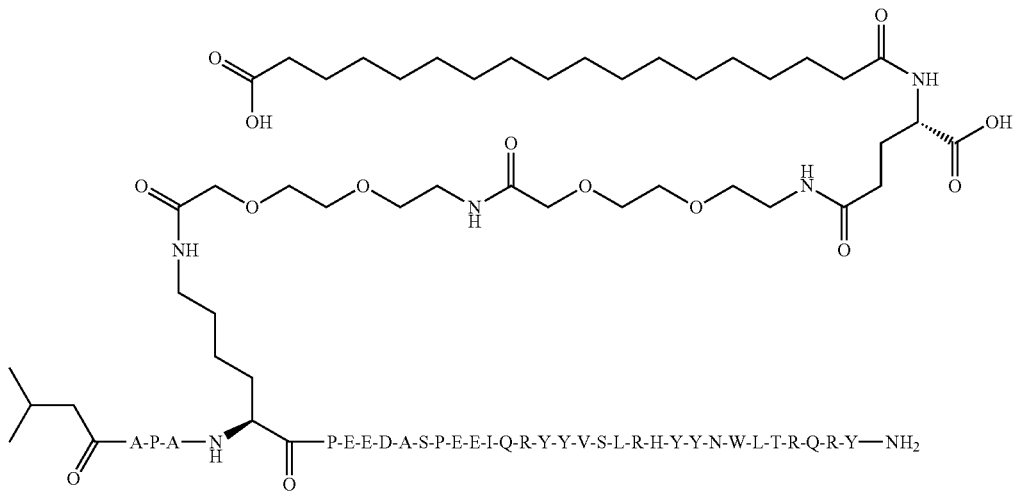

MW (calculated): 4929.6 Da
Synthesis and purification methods: S01; P01
LCMS: A01; Rt: 9.82 min; m/3: – m/4: 1233.0 m/5: -

Compound 24

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,18Q,22V,
26K,28Y,30W,31L]hPYY(4-36) iVal-APEK
(C18DA-gGlu-OEG1-OEG2-)
PEEDASPEELQRYYVSLRKYYNWLTRQRY-
NH2 (SEQ ID NO: 28)

MW (calculated): 4978.6 Da
Synthesis and purification methods: S01; P01
LCMS: A01; Rt: 9.70 min; m/3: 1661.0 m/4: – m/5: -

Compound 25

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11E,14A,
18Q,22V,28Y,30W,31L]hPYY(4-36) iVal-APEK
(C18DA-gGlu-OEG1-OEG2-)
PEEEASAEELQRYYVSLRHYYNWLTRQRY-
NH2 (SEQ ID NO: 29)

MW (calculated): 4975.6 Da
Synthesis and purification methods: S01; P01
LCMS: A01; Rt: 10.74 min; m/3: – m/4: 1245.0 m/5: -

Compound 26

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9P,13T,18Q,
22V,28Y,30W,31L]hPYY(4-36) iVal-APEK
(C18DA-gGlu-OEG1-OEG2-)
PPEDATPEELQRYYVSLRHYYNWLTRQRY-NH2
(sequence and structure below disclosed as SEQ ID
NO: 30)

MW (calculated): 4969.6 Da
Synthesis and purification methods: S01; P01
LCMS: A01; Rt: 9.74 min; m/3: – m/4: 1243.0 m/5: -

Compound 27

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9P,13E,18Q,
22V,28Y,30W,31L]hPYY(4-36) iVal-APEK
(C18DA-gGlu-OEG1-OEG2-)
PPEDAEPEELQRYYVSLRHYYNWLTRQRY-
NH2 (SEQ ID NO: 31)

MW (calculated): 4997.6 Da
Synthesis and purification methods: S01; P01
LCMS: A01; Rt: 10.11 min; m/3: 1667.0 m/4: – m/5: -

Compound 28

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,12T,18Q,
22V,28Y,30W,31L]hPYY(4-36) iVal-APEK
(C18DA-gGlu-OEG1-OEG2-)
PEEDTSPEELQRYYVELRHYYNWLTRQRY-NH2
(SEQ ID NO: 32)

MW (calculated): 5059.7 Da
Synthesis and purification methods: S01; P01
LCMS: A01; Rt: 9.77 min; m/3: 1688.0 m/4: – m/5: -

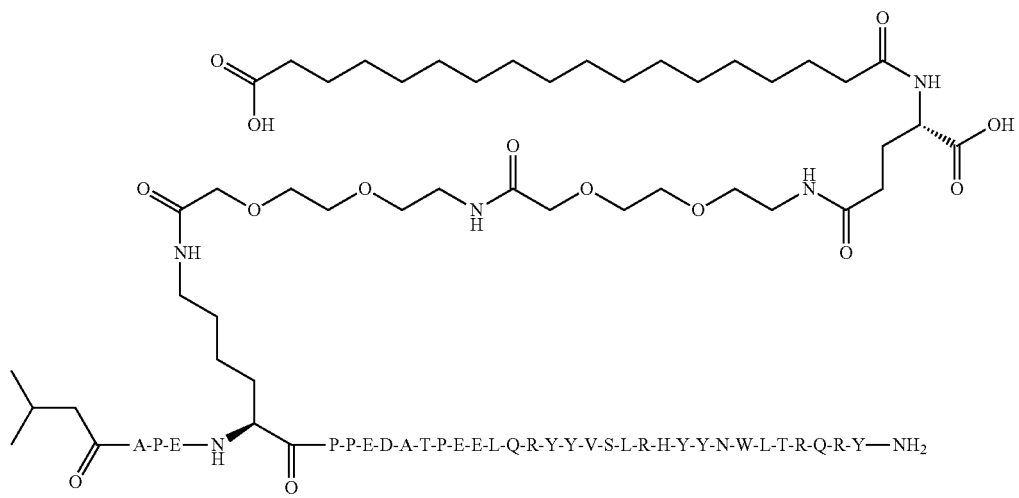

Compound 29

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,11P,18Q,22V,23E,28Y,30W,31L]hPYY(4-36) iVal-APEK(C18DA-gGlu-OEG1-OEG2-)PEAPASPEELQRYYVELRHYYNWLTRQRY-NH2 (sequence and structure below disclosed as SEQ ID NO: 33)

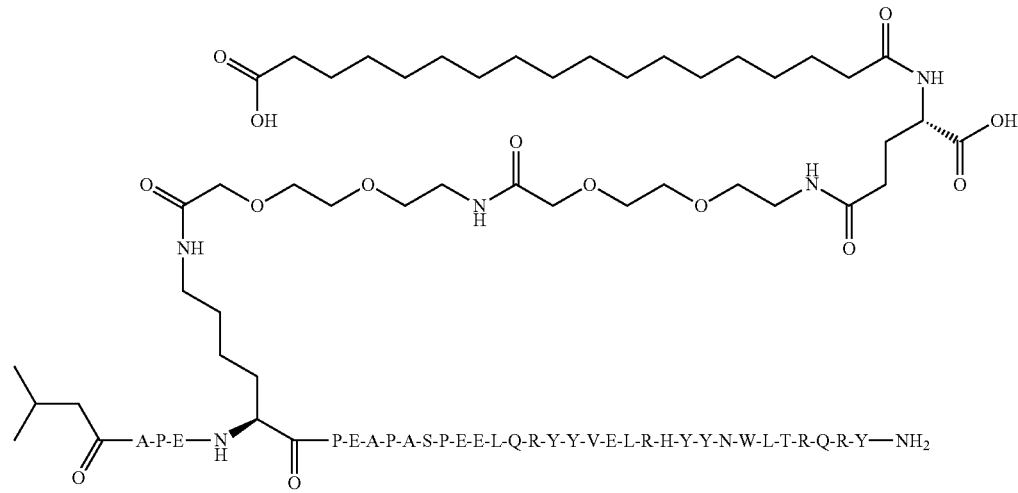

MW (calculated): 4953.6 Da
Synthesis and purification methods: S01; P01
LCMS: A01; Rt: 9.97 min; m/3: – m/4: 1239.0 m/5: -

Compound 30

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,14E,18Q,22V,28Y,30W,31L]hPYY(4-36) iVal-APEK(C18DA-gGlu-OEG1-OEG2-)PEADASEEELQRYYVSLRHYYNWLTRQRY-NH2 (SEQ ID NO: 34)

MW (calculated): 4961.6 Da
Synthesis and purification methods: S01; P01
LCMS: A01; Rt: 10.47 min; m/3: – m/4: 1241.0 m/5: -

Compound 31

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17T,18Q,22V,28Y,30W,31L]hPYY(4-36) iVal-APEK(C18DA-gGlu-OEG1-OEG2-)PEEDASPEETQRYYVALRHYYNWLTRQRY-NH2 (SEQ ID NO: 35)

MW (calculated): 4959.6 Da
Synthesis and purification methods: S01; P01
LCMS: A01; Rt: 9.26 min; m/3: 1654.0 m/4: – m/5: -

Compound 32

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,12T,18Q,22V,28Y,30W,31L]hPYY(4-36) iVal-APEK(C18DA-gGlu-OEG1-OEG2-)PEEDTSPEELQRYEVSLRHYYNWLTRQRY-NH2 (SEQ ID NO: 36)

MW (calculated): 4983.6 Da
Synthesis and purification methods: S01; P01
LCMS: A01; Rt: 9.46 min; m/3: – m/4: 1247.0 m/5: -

Compound 33

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11P,18Q,22V,23E,28Y,30W,31L]hPYY(4-36) iVal-APEK(C18DA-gGlu-OEG1-OEG2-)PEEPASPEELQRYYVELRHYYNWLTRQRY-NH2 (SEQ ID NO: 37)

MW (calculated): 5011.7 Da
Synthesis and purification methods: S01; P01
LCMS: A01; Rt: 9.85 min; m/3: – m/4: 1254.0 m/5: -

Compound 34

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,24T,18Q,22V,28Y,30W,31L]hPYY(4-36) iVal-APEK(C18DA-gGlu-OEG1-OEG2-)PEEDASPEELQRYYVSTRHYYNWLTRQRY-NH2 (SEQ ID NO: 38)

MW (calculated): 4975.6 Da
Synthesis and purification methods: S01; P01
LCMS: A01; Rt: 9.20 min; m/3: 1660.0 m/4: – m/5: -

Compound 35

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,17T,18Q,22V,28Y,30W,31L]hPYY(4-36) iVal-APEK(C18DA-gGlu-OEG1-OEG2-)PEEDAAPEETQRYYVSLRHYYNWLTRQRY-NH2 (SEQ ID NO: 39)

MW (calculated): 4959.6 Da
Synthesis and purification methods: S01; P01
LCMS: A01; Rt: 9.45 min; m/3: – m/4: 1240.0 m/5: -

Compound 36

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8A,9E,13E,18Q,22V,28Y,30W,31L]hPYY(4-36) iVal-APEK(C18DA-gGlu-OEG1-OEG2-)AEEDAEPEELQRYYVSLRHYYNWLTRQRY-NH2 (SEQ ID NO: 40)

MW (calculated): 5003.6 Da
Synthesis and purification methods: S01; P01
LCMS: A01; Rt: 10.34 min; m/3: – m/4: 1252.0 m/5: -

Compound 37

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17T,18Q,22V,28Y,30W,31L]hPYY(4-36) iVal-APEK(C18DA-gGlu-OEG1-OEG2-)PEEDASPEETQRYEVSLRHYYNWLTRQRY-NH2 (sequence and structure below disclosed as SEQ ID NO: 41)

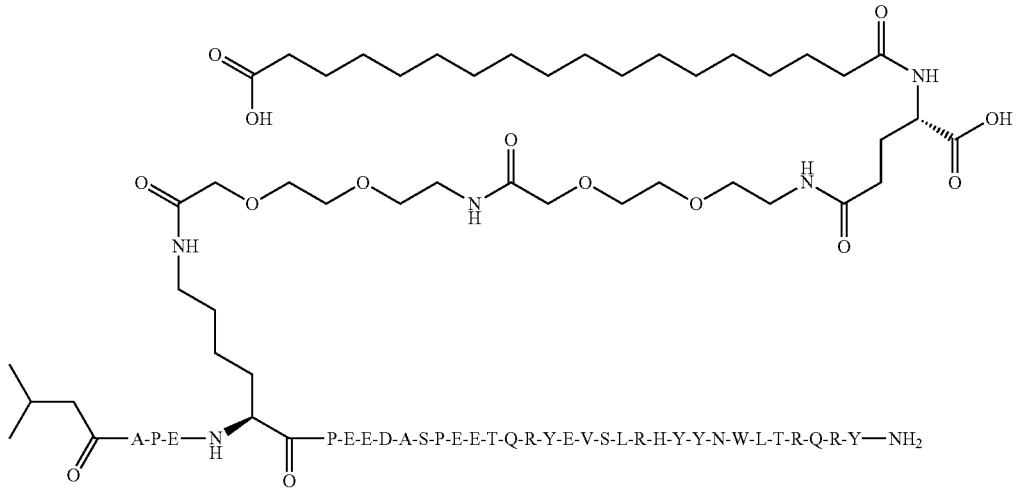

MW (calculated): 4941.5 Da
Synthesis and purification methods: S01; P01
LCMS: A01; Rt: 8.97 min; m/3: 1649.0 m/4: – m/5: –

Compound 38

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,18Q,22V,23A,28Y,30W,31L]hPYY(4-36) iVal-APEK(C18DA-gGlu-OEG1-OEG2-)PPEDASPEELQRYYVALRHYYNWLTRQRY-NH2 (SEQ ID NO: 42)

MW (calculated): 4939.6 Da
Synthesis and purification methods: S01; P01
LCMS: A01; Rt: 9.75 min; m/3: – m/4: 1236.0 m/5: -

Compound 39

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9P,10A,13E,
18Q,22V,28Y,30W,31L]hPYY(4-36) iVal-APEK
(C18DA-gGlu-OEG1-OEG2-)
PPADAEPEELQRYYVSLRHYYNWLTRQRY-
NH2 (SEQ ID NO: 43)

MW (calculated): 4939.6 Da
Synthesis and purification methods: S01; P01
LCMS: A01; Rt: 10.18 min; m/3: – m/4: 1236.0 m/5: -

Compound 40

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,13T,18Q,
22V,28Y,30W,31L]hPYY(4-36) iVal-APEK
(C18DA-gGlu-OEG1-OEG2-)
PEEDATPEETQRYYVSLRHYYNWLTRQRY-NH2
(SEQ ID NO: 44)

MW (calculated): 4989.6 Da
Synthesis and purification methods: S01; P01
LCMS: A01; Rt: 8.84 min; m/3: 1664.0 m/4: – m/5: -

Compound 41

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11E,13T,
18Q,22V,28Y,30W,31L]hPYY(4-36) iVal-APEK
(C18DA-gGlu-OEG1-OEG2-)
PEEEATPEELQRYYVSLRHYYNWLTRQRY-NH2
(SEQ ID NO: 45)

MW (calculated): 5015.7 Da
Synthesis and purification methods: S01; P01
LCMS: A01; Rt: 9.93 min; m/3: – m/4: 1255.0 m/5: -

Compound 42

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11A,18Q,
22V,24T,18Q,22V,28Y,30W,31L]hPYY(4-36) iVal-
APEK(C18DA-gGlu-OEG1-OEG2-)
PEEAASPEELQRYYVSTRHYYNWLTRQRY-
NH2 (SEQ ID NO: 46)

MW (calculated): 4931.5 Da
Synthesis and purification methods: S01; P01
LCMS: A01; Rt: 9.35 min; m/3: – m/4: 1234.0 m/5: -

Compound 43

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,10A,11P,
18Q,22V,28Y,30W,31L]hPYY(4-36) iVal-APEK
(C18DA-gGlu-OEG1-OEG2-)
PEAPASPEELQRYYVSLRHYYNWLTRQRY-NH2
(SEQ ID NO: 47)

MW (calculated): 4911.6 Da
Synthesis and purification methods: S01; P01
LCMS: A01; Rt: 9.86 min; m/3: 1638.0 m/4: – m/5: -

Compound 44

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11E,18Q,
22V,28Y,30W,31I]hPYY(4-36) iVal-APEK(C18DA-
gGlu-OEG1-OEG2-)
PEEEASPEELQRYYVSLRHYYNWITRQRY-NH2
(SEQ ID NO: 48)

MW (calculated): 5001.6 Da
Synthesis and purification methods: S01; P01
LCMS: A01; Rt: 9.66 min; m/3: 1668.0 m/4: – m/5: -

Compound 45

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11E,16S,
18Q,22V,28Y,30W,31L]hPYY(4-36) iVal-APEK
(C18DA-gGlu-OEG1-OEG2-)
PEEEASPESLQRYYVSLRHYYNWLTRQRY-NH2
(SEQ ID NO: 49)

MW (calculated): 4959.6 Da
Synthesis and purification methods: S01; P01
LCMS: A01; Rt: 9.96 min; m/3: – m/4: 1240.0 m/5: -

Compound 46

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,11E,18Q,
22V,28Y,30W,31L]hPYY(4-36) iVal-APEK
(C18DA-gGlu-OEG1-OEG2-)
PEEEASPEELQRYYVSLRHYYNWLTRQRY-NH2
(SEQ ID NO: 50)

MW (calculated): 5001.6 Da
Synthesis and purification methods: S01; P01
LCMS: A01; Rt: 9.80 min; m/3: 1668.0 m/4: – m/5: -

Compound 47

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,10A,18Q,22V,28Y,30W,31L]hPYY(4-36) iVal-APEK(C18DA-gGlu-OEG1-OEG2-)
PPADASPEELQRYYVSLRHYYNWLTRQRY-NH2
(SEQ ID NO: 51)

MW (calculated): 4897.6 Da
Synthesis and purification methods: S01; P01
LCMS: A01; Rt: 9.60 min; m/3: – m/4: 1224.0 m/5: -

Compound 48

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12T,18Q,22V,28Y,30W,31L]hPYY(4-36) iVal-APEK(C18DA-gGlu-OEG1-OEG2-)
PEEDTEPEELQRYYVSLRHYYNWLTRQRY-NH2
(SEQ ID NO: 52)

MW (calculated): 5059.7 Da
Synthesis and purification methods: S01; P01
LCMS: A01; Rt: 10.08 min; m/3: 1688.0 m/4: – m/5: -

Compound 49

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,19Q,22V,23E,28Y,30W,31L]hPYY(4-36) iVal-APEK(C18DA-gGlu-OEG1-OEG2-)
PEEDASPEELQQYYVELRHYYNWLTRQRY-NH2 (SEQ ID NO: 53)

MW (calculated): 5001.6 Da
Synthesis and purification methods: S01; P01
LCMS: A01; Rt: 9.95 min; m/3: – m/4: 1251.0 m/5: -

Compound 50

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q,22V,28Y,30W,31I]hPYY(4-36) iVal-APEK(C18DA-gGlu-OEG1-OEG2-)
PEEDASAEELQRYYVSLRHYYNWITRQRY-NH2
(SEQ ID NO: 54)

MW (calculated): 4961.6 Da
Synthesis and purification methods: S01; P01
LCMS: A01; Rt: 10.33 min; m/3: – m/4: 1241.0 m/5: -

Compound 51

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8A,9E,11E,18Q,22V,28Y,30W,31L]hPYY(4-36) iVal-APEK(C18DA-gGlu-OEG1-OEG2-)
AEEEASPEELQRYYVSLRHYYNWLTRQRY-NH2 (SEQ ID NO: 55)

MW (calculated): 4975.6 Da
Synthesis and purification methods: S01; P01
LCMS: A01; Rt: 10.07 min; m/3: 1659.0 m/4: – m/5: -

Compound 52

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8A,9E,14E,18Q,22V,28Y,30W,31L]hPYY(4-36) iVal-APEK(C18DA-gGlu-OEG1-OEG2-)
AEEDASEEELQRYYVSLRHYYNWLTRQRY-NH2 (SEQ ID NO: 56)

MW (calculated): 4993.6 Da
Synthesis and purification methods: S01; P01
LCMS: A01; Rt: 10.76 min; m/3: – m/4: 1249.0 m/5: -

Compound 53

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,17I,18Q,22V,28Y,30W,31L]hPYY(4-36) iVal-APEK(C18DA-gGlu-OEG1-OEG2-)
PEADASPEEIQRYYVSLRHYYNWLTRQRY-NH2
(sequence and structure below disclosed as SEQ ID NO: 57)

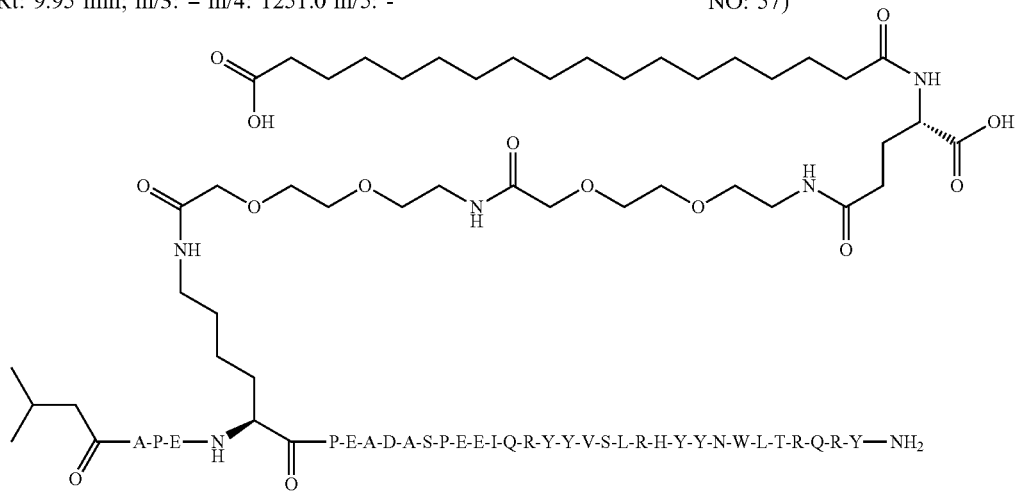

MW (calculated): 4929.6 Da
Synthesis and purification methods: S01; P01
LCMS: A01; Rt: 9.72 min; m/3: – m/4: 1233.0 m/5: -

Compound 54

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,28Y,30W,31L]hPYY(4-36) iVal-APEK(C18DA-gGlu-OEG1-OEG2-)PEEDASPEELQRYYVSLRHYYNWLTRQRY-NH2 (SEQ ID NO: 58)

MW (calculated): 4987.6 Da
Synthesis and purification methods: S01; P01
LCMS: A01; Rt: 9.77 min; m/3: – m/4: – m/5: 997.0

Compound 55

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17A,18Q,22V,28Y,30W,31L]hPYY(4-36) iVal-APEK(C18DA-gGlu-OEG1-OEG2-)PEEDASPEEAQRYYVSLRHYYNWLTRQRY-NH2 (SEQ ID NO: 59)

MW (calculated): 4945.5 Da
Synthesis and purification methods: S01; P01
LCMS: A01; Rt: 9.25 min; m/3: 1649.0 m/4: – m/5: -

Compound 56

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,13E,18Q,22V,28Y,30W,31L]hPYY(4-36) iVal-APEK(C18DA-gGlu-OEG1-OEG2-)PEADAEPEELQRYYVSLRHYYNWLTRQRY-NH2 (SEQ ID NO: 60)

MW (calculated): 4971.6 Da
Synthesis and purification methods: S01; P01
LCMS: A01; Rt: 10.17 min; m/3: – m/4: 1244.0 m/5: –

Compound 57

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,17I,18Q,22V,28Y,30W,31L]hPYY(4-36) iVal-APEK(C18DA-gGlu-OEG1-OEG2-)PEEDASAEEIQRYYVSLRHYYNWLTRQRY-NH2 (SEQ ID NO: 61)

MW (calculated): 4961.6 Da
Synthesis and purification methods: S01; P01
LCMS: A01; Rt: 10.50 min; m/3: – m/4: 1241.0 m/5: -

Compound 58

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,19Q,22V,28Y,30W,31L]hPYY(4-36) iVal-APEK(C18DA-gGlu-OEG1-OEG2-)PEEDASPEELQQYYVSLRHYYNWLTRQRY-NH2 (SEQ ID NO: 62)

MW (calculated): 4959.6 Da
Synthesis and purification methods: S01; P01
LCMS: A01; Rt: 9.87 min; m/3: – m/4: 1241.0 m/5: -

Compound 59

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17T,18Q,22V,28Y,30W,31L]hPYY(4-36) iVal-APEK(C18DA-gGlu-OEG1-OEG2-)PEEDASPEETEQYYVSLRHYYNWLTRQRY-NH2 (SEQ ID NO: 63)

MW (calculated): 4948.5 Da
Synthesis and purification methods: S02; P02
LCMS: A02; Rt: 13.67 min; m/3: 1651.0 m/4: 1238.0 m/5: 990.5

Compound 60

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18E,19Q,22V,28Y,30W,31L]hPYY(4-36) iVal-APEK(C18DA-gGlu-OEG1-OEG2-)PEEAASPEELEQYYVSLRHYYNWLTRQRY-NH2 (SEQ ID NO: 64)

MW (calculated): 4916.5 Da
Synthesis and purification methods: S01; P01
LCMS: A01; Rt: 10.30 min; m/3: – m/4: 1230.0 m/5: -

Compound 61

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,17I,18Q,22V,28Y,30W,31L]hPYY(4-36) iVal-APEK(C18DA-gGlu-OEG1-OEG2-)PPEDASPEEIQRYYVSLRHYYNWLTRQRY-NH2 (SEQ ID NO: 65)

MW (calculated): 4955.6 Da
Synthesis and purification methods: S01; P01
LCMS: A01; Rt: 9.51 min; m/3: – m/4: 1240.0 m/5: -

Compound 62

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,18E,22V,28Y,30W,31L]hPYY(4-36) iVal-APEK(C18DA-gGlu-OEG1-OEG2-)PGEDASPEELERYYVSLRHYYNWLTRQRY-NH2 (SEQ ID NO: 66)

MW (calculated): 4916.5 Da
Synthesis and purification methods: S01; P01
LCMS: A01; Rt: 9.91 min; m/3: – m/4: – m/5: 983.0

Compound 63

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,26A,28Y,30W,31L]hPYY(4-36) iVal-APEK(C18DA-gGlu-OEG1-OEG2-)PEEDASPEELQRYYVSLRAYYNWLTRQRY-NH2 (SEQ ID NO: 67)

MW (calculated): 4921.5 Da
Synthesis and purification methods: S01; P01
LCMS: A01; Rt: 10.10 min; m/3: 1641.0 m/4: – m/5: -

Compound 64

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,18Q,22V,28Y,30W,31L]hPYY(4-36) iVal-APEK(C18DA-gGlu-OEG1-OEG2-)PGEDASPEELQRYYVSLRHYYNWLTRQRY-NH2 (SEQ ID NO: 68)

MW (calculated): 4915.5 Da
Synthesis and purification methods: S01; P01
LCMS: A01; Rt: 9.65 min; m/3: 1639.0 m/4: – m/5: -

Compound 65

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,23E,24I,28Y,30W,31L]hPYY(4-36) iVal-APEK(C18DA-gGlu-OEG1-OEG2-)PEEDASPEELQRYYVEIRHYYNWLTRQRY-NH2 (sequence and structure below disclosed as SEQ ID NO: 69)

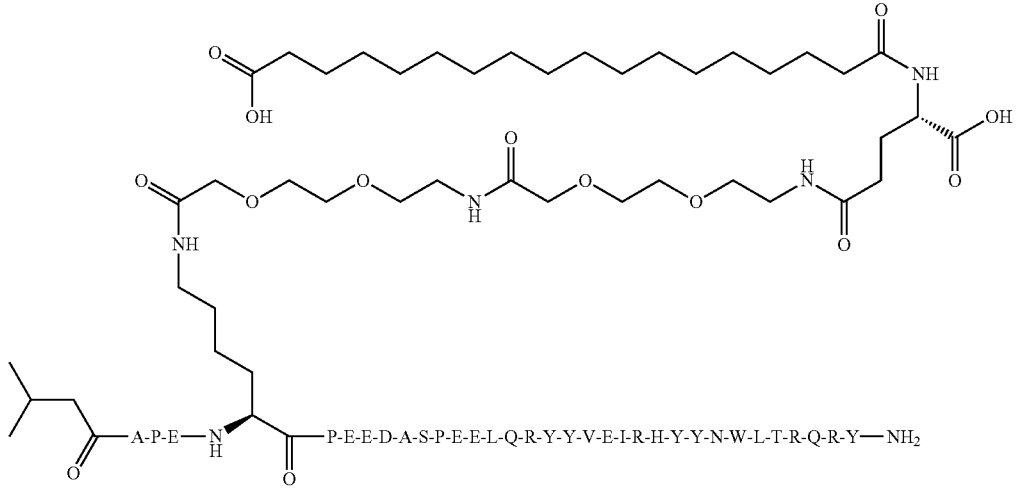

MW (calculated): 5029.6 Da
Synthesis and purification methods: S01; P01
LCMS: A01; Rt: 9.82 min; m/3: – m/4: 1258.0 m/5: –

Compound 66

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14A,17T,18Q,22V,28Y,30W,31L]hPYY(4-36) iVal-APEK(C18DA-gGlu-OEG1-OEG2-)PEEDASAEETQRYYVSLRHYYNWLTRQRY-NH2 (SEQ ID NO: 70)

MW (calculated): 4949.5 Da
Synthesis and purification methods: S01; P01
LCMS: A01; Rt: 9.61 min; m/3: – m/4: 1238.0 m/5: -

Compound 67

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,13A,18Q,22V,28Y,30W,31L]hPYY(4-36) iVal-APEK(C18DA-gGlu-OEG1-OEG2-)PEEDSAPEELQRYYVSLRHYYNWLTRQRY-NH2 (SEQ ID NO: 71)

MW (calculated): 4987.6 Da
Synthesis and purification methods: S01; P01
LCMS: A01; Rt: 10.60 min; m/3: – m/4: 1248.0 m/5: -

Compound 68

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,18Q,19A,22V,28Y,30W,31L]hPYY(4-36) iVal-APEK(C18DA-gGlu-OEG1-OEG2-)PEEEASPEELQAYYVSLRHYYNWLTRQRY-NH2 (SEQ ID NO: 72)

MW (calculated): 4916.5 Da
Synthesis and purification methods: S01; P01
LCMS: A01; Rt: 10.13 min; m/3: – m/4: 1230.0 m/5: -

Compound 69

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,14A,18Q,22V,28Y,30W,31L]hPYY(4-36) iVal-APEK(C18DA-gGlu-OEG1-OEG2-)PEEDSSAEELQRYYVSLRHYYNWLTRQRY-NH2 (SEQ ID NO: 73)

MW (calculated): 4977.6 Da
Synthesis and purification methods: S01; P01
LCMS: A01; Rt: 10.26 min; m/3: – m/4: 1245.0 m/5: -

Compound 70

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18Q,21E,22V,28Y,30W,31L]hPYY(4-36) iVal-APEK(C18DA-gGlu-OEG1-OEG2-)PEEAASPEELQRYEVSLRHYYNWLTRQRY-NH2 (SEQ ID NO: 74)

MW (calculated): 4909.5 Da
Synthesis and purification methods: S01; P01
LCMS: A01; Rt: 9.55 min; m/3: 1638.0 m/4: – m/5: -

Compound 71

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,15S,18Q,22V,28Y,30W,31L]hPYY(4-36) iVal-APEK(C18DA-gGlu-OEG1-OEG2-)PEEEASPSELQRYYVSLRHYYNWLTRQRY-NH2 (SEQ ID NO: 75)

MW (calculated): 4959.6 Da
Synthesis and purification methods: S01; P01
LCMS: A01; Rt: 9.96 min; m/3: – m/4: 1242.0 m/5: -

Compound 72

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,12G,18Q,22V,28Y,30W,31L]hPYY(4-36) iVal-APEK(C18DA-gGlu-OEG1-OEG2-)PEEEGSPEELQRYYVSLRHYYNWLTRQRY-NH2 (SEQ ID NO: 76)

MW (calculated): 4987.6 Da
Synthesis and purification methods: S01; P01
LCMS: A01; Rt: 9.87 min; m/3: – m/4: 1248.0 m/5: -

Compound 73

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,18Q,22V,26A,28Y,30W,31L]hPYY(4-36) iVal-APEK(C18DA-gGlu-OEG1-OEG2-)PEEEASPEELQRYYVSLRAYYNWLTRQRY-NH2 (SEQ ID NO: 77)

MW (calculated): 4935.6 Da
Synthesis and purification methods: S03; P02
LCMS: A02; Rt: 12.23 min; m/3: 1646.8 m/4: 1235.0 m/5: 988.0

Compound 74

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q,22V,23A,28Y,30W,31L]hPYY(4-36) iVal-APEK(C18DA-gGlu-OEG1-OEG2-)PEEDASAEELQRYYVALRHYYNWLTRQRY-NH2 (sequence and structure below disclosed as SEQ ID NO: 78)

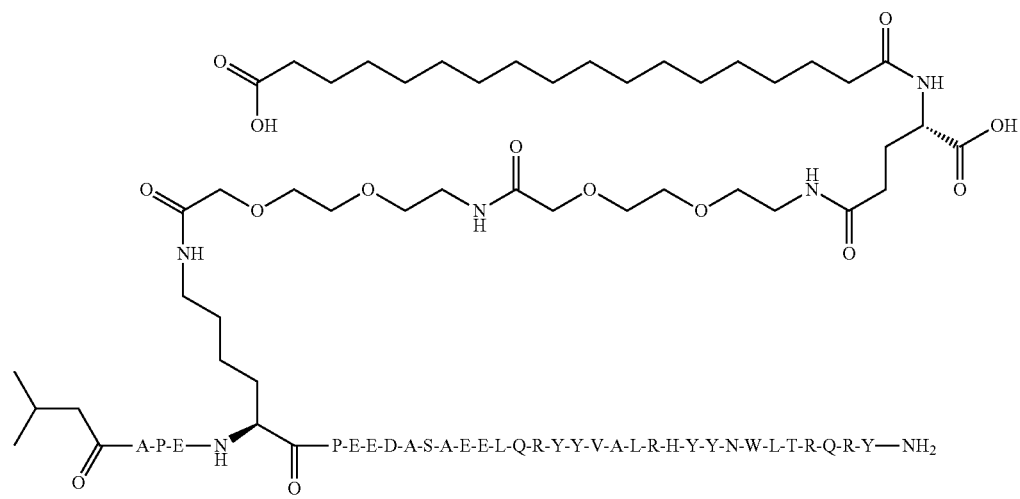

MW (calculated): 4945.6 Da

Synthesis and purification methods: S01; P01

LCMS: A01; Rt: 10.72 min; m/3: 1650.0 m/4: – m/5: –

Compound 75

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q,22V,23T,18Q,22V,28Y,30W,31L]hPYY(4-36) iVal-APEK(C18DA-gGlu-OEG1-OEG2-)PEEDASAEELQRYYVTLRHYYNWLTRQRY-NH2 (SEQ ID NO: 79)

MW (calculated): 4975.6 Da

Synthesis and purification methods: S01; P01

LCMS: A01; Rt: 10.74 min; m/3: – m/4: 1244.0 m/5: -

Compound 76

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,18Q,22V,28Y,30A,31L]hPYY(4-36) iVal-APEK(C18DA-gGlu-OEG1-OEG2-) PGEDASPEELQRYYVSLRHYYNALTRQRY-NH2 (sequence and structure below disclosed as SEQ ID NO: 80)

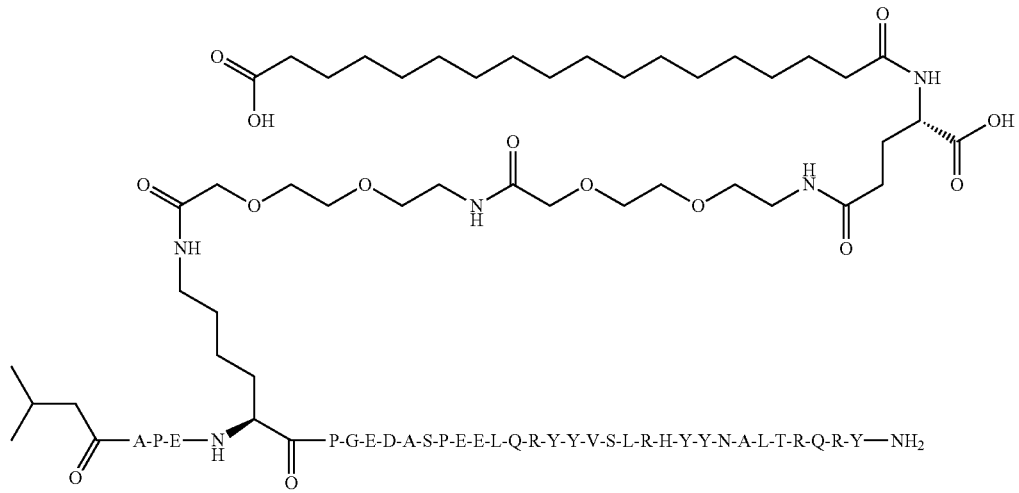

MW (calculated): 4800.4 Da
Synthesis and purification methods: S01; P01
LCMS: A01; Rt: 9.12 min; m/3: – m/4: 1201.0 m/5: -

Compound 77

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14E,18Q,22V,23E,28Y,30W,31L]hPYY(4-36) PEEDASEEELQRYYVELRHYYNWLTRQRY-NH2 (SEQ ID NO: 81)

MW (calculated): 5061.6 Da
Synthesis and purification methods: S01; P01
LCMS: A01; Rt: 10.44 min; m/3: – m/4: 1266.0 m/5: -

Compound 78

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,19Q,22V,23T,18Q,22V,28Y,30W,31L]hPYY(4-36) iVal-APEK(C18DA-gGlu-OEG1-OEG2-) PEEDAEPEELQQYYVTLRHYYNWLTRQRY-NH2 (SEQ ID NO: 82)

MW (calculated): 5043.7 Da
Synthesis and purification methods: S03; P02
LCMS: A02; Rt: 12.75 min; m/3: 1682.6 m/4: 1262.1 m/5: 1009.7

Compound 79

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,14E,18Q,22V,28Y,30W,31L]hPYY(4-36) iVal-APEK(C18DA-gGlu-OEG1-OEG2-) PEEEASEEELQRYYVSLRHYYNWLTRQRY-NH2 (SEQ ID NO: 83)

MW (calculated): 5033.6 Da
Synthesis and purification methods: S01; P01
LCMS: A01; Rt: 10.66 min; m/3: – m/4: 1260.0 m/5: -

Compound 80

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,17T,18Q,22V,28Y,30W,31L]hPYY(4-36) iVal-APEK(C18DA-gGlu-OEG1-OEG2-) PEEEASPEETQRYYVSLRHYYNWLTRQRY-NH2 (SEQ ID NO: 84)

MW (calculated): 4989.6 Da
Synthesis and purification methods: S01; P01
LCMS: A01; Rt: 9.19 min; m/3: – m/4: 1248.0 m/5: -

Compound 81

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,18Q,22V,
24I,28Y,30W,31L]hPYY(4-36) iVal-APEK(C18DA-
gGlu-OEG1-OEG2-)
PEEDASPEELQRYYVSIRHYYNWLTRQRY-NH2
(SEQ ID NO: 85)

MW (calculated): 4987.6 Da
Synthesis and purification methods: S01; P01
LCMS: A01; Rt: 9.72 min; m/3: 1664.0 m/4: – m/5: -

Compound 82

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,16A,18Q,
22V,23A,28Y,30W,31L]hPYY(4-36) iVal-APEK
(C18DA-gGlu-OEG1-OEG2-)
PEEDASPEALQRYYVALRHYYNWLTRQRY-
NH2 (SEQ ID NO: 86)

MW (calculated): 4913.6 Da
Synthesis and purification methods: S01; P01
LCMS: A01; Rt: 10.28 min; m/3: – m/4: 1229.0 m/5: -

Compound 83

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,10A,15A,
18Q,22V,28Y,30W,31L]hPYY(4-36) iVal-APEK
(C18DA-gGlu-OEG1-OEG2-)
PEADASPAELQRYYVSLRHYYNWLTRQRY-
NH2 (sequence and structure below disclosed as
SEQ ID NO: 87)

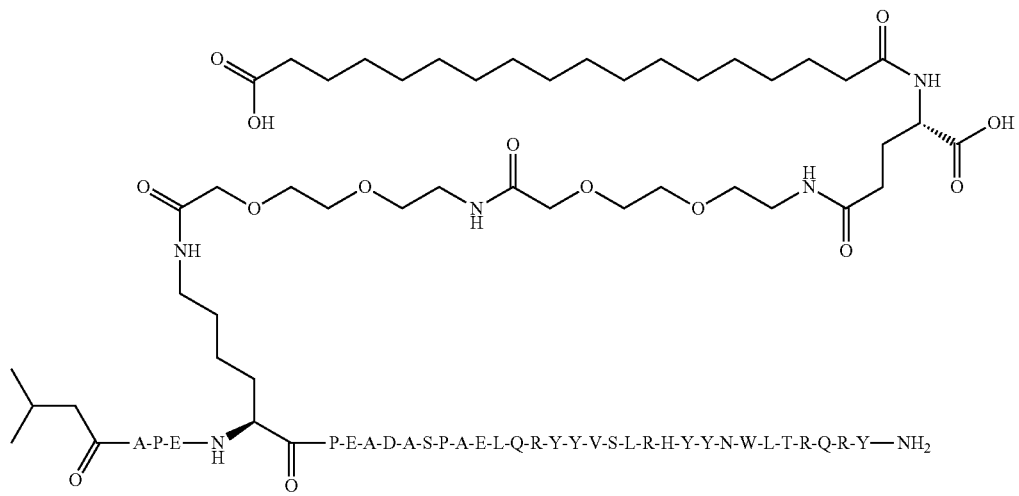

MW (calculated): 4871.5 Da
Synthesis and purification methods: S01; P01
LCMS: A01; Rt: 9.85 min; m/3: – m/4: 1219.0 m/5: -

Compound 84

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17I,18Q, 22V,28Y,30W,31L]hPYY(4-36) iVal-APEK(C18DA-gGlu-OEG1-OEG2-) PEEDASPEEIQRYYVSLRHYYNWLTRQRY-NH2 (sequence and structure below disclosed as SEQ ID NO: 88)

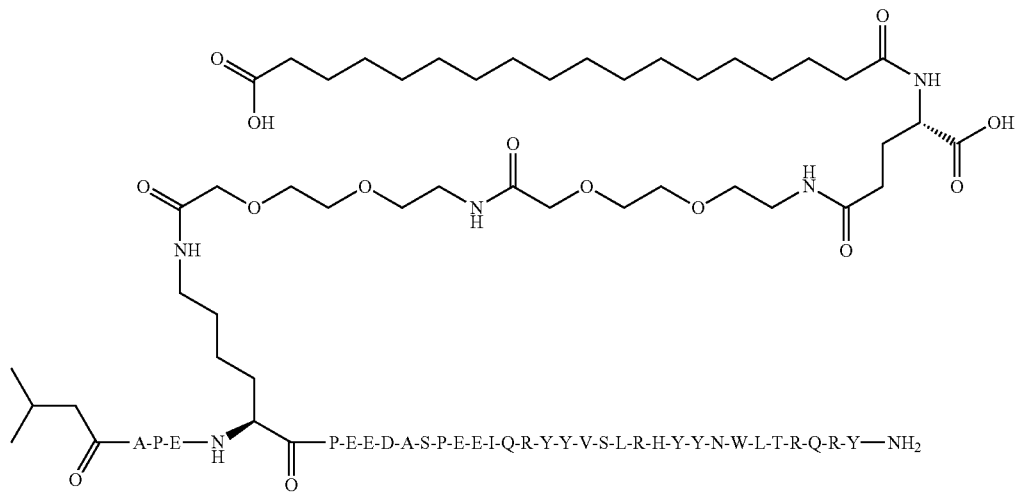

MW (calculated): 4987.6 Da
Synthesis and purification methods: S01; P01
LCMS: A01; Rt: 9.60 min; m/3: 1664.0 m/4: – m/5: -

Compound 85

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,21A, 22V,28Y,30W,31L]hPYY(4-36) iVal-APEK(C18DA-gGlu-OEG1-OEG2-) PEEDASPEELQRYAVSLRHYYNWLTRQRY-NH2 (SEQ ID NO: 89)

MW (calculated): 4895.5 Da
Synthesis and purification methods: S01; P01
LCMS: A01; Rt: 9.82 min; m/3: 1633.0 m/4: – m/5: -

Compound 86

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,18Q, 21E,22V,28Y,30W,31L]hPYY(4-36) iVal-APEK(C18DA-gGlu-OEG1-OEG2-) PEADASPEELQRYEVSLRHYYNWLTRQRY-NH2 (SEQ ID NO: 90)

MW (calculated): 4895.5 Da
Synthesis and purification methods: S01; P01
LCMS: A01; Rt: 9.44 min; m/3: – m/4: 1224.0 m/5: -

Compound 87

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,15A,18Q,22V,28Y,30W,31L]hPYY(4-36) iVal-APEK(C18DA-gGlu-OEG1-OEG2-)PEEDSSPAELQRYYVSLRHYYNWLTRQRY-NH2 (sequence and structure below disclosed as SEQ ID NO: 91)

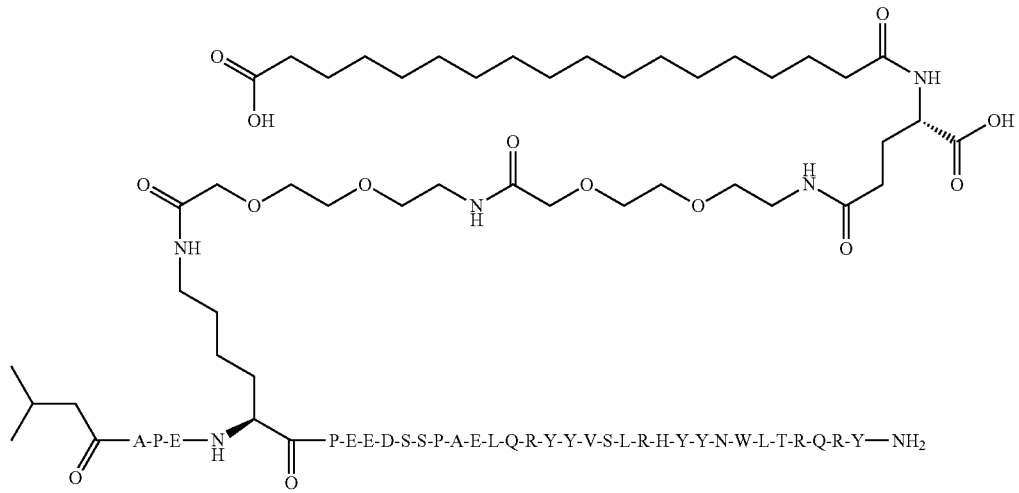

MW (calculated): 4945.6 Da
Synthesis and purification methods: S01; P01
LCMS: A01; Rt: 9.82 min; m/3: – m/4: 1237.0 m/5: –

Compound 88

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,18Q,22V,23E,28Y,30W,31L]hPYY(4-36) iVal-APEK(C18DA-gGlu-OEG1-OEG2-)PPEDASPEELQRYYVELRHYYNWLTRQRY-NH2 (SEQ ID NO: 92)

MW (calculated): 4997.6 Da
Synthesis and purification methods: S01; P01
LCMS: A01; Rt: 9.62 min; m/3: – m/4: 1250.0 m/5: -

Compound 89

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,13E,18Q,22V,28Y,30W,31L]hPYY(4-36) iVal-APEK(C18DA-gGlu-OEG1-OEG2-)PEEEAEPEELQRYYVSLRHYYNWLTRQRY-NH2 (SEQ ID NO: 93)

MW (calculated): 5043.7 Da
Synthesis and purification methods: S01; P01
LCMS: A01; Rt: 10.08 min; m/3: – m/4: 1261.0 m/5: -

Compound 90

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,21E,22V,28Y,30W,31L]hPYY(4-36) iVal-APEK(C18DA-gGlu-OEG1-OEG2-)PEEDASPEELQRYEVSLRHYYNWLTRQRY-NH2 (SEQ ID NO: 94)

MW (calculated): 4953.5 Da
Synthesis and purification methods: S01; P01
LCMS: A01; Rt: 9.46 min; m/3: 1651.0 m/4: – m/5: -

Compound 91

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13P,14A,18Q,22V,23E,28Y,30W,31L]hPYY(4-36) iVal-APEK(C18DA-gGlu-OEG1-OEG2-)PEEDAPAEELQRYYVELRHYYNWLTRQRY-NH2 (SEQ ID NO: 95)

MW (calculated): 5013.6 Da
Synthesis and purification methods: S01; P01
LCMS: A01; Rt: 11.44 min; m/3: – m/4: 1254.0 m/5: -

Compound 92

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12T,18Q,22V,28Y,30W,31L]hPYY(4-36) iVal-APEK (C18DA-gGlu-OEG1-OEG2-)PEEDTSPEELQRYYVSLRHYYNWLTRQRY-NH2 (SEQ ID NO: 96)

MW (calculated): 5017.6 Da
Synthesis and purification methods: S01; P01
LCMS: A01; Rt: 9.76 min; m/3: – m/4: 1256.0 m/5: -

Compound 93

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q,19K,22V,28Y,30W,31L]hPYY(4-36) iVal-APEK (C18DA-gGlu-OEG1-OEG2-)PEEDASAEELQKYYVSLRHYYNWLTRQRY-NH2 (SEQ ID NO: 97)

MW (calculated): 4933.6 Da
Synthesis and purification methods: S03; P02
LCMS: A02; Rt: 12.03 min; m/3: 1646.0 m/4: 1234.3 m/5: 987.4

Compound 94

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17T,18Q,22V,23E,28Y,30W,31L]hPYY(4-36) iVal-APEK (C18DA-gGlu-OEG1-OEG2-)PEEDASPEETQRYYVELRHYYNWLTRQRY-NH2 (SEQ ID NO: 98)

MW (calculated): 5017.6 Da
Synthesis and purification methods: S01; P01
LCMS: A01; Rt: 9.15 min; m/3: – m/4: 1256.0 m/5: -

Compound 95

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,15A,17I,18Q,22V,28Y,30W,31L]hPYY(4-36) iVal-APEK (C18DA-gGlu-OEG1-OEG2-)PEEDASPAEIQRYYVSLRHYYNWLTRQRY-NH2 (SEQ ID NO: 99)

MW (calculated): 4929.6 Da
Synthesis and purification methods: S01; P01
LCMS: A01; Rt: 9.69 min; m/3: 1644.0 m/4: – m/5: -

Compound 96

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,18Q,22V,28Y,30W,31L]hPYY(4-36) iVal-APEK (C18DA-gGlu-OEG1-OEG2-)PEADASPEELQRYYVSLRHYYNWLTRQRY-NH2 (SEQ ID NO: 100)

MW (calculated): 4929.6 Da
Synthesis and purification methods: S01; P01
LCMS: A01; Rt: 9.70 min; m/3: 1644.0 m/4: – m/5: -

Compound 97

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,23A,28Y,30W,31L]hPYY(4-36) iVal-APEK (C18DA-gGlu-OEG1-OEG2-)PEEDASPEELQRYYVALRHYYNWLTRQRY-NH2 (SEQ ID NO: 101)

MW (calculated): 4971.6 Da
Synthesis and purification methods: S01; P01
LCMS: A01; Rt: 9.86 min; m/3: – m/4: 1244.0 m/5: -

Compound 98

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22S,23A,28Y,30W,31L]hPYY(4-36) iVal-APEK (C18DA-gGlu-OEG1-OEG2-)PEEDASPEELQRYYSALRHYYNWLTRQRY-NH2 (SEQ ID NO: 102)

MW (calculated): 4959.6 Da
Synthesis and purification methods: S01; P01
LCMS: A01; Rt: 9.71 min; m/3: 1654.0 m/4: – m/5: -

Compound 99

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13E,14A,18Q,22V,28Y,30W,31L]hPYY(4-36) iVal-APEK (C18DA-gGlu-OEG1-OEG2-)PEEDAEAEELQRYYVSLRHYYNWLTRQRY-NH2 (SEQ ID NO: 103)

MW (calculated): 5003.6 Da
Synthesis and purification methods: S01; P01
LCMS: A01; Rt: 10.61 min; m/3: 1668.0 m/4: – m/5: -

Compound 100

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9P,18Q,22V,28Y,30W,31L]hPYY(4-36) iVal-APAK(C18DA-gGlu-OEG1-OEG2-)PPEDASPEELQRYYVSLRHYYNWLTRQRY-NH2 (SEQ ID NO: 104)

MW (calculated): 4897.6 Da
Synthesis and purification methods: S01; P01
LCMS: A01; Rt: 9.76 min; m/3: – m/4: 1225.0 m/5: –

Compound 101

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13T,18Q,22V,28Y,30W,31L]hPYY(4-36) iVal-APEK(C18DA-gGlu-OEG1-OEG2-)PEEDATPEELQRYYVELRHYYNWLTRQRY-NH2 (SEQ ID NO: 105)

MW (calculated): 5043.7 Da
Synthesis and purification methods: S01; P01
LCMS: A01; Rt: 9.92 min; m/3: – m/4: 1261.0 m/5: –

Compound 102

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,23T,18Q,22V,28Y,30W,31L]hPYY(4-36) iVal-APEK(C18DA-gGlu-OEG1-OEG2-)PEEDASPEELQRYYVTLRHYYNWLTRQRY-NH2 (SEQ ID NO: 106)

MW (calculated): 5001.6 Da
Synthesis and purification methods: S01; P01
LCMS: A01; Rt: 9.88 min; m/3: 1668.0 m/4: – m/5: –

Compound 103

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9E,14E,18Q,22V,28Y,30W,31L]hPYY(4-36) iVal-APAK(C18DA-gGlu-OEG1-OEG2-)PEEDASEEELQRYYVSLRHYYNWLTRQRY-NH2 (SEQ ID NO: 107)

MW (calculated): 4961.6 Da
Synthesis and purification methods: S01; P01
LCMS: A01; Rt: 10.03 min; m/3: 1654.0 m/4: – m/5: –

Compound 104

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14A,18Q,22V,28Y,30W,31L]hPYY(4-36) iVal-APEK(C18DA-gGlu-OEG1-OEG2-)PEEDASAEELQRYYVSLRHYYNWLTRQRY-NH2 (SEQ ID NO: 108)

MW (calculated): 4963.6 Da
Synthesis and purification methods: S01; P01
LCMS: A01; Rt: 10.39 min; m/3: – m/4: 1241.0 m/5: –

Compound 105

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,19E,22V,28Y,30W,31L]hPYY(4-36) iVal-APEK(C18DA-gGlu-OEG1-OEG2-)PEEDAEPEELQEYYVSLRHYYNWLTRQRY-NH2 (SEQ ID NO: 109)

MW (calculated): 5002.6 Da
Synthesis and purification methods: S01; P01
LCMS: A01; Rt: 10.41 min; m/3: – m/4: 1251.0 m/5: –

Compound 106
N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,13T,18Q, 22V,28Y,30W,31L]hPYY(4-36) iVal-APAK (C18DA-gGlu-OEG1-OEG2-) PEEDATPEELQRYYVSLRHYYNWLTRQRY-NH2 (sequence and structure below disclosed as SEQ ID NO: 110)
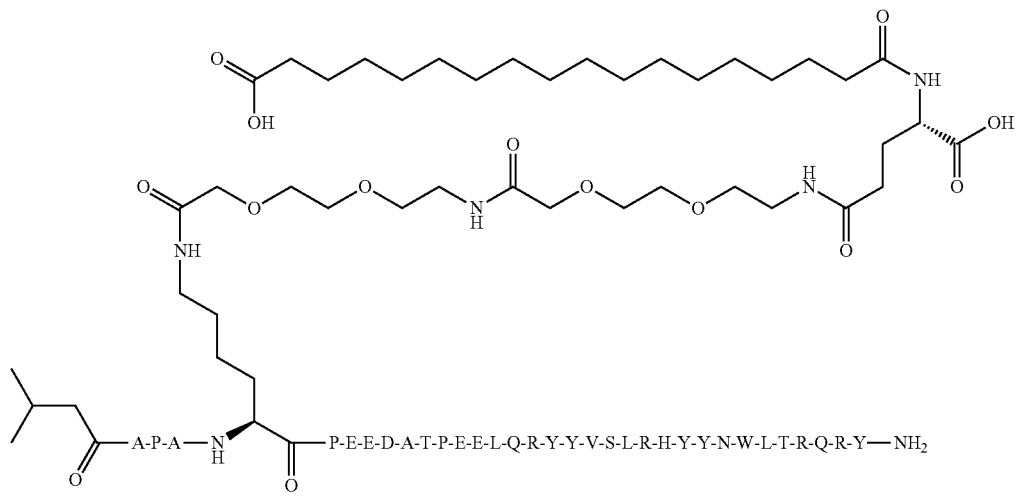
MW (calculated): 4943.6 Da
Synthesis and purification methods: S01; P01
LCMS: A01; Rt: 10.03 min; m/3: –  m/4: 1237.0 m/5: -

Compound 107

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,19K,22V,23A,28Y,30W,31L]hPYY(4-36) iVal-APEK(C18DA-gGlu-OEG1-OEG2-)PEEDASPEELQKYYVALRHYYNWLTRQRY-NH2 (sequence and structure below disclosed as SEQ ID NO: 111)

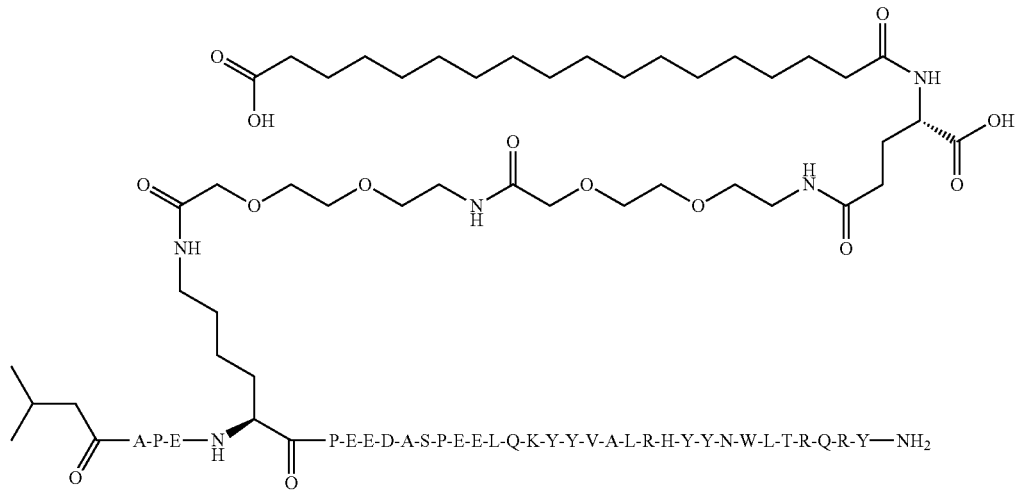

MW (calculated): 4943.6 Da
Synthesis and purification methods: S03; P02
LCMS: A02; Rt: 11.80 min; m/3: 1648.6 m/4: 1236.9 m/5: 989.5

Compound 108

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,23E,28Y,30W,31L]hPYY(4-36) iVal-APEK(C18DA-gGlu-OEG1-OEG2-)PEEDASPEELQRYYVELRHYYNWLTRQRY-NH2 (SEQ ID NO: 112)

MW (calculated): 5029.6 Da
Synthesis and purification methods: S03; P02
LCMS: A02; Rt: 11.47 min; m/3: 1678.1 m/4: 1258.1 m/5: 1006.7

Compound 109

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11A,18Q,22V,28Y,30W,31L]hPYY(4-36) iVal-APEK(C18DA-gGlu-OEG1-OEG2-)PEEAASPEELQRYYVSLRHYYNWLTRQRY-NH2 (SEQ ID NO: 113)

MW (calculated): 4943.6 Da
Synthesis and purification methods: S01; P01
LCMS: A01; Rt: 9.90 min; m/3: 1649.0 m/4: – m/5: –

Compound 110

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,17I,18Q,22V,28Y,30W,31L]hPYY(4-36) iVal-APEK(C18DA-gGlu-OEG1-OEG2-)PEEDAEPEEIQRYYVSLRHYYNWLTRQRY-NH2 (SEQ ID NO: 114)

MW (calculated): 5029.6 Da
Synthesis and purification methods: S01; P01
LCMS: A01; Rt: 10.10 min; m/3: – m/4: 1258.0 m/5: –

Compound 111

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,22V,23E,28Y,30W,31L]hPYY(4-36) iVal-APEK(C18DA-gGlu-OEG1-OEG2-)PEEDAEPEELQRYYVELRHYYNWLTRQRY-NH2 (SEQ ID NO: 115)

MW (calculated): 5071.7 Da
Synthesis and purification methods: S01; P01
LCMS: A01; Rt: 10.17 min; m/3: – m/4: 1268.0 m/5: –

Compound 112

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13T,18Q,22V,28Y,30W,31L]hPYY(4-36) iVal-APEK(C18DA-gGlu-OEG1-OEG2-) PEEDATPEELQRYYVSLRHYYNWLTRQRY-NH2 (sequence and structure below disclosed as SEQ ID NO: 116)

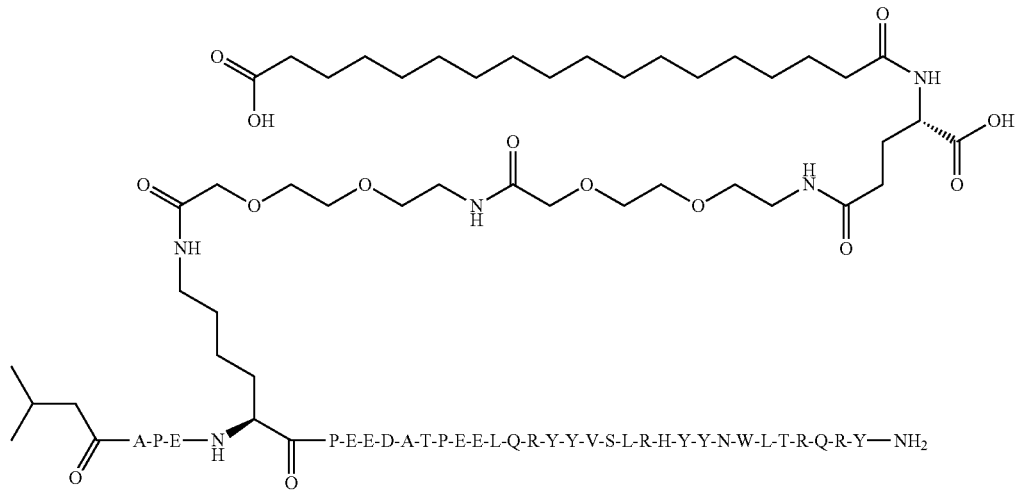

MW (calculated): 5001.6 Da
Synthesis and purification methods: S01; P01
LCMS: A01; Rt: 9.85 min; m/3: – m/4: 1252.0 m/5: -

Compound 113

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,8A,9E,13T,18Q,22V,28Y,30W,31L]hPYY(4-36) iVal-APEK(C18DA-gGlu-OEG1-OEG2-) AEEDATPEELQRYYVSLRHYYNWLTRQRY-NH2 (SEQ ID NO: 117)

MW (calculated): 4975.6 Da
Synthesis and purification methods: S01; P01
LCMS: A01; Rt: 10.22 min; m/3: 1659.0 m/4: – m/5: -

Compound 114

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,28H,29W,30Y,31L]hPYY(4-36) iVal-APEK(C18DA-gGlu-OEG1-OEG2-) PEEDASPEELQRYYVSLRHYHWYLTRQRY-NH2 (SEQ ID NO: 118)

MW (calculated): 5010.6 Da
Synthesis and purification methods: S02; P02
LCMS: A02; Rt: 12.38 min; m/3: 1671.2 m/4: 1253.9 m/5: –

Compound 115

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,16A,18Q,22V,28Y,30W,31L]hPYY(4-36) iVal-APEK(C18DA-gGlu-OEG1-OEG2-) PEEEASPEALQRYYVSLRHYYNWLTRQRY-NH2 (SEQ ID NO: 119)

MW (calculated): 4943.6 Da
Synthesis and purification methods: S01; P01
LCMS: A01; Rt: 10.09 min; m/3: – m/4: 1237.0 m/5: -

Compound 116

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13A,14A,18Q,22V,28Y,30W,31L]hPYY(4-36) iVal-APEK(C18DA-gGlu-OEG1-OEG2-) PEEDAAAEELQRYYVSLRHYYNWLTRQRY-NH2 (SEQ ID NO: 120)

MW (calculated): 0.0 Da
Synthesis and purification methods: S01; P01
LCMS: A01; Rt: 11.36 min; m/3: – m/4: 1238.0 m/5: -

Compound 117

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9E,18Q,22V,23A,28Y,30W,31L]hPYY(4-36) iVal-APAK(C18DA-gGlu-OEG1-OEG2-)PEEDASPEELQRYYVALRHYYNWLTRQRY-NH2 (sequence and structure below disclosed as SEQ ID NO: 121)

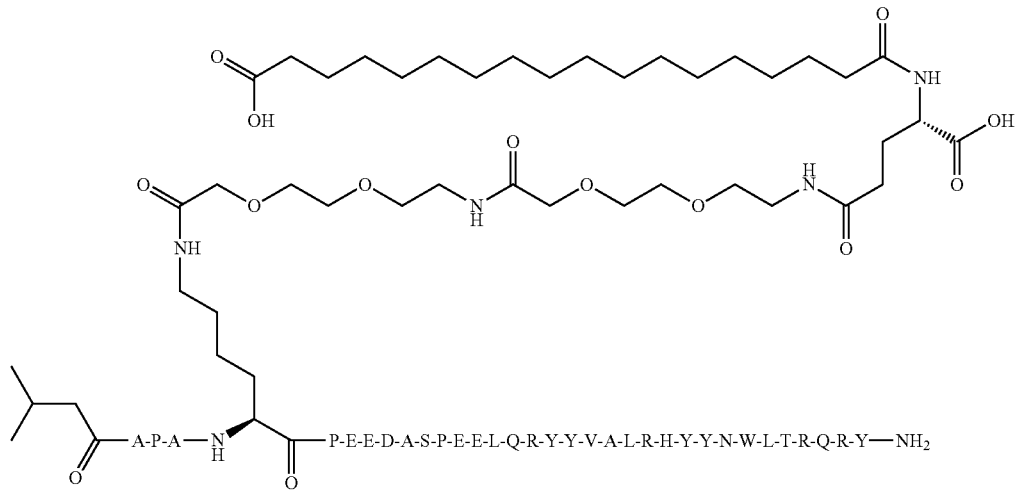

MW (calculated): 4913.6 Da
Synthesis and purification methods: S01; P01
LCMS: A01; Rt: 10.08 min; m/3: – m/4: 1228.0 m/5: -

Compound 118

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14A,15A,18Q,22V,28Y,30W,31L]hPYY(4-36) iVal-APEK(C18DA-gGlu-OEG1-OEG2-)PEEDASAAELQRYYVSLRHYYNWLTRQRY-NH2 (SEQ ID NO: 122)

MW (calculated): 4903.5 Da
Synthesis and purification methods: S01; P01
LCMS: A01; Rt: 10.49 min; m/3: 1636.0 m/4: – m/5: -

Compound 119

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,22V,23T,18Q,22V,28Y,30W,31L]hPYY(4-36) iVal-APEK(C18DA-gGlu-OEG1-OEG2-)PEEEASPEELQRYYVTLRHYYNWLTRQRY-NH2 (SEQ ID NO: 123)

MW (calculated): 5015.7 Da
Synthesis and purification methods: S01; P01
LCMS: A01; Rt: 9.99 min; m/3: – m/4: 1254.0 m/5: -

Compound 120

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,13E,14E,18Q,19E,22V,28Y,30W,31L]hPYY(4-36) iVal-APEK(C18DA-gGlu-OEG1-OEG2-)PGEDAEEEELQEYYVSLRHYYNWLTRQRY-NH2 (SEQ ID NO: 124)

MW (calculated): 4962.5 Da
Synthesis and purification methods: S01; P01
LCMS: A01; Rt: 10.78 min; m/3: – m/4: 1241.0 m/5: -

Compound 121

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9E,10A,18Q,22V,28Y,30W,31L]hPYY(4-36) iVal-APAK(C18DA-gGlu-OEG1-OEG2-)PEADASPEELQRYYVSLRHYYNWLTRQRY-NH2 (SEQ ID NO: 125)

MW (calculated): 4871.5 Da
Synthesis and purification methods: S01; P01
LCMS: A01; Rt: 9.95 min; m/3: – m/4: 1624.0 m/5: -

Compound 122

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,18Q,22V,28Y,30W,31L]hPYY(4-36) iVal-APEK(C18DA-gGlu-OEG1-OEG2-)PEEDAAPEELQRYYVSLRHYYNWLTRQRY-NH2 (SEQ ID NO: 126)

MW (calculated): 4971.6 Da
Synthesis and purification methods: S01; P01
LCMS: A01; Rt: 10.55 min; m/3: 1658.0 m/4: – m/5: -

Compound 123

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,28W,29Y,30H,31L]hPYY(4-36) PEEDASPEELQRYYVSLRHYWYHLTRQRY-NH2 (SEQ ID NO: 127)

MW (calculated): 5010.6 Da
Synthesis and purification methods: S02; P02
LCMS: A02; Rt: 9.68 min; m/3: 1671.7 m/4: 1253.7 m/5: -

Compound 124

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,17I,18Q,22V,28Y,30W,31L]hPYY(4-36) iVal-APEK(C18DA-gGlu-OEG1-OEG2-)PEEDAAPEEIQRYYVSLRHYYNWLTRQRY-NH2 (SEQ ID NO: 128)

MW (calculated): 4971.6 Da
Synthesis and purification methods: S01; P01
LCMS: A01; Rt: 10.55 min; m/3: – m/4: 1244.0 m/5: -

Compound 125

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,18Q,22V,28Y,30W,31A]hPYY(4-36) iVal-APEK(C18DA-gGlu-OEG1-OEG2-)PGEDASPEELQRYYVSLRHYYNWATRQRY-NH2 (SEQ ID NO: 129)

MW (calculated): 4873.5 Da
Synthesis and purification methods: S01; P01
LCMS: A01; Rt: 9.06 min; m/3: 1625.0 m/4: – m/5: -

Compound 126

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,12S,18Q,22V,28Y,30W,31L]hPYY(4-36) iVal-APAK(C18DA-gGlu-OEG1-OEG2-)PEEDSSPEELQRYYVSLRHYYNWLTRQRY-NH2 (SEQ ID NO: 130)

MW (calculated): 4945.6 Da
Synthesis and purification methods: S01; P01
LCMS: A01; Rt: 9.89 min; m/3: 1649.0 m/4: – m/5: -

Compound 127

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,14A,18Q,22V,28Y,30W,31L]hPYY(4-36) iVal-APAK(C18DA-gGlu-OEG1-OEG2-)PEEDASAEELQRYYVSLRHYYNWLTRQRY-NH2 (SEQ ID NO: 131)

MW (calculated): 4903.5 Da
Synthesis and purification methods: S01; P01
LCMS: A01; Rt: 10.80 min; m/3: – m/4: 1226.0 m/5: -

Compound 128

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13P,14A,17I,18Q,22V,28Y,30W,31L]hPYY(4-36) iVal-APEK(C18DA-gGlu-OEG1-OEG2-)PEEDAPAEEIQRYYVSLRHYYNWLTRQRY-NH2 (SEQ ID NO: 132)

MW (calculated): 4971.6 Da
Synthesis and purification methods: S01; P01
LCMS: A01; Rt: 11.28 min; m/3: 1658.0 m/4: – m/5: -

Compound 129

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17T,18Q,22V,28Y,30W,31L]hPYY(4-36) iVal-APEK(C18DA-gGlu-OEG1-OEG2-)PEEDASPEETQRYYTALRHYYNWLTRQRY-NH2 (SEQ ID NO: 133)

MW (calculated): 4961.5 Da
Synthesis and purification methods: S01; P01
LCMS: A01; Rt: 9.22 min; m/3: – m/4: 1241.0 m/5: –

Compound 130

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,12T,14A,18Q,22V,28Y,30W,31L]hPYY(4-36) iVal-APEK(C18DA-gGlu-OEG1-OEG2-)PEEDTSAEELQRYYVSLRHYYNWLTRQRY-NH2 (SEQ ID NO: 134)

MW (calculated): 4991.6 Da
Synthesis and purification methods: S01; P01
LCMS: A01; Rt: 10.30 min; m/3: 1665.0 m/4: – m/5: -

Compound 131

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,8A,9E,18Q,22V,23E,28Y,30W,31L]hPYY(4-36) iVal-APEK(C18DA-gGlu-OEG1-OEG2-)AEEDASPEELQRYYVELRHYYNWLTRQRY-NH2 (SEQ ID NO: 135)

MW (calculated): 5002.6 Da
Synthesis and purification methods: S01; P01
LCMS: A01; Rt: 10.10 min; m/3: – m/4: 1251.0 m/5: -

Compound 132

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,19K,22V,23T,28Y,30W,31L]hPYY(4-36) iVal-APEK(C18DA-gGlu-OEG1-OEG2-)PEEDASPEELQKYYVTLRHYYNWLTRQRY-NH2 (SEQ ID NO: 136)

MW (calculated): 4973.6 Da
Synthesis and purification methods: S03; P02
LCMS: A02; Rt: 11.78 min; m/3: 1659.4 m/4: 1244.6 m/5: 995.3

Compound 133

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17V,18Q,22V,23E,28Y,30W,31L]hPYY(4-36) iVal-APEK(C18DA-gGlu-OEG1-OEG2-)PEEDASPEEVQRYYVELRHYYNWLTRQRY-NH2 (SEQ ID NO: 137)

MW (calculated): 5015.6 Da
Synthesis and purification methods: S01; P01
LCMS: A01; Rt: 9.45 min; m/3: – m/4: 1254.0 m/5: -

Compound 134

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17I,18Q,22T,18Q,22V,23E,28Y,30W,31L]hPYY(4-36) iVal-APEK(C18DA-gGlu-OEG1-OEG2-)PEEDASPEEIQRYYTELRHYYNWLTRQRY-NH2 (SEQ ID NO: 138)

MW (calculated): 5031.6 Da
Synthesis and purification methods: S01; P01
LCMS: A01; Rt: 9.54 min; m/3: – m/4: 1258.0 m/5: -

Compound 135

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,18Q,22V,23E,28Y,30W,31L]hPYY(4-36) iVal-APEK(C18DA-gGlu-OEG1-OEG2-)PEADASPEELQRYYVELRHYYNWLTRQRY-NH2 (sequence and structure below disclosed as SEQ ID NO: 139)

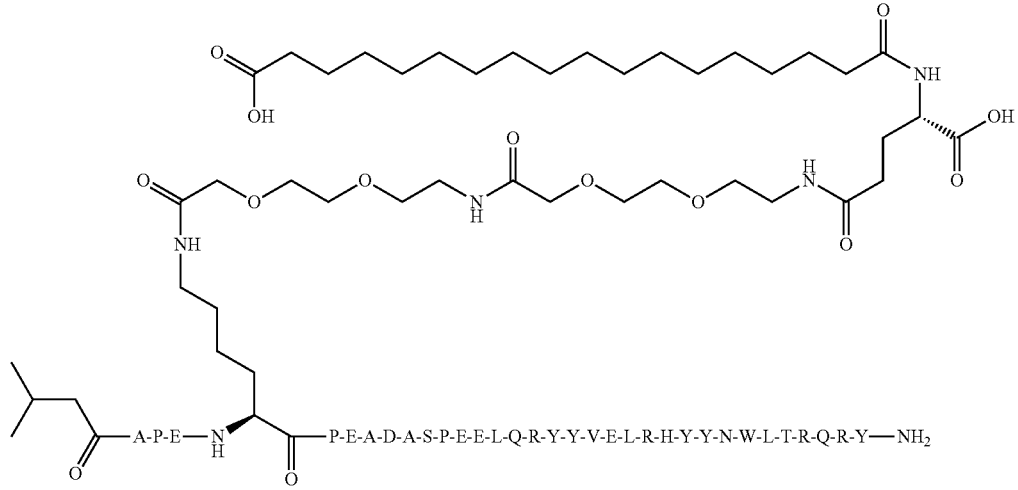

MW (calculated): 4971.6 Da
Synthesis and purification methods: S01; P01
LCMS: A01; Rt: 9.81 min; m/3: – m/4: 1244.0 m/5: -

Compound 136

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,12S,18Q,22V,28Y,30W,31L]hPYY(4-36) iVal-APEK(C18DA-gGlu-OEG1-OEG2-)PEADSSPEELQRYYVSLRHYYNWLTRQRY-NH2 (SEQ ID NO: 140)

MW (calculated): 4945.6 Da
Synthesis and purification methods: S01; P01
LCMS: A01; Rt: 9.79 min; m/3: 1649.0 m/4: – m/5: -

Compound 137

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,28Y,30W,31I]hPYY(4-36) iVal-APEK(C18DA-gGlu-OEG1-OEG2-)PEEDASPEELQRYYVSLRHYYNWITRQRY-NH2 (SEQ ID NO: 141)

MW (calculated): 4987.6 Da
Synthesis and purification methods: S01; P01
LCMS: A01; Rt: 9.56 min; m/3: 1664.0 m/4: – m/5: -

Compound 138

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,18Q,19Q,22V,28Y,30W,31L]hPYY(4-36) iVal-APAK(C18DA-gGlu-OEG1-OEG2-)PEEDASPEELQQYYVSLRHYYNWLTRQRY-NH2 (SEQ ID NO: 142)

MW (calculated): 4901.5 Da
Synthesis and purification methods: S01; P01
LCMS: A01; Rt: 10.03 min; m/3: – m/4: 1226.0 m/5: –

Compound 139

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,12S,18Q,22V,28Y,30W,31L]hPYY(4-36) iVal-APEK(C18DA-gGlu-OEG1-OEG2-)PEEESSPEELQRYYVSLRHYYNWLTRQRY-NH2 (SEQ ID NO: 143)

MW (calculated): 5017.6 Da
Synthesis and purification methods: S01; P01
LCMS: A01; Rt: 9.79 min; m/3: – m/4: 1256.0 m/5: -

Compound 140

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,18E,19Q,22V,28Y,30W,31L]hPYY(4-36) iVal-APEK(C18DA-gGlu-OEG1-OEG2-)PGEDASPEELEQYYVSLRHYYNWLTRQRY-NH2 (SEQ ID NO: 144)

MW (calculated): 4888.5 Da
Synthesis and purification methods: S01; P01
LCMS: A01; Rt: 10.01 min; m/3: – m/4: 1223.0 m/5: -

Compound 141

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18Q,22V,24A,28Y,30W,31L]hPYY(4-36) iVal-APEK(C18DA-gGlu-OEG1-OEG2-)PEEAASPEELQRYYVSARHYYNWLTRQRY-NH2 (SEQ ID NO: 145)

MW (calculated): 4901.5 Da
Synthesis and purification methods: S01; P01
LCMS: A01; Rt: 9.46 min; m/3: – m/4: 1227.0 m/5: -

Compound 142

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,11E,18Q,22V,28Y,30W,31L]hPYY(4-36) iVal-APEK(C18DA-gGlu-OEG1-OEG2-)PPEEASPEELQRYYVSLRHYYNWLTRQRY-NH2 (SEQ ID NO: 146)

MW (calculated): 4969.6 Da
Synthesis and purification methods: S01; P01
LCMS: A01; Rt: 9.79 min; m/3: – m/4: 1243.0 m/5: -

Compound 143

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13T,18Q,22V,23E,28Y,30W,31L]hPYY(4-36) iVal-APEK(C18DA-gGlu-OEG1-OEG2-)PEEDATPEELQRYYVALRHYYNWLTRQRY-NH2 (SEQ ID NO: 147)

MW (calculated): 4985.6 Da
Synthesis and purification methods: S01; P01
LCMS: A01; Rt: 10.10 min; m/3: – m/4: 1662.0 m/5: -

Compound 144

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,8A,9E,18Q,19Q,22V,28Y,30W,31L]hPYY(4-36) iVal-APEK(C18DA-gGlu-OEG1-OEG2-)AEEDASPEELQQYYVSLRHYYNWLTRQRY-NH2 (SEQ ID NO: 148)

MW (calculated): 4933.5 Da
Synthesis and purification methods: S01; P01
LCMS: A01; Rt: 10.14 min; m/3: 1645.0 m/4: – m/5: -

Compound 145

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,12S,17I,18Q,22V,28Y,30W,31L]hPYY(4-36) iVal-APEK(C18DA-gGlu-OEG1-OEG2-)PEEDSSPEEIQRYYVSLRHYYNWLTRQRY-NH2 (SEQ ID NO: 149)

MW (calculated): 5003.6 Da
Synthesis and purification methods: S01; P01
LCMS: A01; Rt: 9.74 min; m/3: – m/4: 1251.0 m/5: -

Compound 146

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,22V,24T,28Y,30W,31L]hPYY(4-36) iVal-APEK(C18DA-gGlu-OEG1-OEG2-)PEEEASPEELQRYYVSTRHYYNWLTRQRY-NH2 (SEQ ID NO: 150)

MW (calculated): 4989.6 Da
Synthesis and purification methods: S01; P01
LCMS: A01; Rt: 9.22 min; m/3: – m/4: 1248.0 m/5: -

Compound 147

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17T,18Q,22V,23E,28Y,30W,31L]hPYY(4-36) iVal-APEK(C18DA-gGlu-OEG1-OEG2-)PEEDASPEETQKYYVSLRHYYNWLTRQRY-NH2 (SEQ ID NO: 151)

MW (calculated): 4947.5 Da
Synthesis and purification methods: S03; P02
LCMS: A02; Rt: 9.18 min; m/3: 1650.3 m/4: 1238.1 m/5: 990.4

Compound 148

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13P,14A,18Q,22V,28Y,30W,31L]hPYY(4-36) iVal-APEK(C18DA-gGlu-OEG1-OEG2-)PEEDAPAEELQRYYVSLRHYYNWLTRQRY-NH2 (SEQ ID NO: 152)

MW (calculated): 4971.6 Da
Synthesis and purification methods: S01; P01
LCMS: A01; Rt: 11.20 min; m/3: – m/4: 1242.0 m/5: -

Compound 149

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11A,18Q,22V,23E,28Y,30W,31L]hPYY(4-36) iVal-APEK(C18DA-gGlu-OEG1-OEG2-)PEEAASPEELQRYYVELRHYYNWLTRQRY-NH2 (SEQ ID NO: 153)

MW (calculated): 4985.6 Da
Synthesis and purification methods: S01; P01
LCMS: A01; Rt: 9.99 min; m/3: – m/4: 1248.0 m/5: -

Compound 150

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,19K,22V,28Y,30W,31L]hPYY(4-36) iVal-APEK(C18DA-gGlu-OEG1-OEG2-)PEEDAEPEELQKYYVSLRHYYNWLTRQRY-NH2 (SEQ ID NO: 154)

MW (calculated): 5001.6 Da
Synthesis and purification methods: S03; P02
LCMS: A02; Rt: 11.23 min; m/3: 1668.7 m/4: 1251.5 m/5: 1001.2

Compound 151

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,11E,18Q,22V,28Y,30W,31L]hPYY(4-36) iVal-APEK(C18DA-gGlu-OEG1-OEG2-)PEAEASPEELQRYYVSLRHYYNWLTRQRY-NH2 (SEQ ID NO: 155)

MW (calculated): 4943.6 Da
Synthesis and purification methods: S01; P01
LCMS: A01; Rt: 9.87 min; m/3: – m/4: 1237.0 m/5: –

Compound 152

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,8A,9E,17I,18Q,22V,28Y,30W,31L]hPYY(4-36) iVal-APEK(C18DA-gGlu-OEG1-OEG2-)AEEDASPEEIQRYYVSLRHYYNWLTRQRY-NH2 (SEQ ID NO: 156)

MW (calculated): 4961.6 Da
Synthesis and purification methods: S01; P01
LCMS: A01; Rt: 9.95 min; m/3: 1654.0 m/4: – m/5: -

Compound 153

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,8V,9E,11E,18Q,22V,28Y,30W,31L]hPYY(4-36) iVal-APEK(C18DA-gGlu-OEG1-OEG2-)VEEEASPEELQRYYVSLRHYYNWLTRQRY-NH2 (SEQ ID NO: 157)

MW (calculated): 5003.7 Da
Synthesis and purification methods: S01; P01
LCMS: A01; Rt: 10.62 min; m/3: – m/4: – m/5: 1001

Compound 154

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,21E,22V,28Y,30W,31L]hPYY(4-36) iVal-APEK(C18DA-gGlu-OEG1-OEG2-)PEEEASPEELQRYEVSLRHYYNWLTRQRY-NH2 (SEQ ID NO: 158)

MW (calculated): 4967.6 Da
Synthesis and purification methods: S03; P02
LCMS: A02; Rt: 10.32 min; m/3: 1657.2 m/4: 1243.0 m/5: 994.4

Compound 155

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,17T,18Q,22V,23E,28Y,30W,31L]hPYY(4-36) iVal-APEK(C18DA-gGlu-OEG1-OEG2-)PEEDASPEETQRYYVSLRHYYNWLTRQRY-NH2 (SEQ ID NO: 159)

MW (calculated): 4975.6 Da
Synthesis and purification methods: S01; P01
LCMS: A01; Rt: 9.19 min; m/3: 1659.0 m/4: – m/5: -

Compound 156

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14E,18E,19Q,22V,28Y,30W,31L]hPYY(4-36) iVal-APEK(C18DA-gGlu-OEG1-OEG2-)PEEDASEEELEQYYVSLRHYYNWLTRQRY-NH2 (SEQ ID NO: 160)

MW (calculated): 4992.5 Da
Synthesis and purification methods: S02; P02
LCMS: A02; Rt: 13.23 min; m/3: 1665.6 m/4: 1248.9 m/5: 999.2

Compound 157

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9E,17T,18Q,22V,23E,28Y,30W,31L]hPYY(4-36) iVal-APAK(C18DA-gGlu-OEG1-OEG2-)PEEDASPEETQRYYVSLRHYYNWLTRQRY-NH2 (SEQ ID NO: 161)

MW (calculated): 4917.5 Da
Synthesis and purification methods: S01; P01
LCMS: A01; Rt: 9.28 min; m/3: 1640.0 m/4: – m/5: -

Compound 158

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,22V,28W,30Y,31L]hPYY(4-36) PEEDASPEELQRYYVSLRHYWNYLTRQRY-NH2 (SEQ ID NO: 162)

MW (calculated): 4987.6 Da
Synthesis and purification methods: S01; P01
LCMS: A01; Rt: 10.09 min; m/3: – m/4: 1248.0 m/5: -

Compound 159

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,18E,19Q,22V,28Y,30W,31L]hPYY(4-36) iVal-APEK(C18DA-gGlu-OEG1-OEG2-)PEADASPEELEQYYVSLRHYYNWLTRQRY-NH2 (SEQ ID NO: 163)

MW (calculated): 4902.5 Da
Synthesis and purification methods: S01; P01
LCMS: A01; Rt: 10.13 min; m/3: – m/4: 1226.0 m/5: -

Compound 160
N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,13E,18Q,22T,28Y,30W,31L]hPYY(4-36) iVal-APEK(C18DA-gGlu-OEG1-OEG2-) PEADAEPEELQRYYTSLRHYYNWLTRQRY-NH2 (sequence and structure below disclosed as SEQ ID NO: 164)
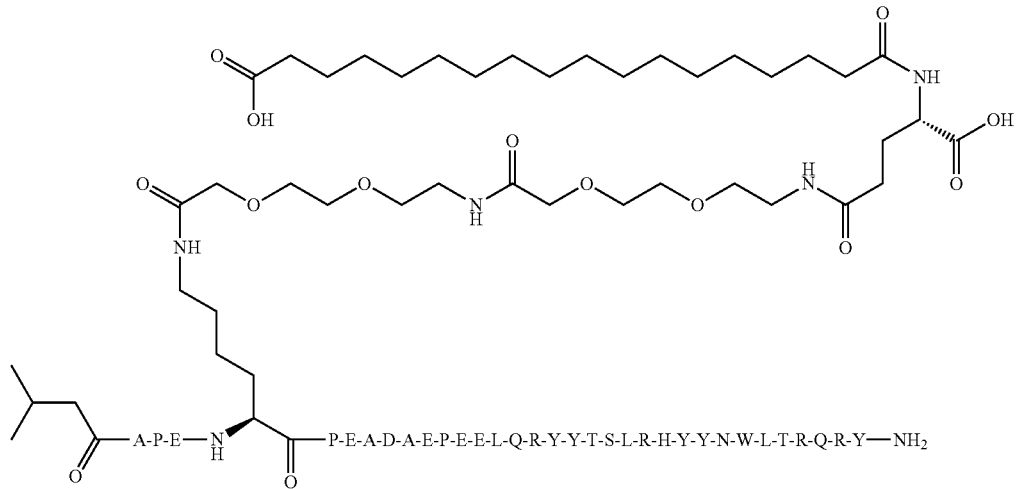
MW (calculated): 4973.6 Da
Synthesis and purification methods: S01; P01
LCMS: A01; Rt: 10.10 min; m/3: – m/4: 1244.0 m/5: –

Compound 161

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13T,18Q,22V,23E,28Y,30W,31L]hPYY(4-36) iVal-APEK(C18DA-gGlu-OEG1-OEG2-)PEEDATPEELQQYYVSLRHYYNWLTRQRY-NH2 (sequence and structure below disclosed as SEQ ID NO: 165)

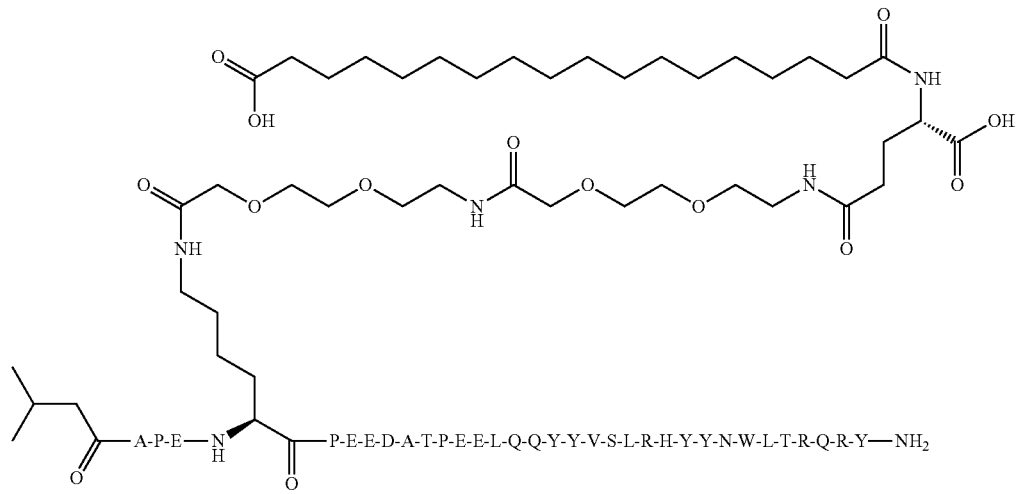

MW (calculated): 4973.6 Da
Synthesis and purification methods: S03; P02
LCMS: A02; Rt: 11.90 min; m/3: 1658.2 m/4: 1244.5 m/5: 995.7

Compound 162

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,21E,22V,26A,28Y,30W,31L]hPYY(4-36) iVal-APEK(C18DA-gGlu-OEG1-OEG2-)PEEDASPEELQRYEVSLRAYYNWLTRQRY-NH2 (SEQ ID NO: 166)

MW (calculated): 4887.5 Da
Synthesis and purification methods: S03; P02
LCMS: A02; Rt: 11.22 min; m/3: 1630.5 m/4: 1223.0 m/5: 978.3

Compound 163

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18Q,22V,23A,28Y,30W,31L]hPYY(4-36)PEEAASPEELQRYYVALRHYYNWLTRQRY-NH2 (SEQ ID NO: 167)

MW (calculated): 4927.6 Da
Synthesis and purification methods: S01; P01
LCMS: A01; Rt: 10.16 min; m/3: – m/4: 1234.0 m/5: -

Compound 164

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,18Q,19E,22V,28Y,30W,31L]hPYY(4-36) iVal-APEK(C18DA-gGlu-OEG1-OEG2-)PEEDASEEELQEYYVSLRHYYNWLTRQRY-NH2 (SEQ ID NO: 168)

MW (calculated): 4992.5 Da
Synthesis and purification methods: S01; P01
LCMS: A01; Rt: 10.65 min; m/3: 1665.0 m/4: – m/5: -

Compound 165

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,21Q,22V,28Y,30W,31L]hPYY(4-36) iVal-APEK(C18DA-gGlu-OEG1-OEG2-)PEEDASPEELQRYQVSLRHYYNWLTRQRY-NH2 (SEQ ID NO: 169)

MW (calculated): 4952.6 Da
Synthesis and purification methods: S01; P01
LCMS: A01; Rt: 9.26 min; m/3: – m/4: 1239.0 m/5: -

93

Compound 166

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9P,10A,18Q,22V,23E,28Y,30W,31L]hPYY(4-36) iVal-APEK(C18DA-gGlu-OEG1-OEG2-)PPADASPEELQRYYVELRHYYNWLTRQRY-NH2 (SEQ ID NO: 170)

MW (calculated): 4939.6 Da
Synthesis and purification methods: S01; P01
LCMS: A01; Rt: 9.58 min; m/3: 1647.0 m/4: – m/5: -

Compound 167

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,18Q,19Q,21E,22V,28Y,30W,31L]hPYY(4-36) iVal-APEK(C18DA-gGlu-OEG1-OEG2-)PEEDASPEELQQYEVSLRHYYNWLTRQRY-NH2 (SEQ ID NO: 171)

MW (calculated): 4925.5 Da
Synthesis and purification methods: S03; P02
LCMS: A02; Rt: 10.95 min; m/3: 1643.1 m/4: 1232.5 m/5: 985.5

Compound 168

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,18Q,22V,28Y,30W,31I]hPYY(4-36) iVal-APEK(C18DA-gGlu-OEG1-OEG2-)PEEDAEPEELQRYYVSLRHYYNWITRQRY-NH2 (SEQ ID NO: 172)

MW (calculated): 5029.6 Da
Synthesis and purification methods: S01; P01
LCMS: A01; Rt: 9.66 min; m/3: 1678.0 m/4: – m/5: -

94

Compound 169

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,22V,23A,28Y,30W,31L]hPYY(4-36) iVal-APEK(C18DA-gGlu-OEG1-OEG2-)PEEEASPEELQRYYVALRHYYNWLTRQRY-NH2 (SEQ ID NO: 173)

MW (calculated): 4985.6 Da
Synthesis and purification methods: S01; P01
LCMS: A01; Rt: 9.96 min; m/3: 1663.0 m/4: – m/5: –

Compound 170

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18E,19Q,22V,28Y,30W,31L]hPYY(4-36) iVal-APEK(C18DA-gGlu-OEG1-OEG2-)PEEEASPEELEQYYVSLRHYYNWLTRQRY-NH2 (SEQ ID NO: 174)

MW (calculated): 4974.6 Da
Synthesis and purification methods: S01; P01
LCMS: A01; Rt: 10.18 min; m/3: – m/4: 1244.0 m/5: -

Compound 171

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13T,18Q,22V,23E,28Y,30W,31L]hPYY(4-36) iVal-APEK(C18DA-gGlu-OEG1-OEG2-)PEEDATPEEIQRYYVSLRHYYNWLTRQRY-NH2 (sequence and structure below disclosed as SEQ ID NO: 175)

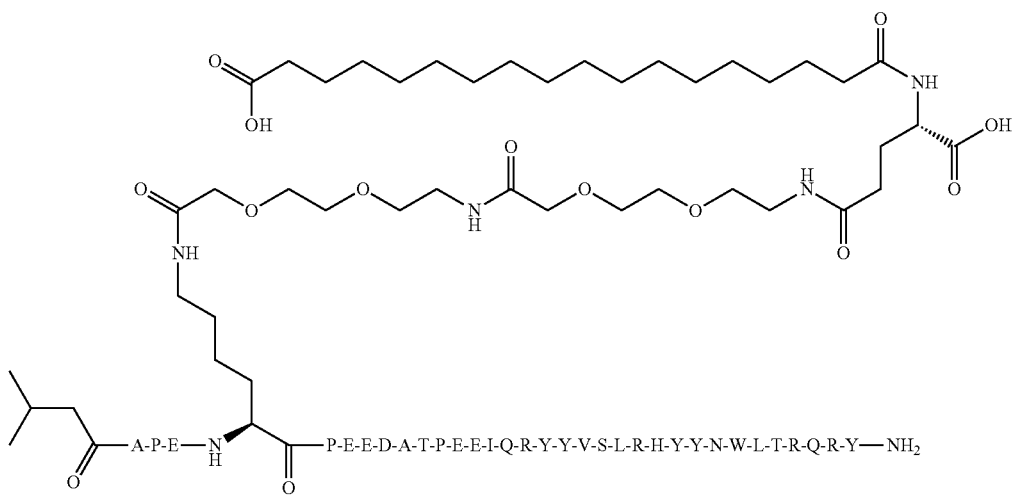

MW (calculated): 5001.6 Da
Synthesis and purification methods: S01; P01
LCMS: A01; Rt: 9.82 min; m/3: – m/4: 1251.0 m/5: -

Compound 172

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13E,18Q,22V,23A,28Y,30W,31L]hPYY(4-36)
PEEDAEPEELQRYYVALRHYYNWLTRQRY-NH2 (SEQ ID NO: 176)

MW (calculated): 5013.6 Da
Synthesis and purification methods: S03; P02
LCMS: A02; Rt: 12.87 min; m/3: 1672.6 m/4: 1254.6 m/5: 1003.6

Compound 173

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,18Q,22V,23E,28Y,30W,31L]hPYY(4-36) iVal-APAK (C18DA-gGlu-OEG1-OEG2-)
PEEDASPEELQRYYVELRHYYNWLTRQRY-NH2 (SEQ ID NO: 177)

MW (calculated): 4971.6 Da
Synthesis and purification methods: S01; P01
LCMS: A01; Rt: 9.91 min; m/3: – m/4: 1245.0 m/5: -

Compound 174

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,13E,18Q,22V,28Y,30W,31L]hPYY(4-36) iVal-APAK (C18DA-gGlu-OEG1-OEG2-)
PEEDAEPEELQRYYVSLRHYYNWLTRQRY-NH2 (SEQ ID NO: 178)

MW (calculated): 4971.6 Da
Synthesis and purification methods: S01; P01
LCMS: A01; Rt: 10.27 min; m/3: – m/4: 1244.0 m/5: -

Compound 175

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,18Q,22V,23A,28Y,30W,31L]hPYY(4-36) iVal-APEK (C18DA-gGlu-OEG1-OEG2-)
PEEDAAPEELQRYYVALRHYYNWLTRQRY-NH2 (SEQ ID NO: 179)

MW (calculated): 4955.6 Da
Synthesis and purification methods: S01; P01
LCMS: A01; Rt: 10.87 min; m/3: 1653.0 m/4: – m/5: -

Compound 176

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,18Q,22V,28Y,30W,31L]hPYY(4-36) iVal-APEK (C18DA-gGlu-OEG1-OEG2-)
PEEDASEEELQRYYVSLRHYYNWLTRQRY-NH2 (SEQ ID NO: 180)

MW (calculated): 5019.6 Da
Synthesis and purification methods: S01; P01
LCMS: A01; Rt: 10.40 min; m/3: 1674.0 m/4: – m/5: -

Compound 177

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,18Q,22V,23E,28Y,30W,31L]hPYY(4-36) iVal-APEK (C18DA-gGlu-OEG1-OEG2-)
PEEDSSPEELQRYYVELRHYYNWLTRQRY-NH2 (SEQ ID NO: 181)

MW (calculated): 5045.6 Da
Synthesis and purification methods: S01; P01
LCMS: A01; Rt: 9.85 min; m/3: – m/4: 1262.0 m/5: -

Compound 178

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13T,18Q,22V,23E,28Y,30W,31L]hPYY(4-36) iVal-APEK (C18DA-gGlu-OEG1-OEG2-)
PEEDATPEETERYYVSLRHYYNWLTRQRY-NH2 (SEQ ID NO: 182)

MW (calculated): 4990.6 Da
Synthesis and purification methods: S01; P01
LCMS: A01; Rt: 9.35 min; m/3: – m/4: 1249.0 m/5: –

Compound 179

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,15A,18Q,22V,28Y,30W,31L]hPYY(4-36) iVal-APAK (C18DA-gGlu-OEG1-OEG2-)
PEEDASPAELQRYYVSLRHYYNWLTRQRY-NH2 (SEQ ID NO: 183)

MW (calculated): 4871.5 Da
Synthesis and purification methods: S01; P01
LCMS: A01; Rt: 9.96 min; m/3: 1625.0 m/4: – m/5: -

Compound 180

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17T,18Q, 19Q,22V,28Y,30W,31L]hPYY(4-36) iVal-APEK (C18DA-gGlu-OEG1-OEG2-) PEEDASPEETQQYYVSLRHYYNWLTRQRY-NH2 (SEQ ID NO: 184)

MW (calculated): 4947.5 Da
Synthesis and purification methods: S01; P01
LCMS: A01; Rt: 9.27 min; m/3: 1650.0 m/4: – m/5: -

Compound 181

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,10A,18Q, 22V,23A,28Y,30W,31L]hPYY(4-36) iVal-APEK (C18DA-gGlu-OEG1-OEG2-) PEADASPEELQRYYVALRHYYNWLTRQRY-NH2 (SEQ ID NO: 185)

MW (calculated): 4913.6 Da
Synthesis and purification methods: S01; P01
LCMS: A01; Rt: 9.93 min; m/3: – m/4: 1229.0 m/5: -

Compound 182

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12G,18Q, 22V,23E,28Y,30W,31L]hPYY(4-36) iVal-APEK (C18DA-gGlu-OEG1-OEG2-) PEEDGSPEELQRYYVELRHYYNWLTRQRY-NH2 (SEQ ID NO: 186)

MW (calculated): 5015.6 Da
Synthesis and purification methods: S01; P01
LCMS: A01; Rt: 11.02 min; m/3: 1672.0 m/4: – m/5: -

Compound 183

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9P,18Q,22V, 28Y,30W,31L]hPYY(4-36) iVal-APEK(C18DA-gGlu-OEG1-OEG2-) PPEDASPEELQRYYVSLRHYYNWLTRQRY-NH2 (SEQ ID NO: 187)

MW (calculated): 4955.6 Da
Synthesis and purification methods: S01; P01
LCMS: A01; Rt: 9.46 min; m/3: 1652.0 m/4: – m/5: -

Compound 184

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18Q, 22V,23T,28Y,30W,31L]hPYY(4-36) iVal-APEK (C18DA-gGlu-OEG1-OEG2-) PEEAASPEELQRYYVTLRHYYNWLTRQRY-NH2 (SEQ ID NO: 188)

MW (calculated): 4957.6 Da
Synthesis and purification methods: S01; P01
LCMS: A01; Rt: 10.13 min; m/3: – m/4: 1241.0 m/5: -

Compound 185

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,18Q, 22V,23E,28Y,30W,31L]hPYY(4-36) PEEEASPEELQRYYVELRHYYNWLTRQRY-NH2 (SEQ ID NO: 189)

MW (calculated): 5043.7 Da
Synthesis and purification methods: S01; P01
LCMS: A01; Rt: 9.83 min; m/3: 1683.0 m/4: – m/5: -

Compound 186

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q, 22V,23E,28Y,30W,31L]hPYY(4-36) iVal-APEK (C18DA-gGlu-OEG1-OEG2-) PEEDASAEELQRYYVELRHYYNWLTRQRY-NH2 (SEQ ID NO: 190)

MW (calculated): 5003.6 Da
Synthesis and purification methods: S01; P01
LCMS: A01; Rt: 10.55 min; m/3: – m/4: 1252.0 m/5: -

Compound 187

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V, 27Q,28Y,30W,31L]hPYY(4-36) iVal-APEK (C18DA-gGlu-OEG1-OEG2-) PEEDASPEELQRYYVSLRHQYNWLTRQRY-NH2 (SEQ ID NO: 191)

MW (calculated): 4952.6 Da
Synthesis and purification methods: S01; P01
LCMS: A01; Rt: 9.22 min; m/3: 1652.0 m/4: – m/5: -

Compound 188

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13E,18Q, 22V,28Y,30W,31L]hPYY(4-36) iVal-APEK (C18DA-gGlu-OEG1-OEG2-) PEEDAEPEELQRYYVSLRHYYNWLTRQRY-NH2 (SEQ ID NO: 192)

MW (calculated): 5031.7 Da
Synthesis and purification methods: S01; P01
LCMS: A01; Rt: 9.87 min; m/3: – m/4: 1257.0 m/5: -

Compound 189

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,15A, 18Q,22V,28Y,30W,31L]hPYY(4-36) iVal-APEK (C18DA-gGlu-OEG1-OEG2-) PEEDASEAELQRYYVSLRHYYNWLTRQRY-NH2 (SEQ ID NO: 193)

MW (calculated): 4961.6 Da
Synthesis and purification methods: S01; P01
LCMS: A01; Rt: 10.40 min; m/3: – m/4: 1241.0 m/5: -

Compound 190

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,13P, 18Q,22V,28Y,30W,31L]hPYY(4-36) iVal-APEK (C18DA-gGlu-OEG1-OEG2-) PEEEAPPEELQRYYVSLRHYYNWLTRQRY-NH2 (SEQ ID NO: 194)

MW (calculated): 5011.7 Da
Synthesis and purification methods: S01; P01
LCMS: A01; Rt: 10.32 min; m/3: – m/4: 1254.0 m/5: -

Compound 191

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22I, 28Y,30W,31L]hPYY(4-36) iVal-APEK(C18DA-gGlu-OEG1-OEG2-) PEEDASPEELQRYYISLRHYYNWLTRQRY-NH2 (SEQ ID NO: 195)

MW (calculated): 5001.6 Da
Synthesis and purification methods: S01; P01
LCMS: A01; Rt: 9.81 min; m/3: 1668.0 m/4: – m/5: –

Compound 192

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13A,15A, 18Q,22V,28Y,30W,31L]hPYY(4-36) iVal-APEK (C18DA-gGlu-OEG1-OEG2-) PEEDAAPAELQRYYVSLRHYYNWLTRQRY-NH2 (sequence and structure below disclosed as SEQ ID NO: 196)

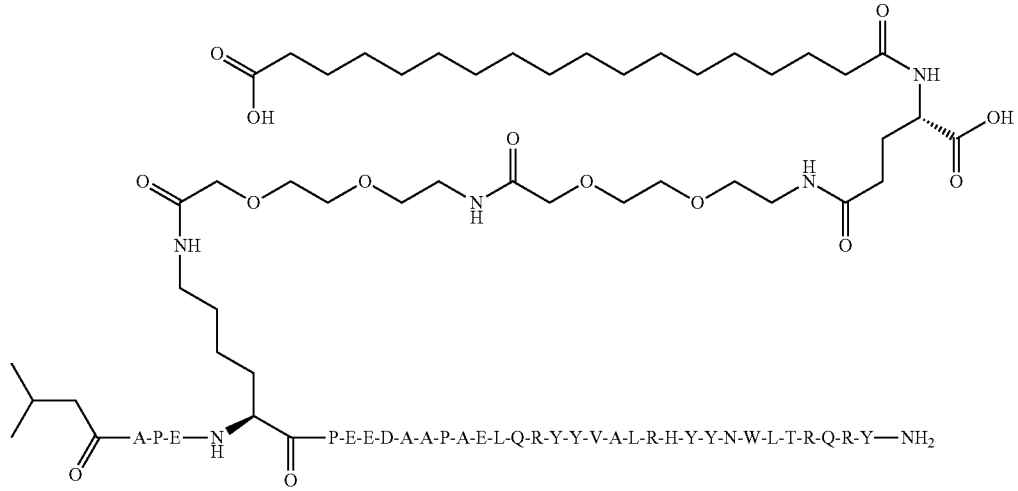

MW (calculated): 4913.6 Da
Synthesis and purification methods: S01; P01
LCMS: A01; Rt: 10.60 min; m/3: – m/4: 1229.0 m/5: -

Compound 193

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,14E,17I,
18Q,22V,28Y,30W,31L]hPYY(4-36) iVal-APEK
(C18DA-gGlu-OEG1-OEG2-)
PEEDASEEEIQRYYVSLRHYYNWLTRQRY-NH2
(SEQ ID NO: 197)

MW (calculated): 5019.6 Da
Synthesis and purification methods: S01; P01
LCMS: A01; Rt: 10.37 min; m/3: 1674.0 m/4: – m/5: -

Compound 194

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,5Hyp,7K,9E,18Q,
22V,28Y,30W,31T,32L]hPYY(4-36) iVal-AHypEK
(C18DA-gGlu-OEG1-OEG2-)
PEEDASPEELQRYYVSLRHYYNWTLRQRY-
NH2 (SEQ ID NO: 198)

MW (calculated): 5003.6 Da
Synthesis and purification methods: S01; P01
LCMS: A01; Rt: 8.84 min; m/3: – m/4: 1252.0 m/5: -

Compound 195

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,16A,18Q,
22V,23E,28Y,30W,31L]hPYY(4-36) iVal-APEK
(C18DA-gGlu-OEG1-OEG2-)
PEEDASPEALQRYYVELRHYYNWLTRQRY-
NH2 (SEQ ID NO: 199)

MW (calculated): 4971.6 Da
Synthesis and purification methods: S01; P01
LCMS: A01; Rt: 10.11 min; m/3: 1658.0 m/4: – m/5: -

Compound 196

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,6A,7K,9P,13E,18Q,
22V,28Y,30W,31L]hPYY(4-36) iVal-APAK
(C18DA-gGlu-OEG1-OEG2-)
PPEDAEPEELQRYYVSLRHYYNWLTRQRY-
NH2 (SEQ ID NO: 200)

MW (calculated): 4939.6 Da
Synthesis and purification methods: S01; P01
LCMS: A01; Rt: 10.28 min; m/3: – m/4: 1236.0 m/5: -

Compound 197

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,6A,7K,9E,10A,
18Q,22V,23E,28Y,30W,31L]hPYY(4-36) iVal-
APAK(C18DA-gGlu-OEG1-OEG2-)
PEADASPEELQRYYVELRHYYNWLTRQRY-
NH2 (SEQ ID NO: 201)

MW (calculated): 4913.6 Da
Synthesis and purification methods: S01; P01
LCMS: A01; Rt: 10.00 min; m/3: 1639.0 m/4: m/5: –

Compound 198

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,13E,16A,
18Q,22V,28Y,30W,31L]hPYY(4-36) iVal-APEK
(C18DA-gGlu-OEG1-OEG2-)
PEEDAEPEALQRYYVSLRHYYNWLTRQRY-
NH2 (SEQ ID NO: 202)

MW (calculated): 4971.6 Da
Synthesis and purification methods: S01; P01
LCMS: A01; Rt: 10.31 min; m/3: – m/4: 1244.0 m/5: -

Compound 199

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,9E,13E,17T,
18Q,22V,28Y,30W,31L]hPYY(4-36) iVal-APEK
(C18DA-gGlu-OEG1-OEG2-)
PEEDAEPEETQRYYVSLRHYYNWLTRQRY-
NH2 (SEQ ID NO: 203)

MW (calculated): 5017.6 Da
Synthesis and purification methods: S01; P01
LCMS: A01; Rt: 9.37 min; m/3: – m/4: 1255.0 m/5: -

Compound 200

N{alpha-4}-(3-methylbutanoyl)-N{epsilon-7}-[2-(2-
{2-[2-(2-{2-[(4S)-4-carboxy-4-(17-carboxyheptade-
canamido)butanamido]ethoxy}ethoxy)acetamido]
ethoxy}ethoxy) acetamido]-[4A,7K,8Hyp,9E,18Q,
22V,28Y,30W,31L]hPYY(4-36) iVal-APEK
(C18DA-gGlu-OEG1-OEG2-)
HypEEDASPEELQRYYVSLRHYYNWLTRQRY-
NH2 (SEQ ID NO: 204)

MW (calculated): 5003.6 Da
Synthesis and purification methods: S01; P01
LCMS: A01; Rt: 9.53 min; m/3: – m/4: 1250.0 m/5: -

Compound 201

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9Q,13E,18Q,19E,22V,28Y,30W,31L]hPYY(4-36) iVal-APEK(C18DA-gGlu-OEG1-OEG2-)PQEDAEPEELQEYYVSLRHYYNWLTRQRY-NH2 (SEQ ID NO: 205)

MW (calculated): 5001.6 Da
Synthesis and purification methods: S01; P01
LCMS: A01; Rt: 10.24 min; m/3: – m/4: 1251.0 m/5: -

Compound 202

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13A,18Q,19K,22V,28Y,30W,31L]hPYY(4-36) iVal-APEK(C18DA-gGlu-OEG1-OEG2-)PEEDAAPEELQKYYVSLRHYYNWLTRQRY-NH2 (SEQ ID NO: 206)

MW (calculated): 4943.6 Da
Synthesis and purification methods: S01; P01
LCMS: A01; Rt: 10.48 min; m/3: – m/4: 1237.0 m/5: -

Compound 203

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,6A,7K,9E,18Q,22V,28Y,30W,31L]hPYY(4-36) iVal-APAK(C18DA-gGlu-OEG1-OEG2-)PEEDASPEELQRYYVSLRHYYNWLTRQRY-NH2 (sequence and structure below disclosed as SEQ ID NO: 207)

MW (calculated): 4929.6 Da
Synthesis and purification methods: S01; P01
LCMS: A01; Rt: 9.83 min; m/3: – m/4: 1644.0 m/5: -

Compound 204

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,17V,18Q,22V,28Y,30W,31L]hPYY(4-36) iVal-APEK(C18DA-gGlu-OEG1-OEG2-)PEEEASPEEVQRYYVSLRHYYNWLTRQRY-NH2 (SEQ ID NO: 208)

MW (calculated): 4987.6 Da
Synthesis and purification methods: S01; P01
LCMS: A01; Rt: 9.62 min; m/3: – m/4: 1663.0 m/5: -

Compound 205

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,19K,22V,28Y,30W,31L]hPYY(4-36) iVal-APEK(C18DA-gGlu-OEG1-OEG2-)PEEEASPEELQKYYVSLRHYYNWLTRQRY-NH2 (SEQ ID NO: 209)

MW (calculated): 4973.6 Da
Synthesis and purification methods: S03; P02
LCMS: A02; Rt: 11.05 min; m/3: 1659.2 m/4: 1244.4 m/5: 995.5

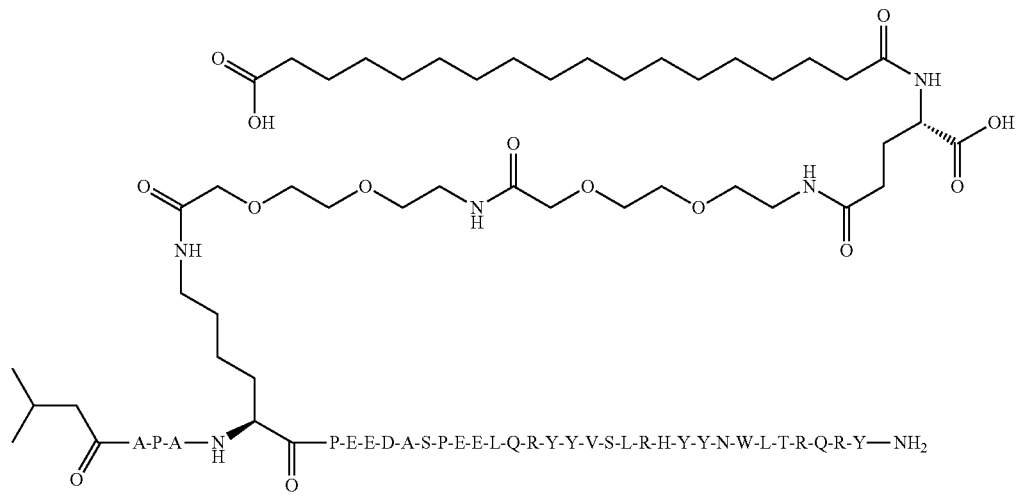

Compound 206

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18E,19Q,21E,22V,28Y,30W,31L]hPYY(4-36) iVal-APEK(C18DA-gGlu-OEG1-OEG2-)PEEDASPEELEQYEVSLRHYYNWLTRQRY-NH2 (SEQ ID NO: 210)

MW (calculated): 4926.5 Da
Synthesis and purification methods: S02; P02
LCMS: A02; Rt: 11.60 min; m/3: 1643.3 m/4: 1232.8 m/5: 986.2

Compound 207

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,10A,13E,18Q,22V,28Y,30W,31L]hPYY(4-36) iVal-APAK(C18DA-gGlu-OEG1-OEG2-)PEADAEPEELQRYYVSLRHYYNWLTRQRY-NH2 (SEQ ID NO: 211)

MW (calculated): 4913.6 Da
Synthesis and purification methods: S01; P01
LCMS: A01; Rt: 10.37 min; m/3: – m/4: 1229.0 m/5: -

Compound 208

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,17T,18Q,22V,28Y,30W,31L]hPYY(4-36) iVal-APEK(C18DA-gGlu-OEG1-OEG2-)PEEDASEEETQRYYVSLRHYYNWLTRQRY-NH2 (SEQ ID NO: 212)

MW (calculated): 5007.6 Da
Synthesis and purification methods: S01; P01
LCMS: A01; Rt: 9.63 min; m/3: 1670.0 m/4: – m/5: -

Compound 209

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,13E,18Q,22V,28Y,30W,31L]hPYY(4-36)PEEDSEPEELQRYYVSLRHYYNWLTRQRY-NH2 (SEQ ID NO: 213)

MW (calculated): 5045.6 Da
Synthesis and purification methods: S01; P01
LCMS: A01; Rt: 10.09 min; m/3: – m/4: 1263.0 m/5: -

Compound 210

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8I,9E,11E,18Q,22V,28Y,30W,31L]hPYY(4-36) iVal-APEK(C18DA-gGlu-OEG1-OEG2-)IEEEASPEELQRYYVSLRHYYNWLTRQRY-NH2 (SEQ ID NO: 214)

MW (calculated): 5017.7 Da
Synthesis and purification methods: S01; P01
LCMS: A01; Rt: 11.05 min; m/3: – m/4: 1255.0 m/5: -

Compound 211

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13T,14A,18Q,22V,28Y,30W,31L]hPYY(4-36) iVal-APEK(C18DA-gGlu-OEG1-OEG2-)PEEDATAEELQRYYVSLRHYYNWLTRQRY-NH2 (SEQ ID NO: 215)

MW (calculated): 4975.6 Da
Synthesis and purification methods: S01; P01
LCMS: A01; Rt: 10.92 min; m/3: – m/4: 1245.0 m/5: -

Compound 212

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12T,13A,18Q,22V,28Y,30W,31L]hPYY(4-36) iVal-APEK(C18DA-gGlu-OEG1-OEG2-)PEEDTAPEELQRYYVSLRHYYNWLTRQRY-NH2 (SEQ ID NO: 216)

MW (calculated): 5001.6 Da
Synthesis and purification methods: S01; P01
LCMS: A01; Rt: 10.56 min; m/3: – m/4: 1251.0 m/5: -

Compound 213

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,12T,18Q,22V,28Y,30W,31L]hPYY(4-36) iVal-APEK(C18DA-gGlu-OEG1-OEG2-)PEEETSPEELQRYYVSLRHYYNWLTRQRY-NH2 (SEQ ID NO: 217)

MW (calculated): 5031.7 Da
Synthesis and purification methods: S01; P01
LCMS: A01; Rt: 9.79 min; m/3: 1678.0 m/4: – m/5: -

Compound 214

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14E,18Q,22V,23A,28Y,30W,31L]hPYY(4-36) iVal-APEK (C18DA-gGlu-OEG1-OEG2-) PEEDASEEELQRYYVALRHYYNWLTRQRY-NH2 (SEQ ID NO: 218)

MW (calculated): 5003.6 Da
Synthesis and purification methods: S01; P01
LCMS: A01; Rt: 10.70 min; m/3: 1668.0 m/4: – m/5: -

Compound 215

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,15A,18Q,22V,23E,28Y,30W,31L]hPYY(4-36) iVal-APEK (C18DA-gGlu-OEG1-OEG2-) PEEDASPAELQRYYVELRHYYNWLTRQRY-NH2 (SEQ ID NO: 219)

MW (calculated): 4971.6 Da
Synthesis and purification methods: S01; P01
LCMS: A01; Rt: 9.86 min; m/3: – m/4: 1244.0 m/5: –

Compound 216

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,18E,19Q,22V,28Y,30W,31L]hPYY(4-36) iVal-APAK (C18DA-gGlu-OEG1-OEG2-) PEEDASPEELEQYYVSLRHYYNWLTRQRY-NH2 (SEQ ID NO: 220)

MW (calculated): 4902.5 Da
Synthesis and purification methods: S01; P01
LCMS: A01; Rt: 10.24 min; m/3: 1635.0 m/4: – m/5: -

Compound 217

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,15A,18Q,22V,23A,28Y,30W,31L]hPYY(4-36) iVal-APEK (C18DA-gGlu-OEG1-OEG2-) PEEDASPAELQRYYVALRHYYNWLTRQRY-NH2 (SEQ ID NO: 221)

MW (calculated): 4913.6 Da
Synthesis and purification methods: S01; P01
LCMS: A01; Rt: 9.99 min; m/3: 1639.0 m/4: m/5: -

Compound 218

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,12S,18Q,22V,23A,28Y,30W,31L]hPYY(4-36) iVal-APEK (C18DA-gGlu-OEG1-OEG2-) PEEDSSPEELQRYYVALRHYYNWLTRQRY-NH2 (SEQ ID NO: 222)

MW (calculated): 4987.6 Da
Synthesis and purification methods: S01; P01
LCMS: A01; Rt: 10.00 min; m/3: – m/4: 1247.0 m/5: -

Compound 219

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,13A,18Q,22V,28Y,30W,31L]hPYY(4-36) iVal-APEK (C18DA-gGlu-OEG1-OEG2-) PEEEAAPEELQRYYVSLRHYYNWLTRQRY-NH2 (SEQ ID NO: 223)

MW (calculated): 4985.6 Da
Synthesis and purification methods: S01; P01
LCMS: A01; Rt: 10.41 min; m/3: – m/4: 1247.0 m/5: -

Compound 220

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,14A,18Q,22V,28Y,30W,31L]hPYY(4-36) iVal-APEK (C18DA-gGlu-OEG1-OEG2-) PEEAASAEELQRYYVSLRHYYNWLTRQRY-NH2 (SEQ ID NO: 224)

MW (calculated): 4917.6 Da
Synthesis and purification methods: S01; P01
LCMS: A01; Rt: 10.70 min; m/3: – m/4: 1230.0 m/5: -

Compound 221

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13P,14E,18Q,22V,28Y,30W,31L]hPYY(4-36) iVal-APEK (C18DA-gGlu-OEG1-OEG2-) PEEDAPEEELQRYYVSLRHYYNWLTRQRY-NH2 (sequence and structure below disclosed as SEQ ID NO: 225)

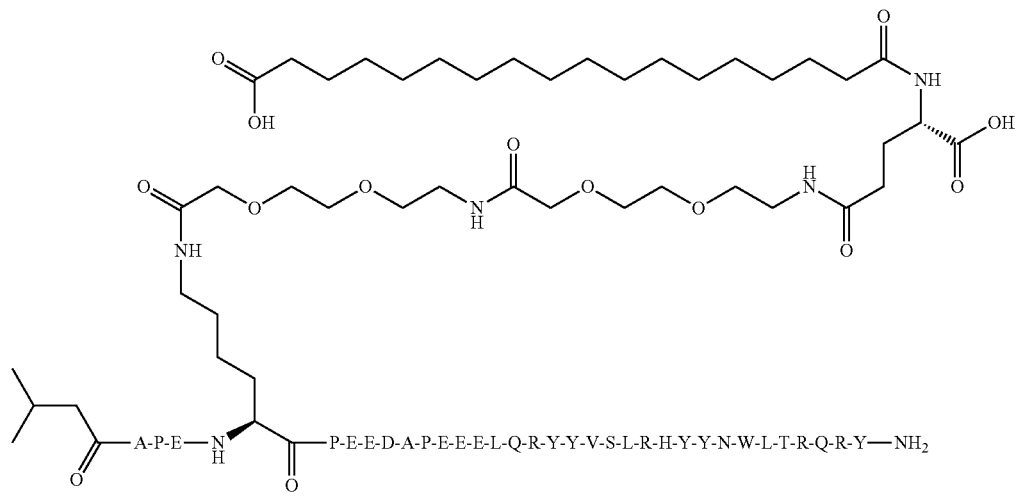

MW (calculated): 5029.6 Da
Synthesis and purification methods: S01; P01
LCMS: A01; Rt: 11.00 min; m/3: – m/4: 1258.0 m/5: –

Compound 222

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14A,18Q,19Q,22V,28Y,30W,31L]hPYY(4-36) iVal-APEK (C18DA-gGlu-OEG1-OEG2-) PEEDASAEELQQYYVSLRHYYNWLTRQRY-NH2 (SEQ ID NO: 226)

MW (calculated): 4933.5 Da
Synthesis and purification methods: S02; P02
LCMS: A02; Rt: 13.32 min; m/3: 1645.5 m/4: 1234.4 m/5: 987.4

Compound 223

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,13E,18Q,22V,28Y,30W,31L]hPYY(4-36) iVal-APEK (C18DA-gGlu-OEG1-OEG2-) PEEAAEPEELQRYYVSLRHYYNWLTRQRY-NH2 (SEQ ID NO: 227)

MW (calculated): 4985.6 Da
Synthesis and purification methods: S01; P01
LCMS: A01; Rt: 10.21 min; m/3: – m/4: 1247.0 m/5: –

Compound 224

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,11E,18E,19Q,22V,28Y,30W,31L]hPYY(4-36) iVal-APEK (C18DA-gGlu-OEG1-OEG2-) PGEEASPEELEQYYVSLRHYYNWLTRQRY-NH2 (SEQ ID NO: 228)

MW (calculated): 4902.5 Da
Synthesis and purification methods: S01; P01
LCMS: A01; Rt: 10.12 min; m/3: 1634.0 m/4: – m/5: –

Compound 225

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,13E,18E,19Q,22V,28Y,30W,31L]hPYY(4-36) iVal-APEK (C18DA-gGlu-OEG1-OEG2-) PGEDAEPEELEQYYVSLRHYYNWLTRQRY-NH2 (SEQ ID NO: 229)

MW (calculated): 4930.5 Da
Synthesis and purification methods: S01; P01
LCMS: A01; Rt: 9.96 min; m/3: 1644.0 m/4: – m/5: –

Compound 226

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,17T,18Q,22V,28Y,30W,31L]hPYY(4-36) iVal-APEK(C18DA-gGlu-OEG1-OEG2-)PEEAASPEETQRYYVSLRHYYNWLTRQRY-NH2 (SEQ ID NO: 230)

MW (calculated): 4931.5 Da
Synthesis and purification methods: S01; P01
LCMS: A01; Rt: 9.26 min; m/3: 1645.0 m/4: – m/5: -

Compound 227

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8A,9E,18E,19Q,22V,28Y,30W,31L]hPYY(4-36) iVal-APEK(C18DA-gGlu-OEG1-OEG2-)AEEDASPEELEQYYVSLRHYYNWLTRQRY-NH2 (SEQ ID NO: 231)

MW (calculated): 4934.5 Da
Synthesis and purification methods: S01; P01
LCMS: A01; Rt: 10.38 min; m/3: – m/4: 1235.0 m/5: -

Compound 228

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,19Q,22V,26A,28Y,30W,31L]hPYY(4-36) iVal-APEK(C18DA-gGlu-OEG1-OEG2-)PEEDASPEELQQYYVSLRAYYNWLTRQRY-NH2 (SEQ ID NO: 232)

MW (calculated): 4893.5 Da
Synthesis and purification methods: S03; P02

LCMS: A02; Rt: 12.98 min; m/3: 1632.6 m/4: 1224.3 m/5: 979.6

Compound 229

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,24A,28Y,30W,31L]hPYY(4-36) iVal-APEK(C18DA-gGlu-OEG1-OEG2-)PEEDASPEELQRYYVSARHYYNWLTRQRY-NH2 (SEQ ID NO: 233)

MW (calculated): 4945.5 Da
Synthesis and purification methods: S01; P01
LCMS: A01; Rt: 9.27 min; m/3: 1650.0 m/4: – m/5: -

Compound 230

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,17I,18Q,22V,23A,28Y,30W,31L]hPYY(4-36) iVal-APEK(C18DA-gGlu-OEG1-OEG2-)PEEDASPEEIQRYYVALRHYYNWLTRQRY-NH2 (sequence and structure below disclosed as SEQ ID NO: 234)

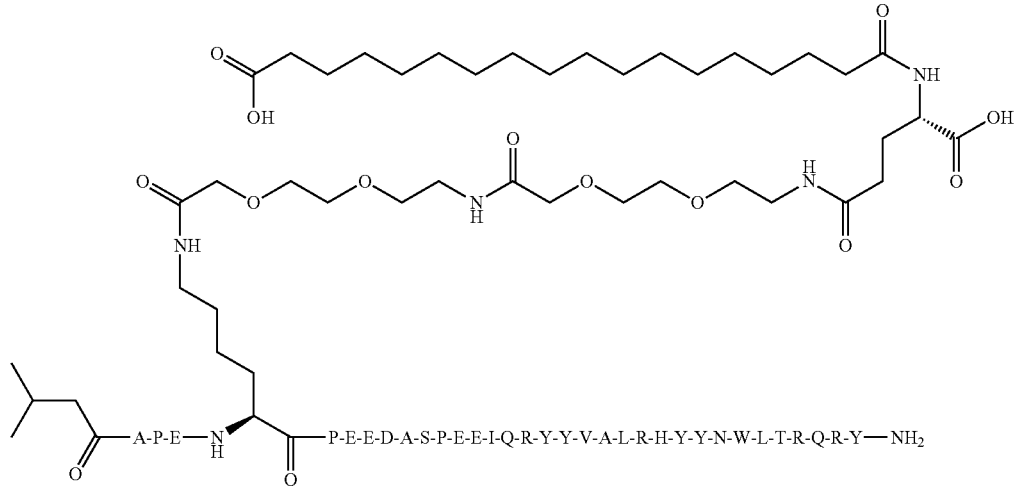

MW (calculated): 4971.6 Da
Synthesis and purification methods: S01; P01
LCMS: A01; Rt: 9.81 min; m/3: – m/4: 1243.0 m/5: -

Compound 231

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,13T,18Q,19K,22Y,28Y,30W,31L]hPYY(4-36) iVal-APEK(C18DA-gGlu-OEG1-OEG2-)PEEDATPEELQKYYVSLRHYYNWLTRQRY-NH2 (sequence and structure below disclosed as SEQ ID NO: 235)

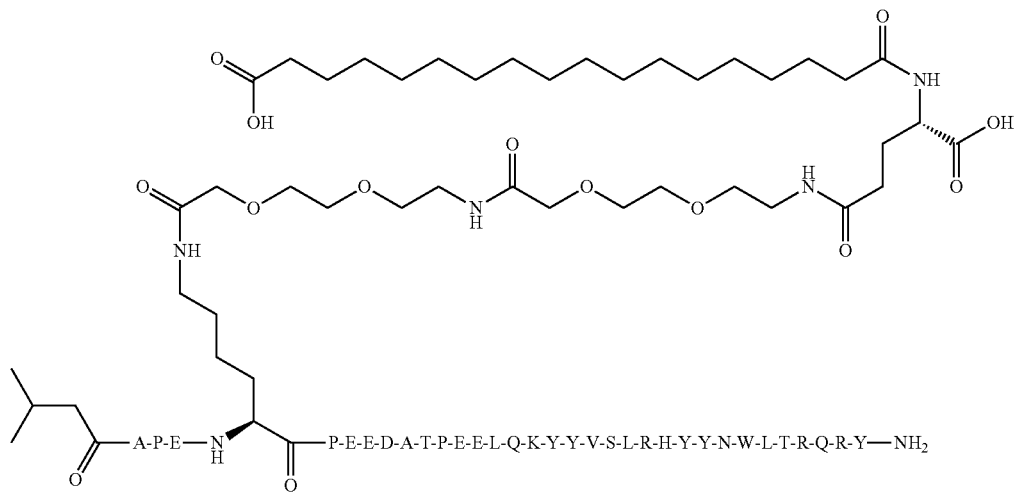

MW (calculated): 4973.6 Da
Synthesis and purification methods: S01; P01
LCMS: A01; Rt: 9.79 min; m/3: – m/4: 1245.0 m/5: -

Compound 232

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9P,18Q,22V,23E,28Y,30W,31L]hPYY(4-36) iVal-APAK(C18DA-gGlu-OEG1-OEG2-)PPEDASPEELQRYYVELRHYYNWLTRQRY-NH2 (SEQ ID NO: 236)

MW (calculated): 4939.6 Da
Synthesis and purification methods: S01; P01
LCMS: A01; Rt: 9.71 min; m/3: – m/4: 1235.0 m/5: -

Compound 233

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11A,18Q,19Q,22V,28Y,30W,31L]hPYY(4-36) iVal-APEK(C18DA-gGlu-OEG1-OEG2-)PEEAASPEELQQYYVSLRHYYNWLTRQRY-NH2 (SEQ ID NO: 237)

MW (calculated): 4915.5 Da
Synthesis and purification methods: S03; P02
LCMS: A02; Rt: 12.58 min; m/3: 1639.6 m/4: 1230.1 m/5: 984.0

Compound 234

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,6A,7K,9E,11E,18Q,22V,28Y,30W,31L]hPYY(4-36) iVal-APAK(C18DA-gGlu-OEG1-OEG2-)PEEEASPEELQRYYVSLRHYYNWLTRQRY-NH2 (sequence and structure below disclosed as SEQ ID NO: 238)

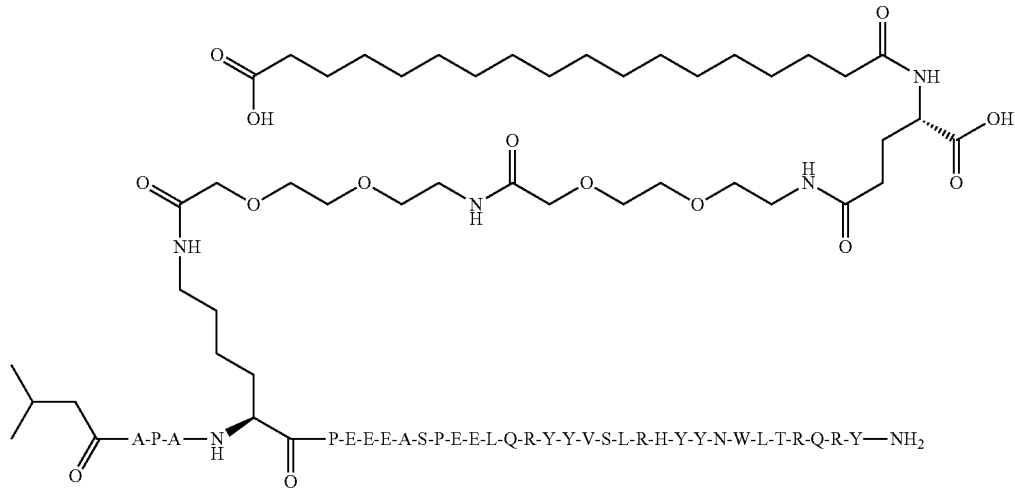

MW (calculated): 4943.6 Da
Synthesis and purification methods: S01; P01
LCMS: A01; Rt: 9.96 min; m/3: 1649.0 m/4: − m/5: -

Compound 235

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,14Hyp,18Q,22V,28Y,30W,31L]hPYY(4-36) iVal-APEK(C18DA-gGlu-OEG1-OEG2-)PEEDASHypEELQRYYVSLRHYYNWLTRQRY-NH2 (SEQ ID NO: 239)

MW (calculated): 5003.6 Da
Synthesis and purification methods: S01; P01
LCMS: A01; Rt: 9.28 min; m/3: − m/4: 1252.0 m/5: -

Compound 236

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,11E,13P,14A,18Q,22V,28Y,30W,31L]hPYY(4-36) iVal-APEK(C18DA-gGlu-OEG1-OEG2-)PEEEAPAEELQRYYVSLRHYYNWLTRQRY-NH2 (SEQ ID NO: 240)

MW (calculated): 4985.6 Da
Synthesis and purification methods: S01; P01
LCMS: A01; Rt: 11.15 min; m/3: − m/4: 1247.0 m/5: -

Compound 237

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,9E,18Q,22V,23E,24V,28Y,30W,31L]hPYY(4-36) iVal-APEK(C18DA-gGlu-OEG1-OEG2-)PEEDASPEELQRYYVEVRHYYNWLTRQRY-NH2 (SEQ ID NO: 241)

MW (calculated): 5015.6 Da
Synthesis and purification methods: S01; P01
LCMS: A01; Rt: 9.60 min; m/3: 1672.0 m/4: − m/5: -

Compound 238

N{alpha-4}-(3-methylbutanoyl)-N{epsilon-7}-[2-(2-{2-[2-(2-{2-[(4S)-4-carboxy-4-(17-carboxyheptade-canamido)butanamido]ethoxy}ethoxy)acetamido]ethoxy}ethoxy) acetamido]-[4A,7K,8T,9E,11E,18Q,22V,28Y,30W,31L]hPYY(4-36) iVal-APEK(C18DA-gGlu-OEG1-OEG2-)TEEEASPEELQRYYVSLRHYYNWLTRQRY-NH2 (SEQ ID NO: 242)

MW (calculated): 5005.6 Da
Synthesis and purification methods: S01; P01
LCMS: A01; Rt: 9.89 min; m/3: 1669.0 m/4: − m/5: −

Compound 239

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,14E,18Q,21E,22V,28Y,30W,31L]hPYY(4-36) iVal-APEK(C18DA-gGlu-OEG1-OEG2-)PEEDASEEELQRYEVSLRHYYNWLTRQRY-NH2 (SEQ ID NO: 243)

MW (calculated): 4985.5 Da
Synthesis and purification methods: S02; P02
LCMS: A02; Rt: 11.55 min; m/3: 1662.9 m/4: 1247.5 m/5: 998.0

Compound 240

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,16A,18Q,22V,28Y,30W,31L]hPYY(4-36) iVal-APEK(C18DA-gGlu-OEG1-OEG2-)PEEDASPEALQRYYVSLRHYYNWLTRQRY-NH2 (SEQ ID NO: 244)

MW (calculated): 4929.6 Da
Synthesis and purification methods: S01; P01
LCMS: A01; Rt: 9.96 min; m/3: 1643.0 m/4: – m/5: -

Compound 241

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,17I,18Q,22V,28Y,30W,31L]hPYY(4-36) iVal-APEK(C18DA-gGlu-OEG1-OEG2-)PEEEASPEEIQRYYVSLRHYYNWLTRQRY-NH2 (SEQ ID NO: 245)

MW (calculated): 5001.6 Da
Synthesis and purification methods: S01; P01
LCMS: A01; Rt: 9.70 min; m/3: – m/4: 1251.0 m/5: -

Compound 242

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,10A,14A,18Q,22V,28Y,30W,31L]hPYY(4-36) iVal-APEK(C18DA-gGlu-OEG1-OEG2-)PEADASAEELQRYYVSLRHYYNWLTRQRY-NH2 (SEQ ID NO: 246)

MW (calculated): 4903.5 Da
Synthesis and purification methods: S01; P01
LCMS: A01; Rt: 10.72 min; m/3: – m/4: 1226.0 m/5: -

Compound 243

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,11E,18Q,19Q,22V,28Y,30W,31L]hPYY(4-36) iVal-APEK(C18DA-gGlu-OEG1-OEG2-)PEEEASPEELQQYYVSLRHYYNWLTRQRY-NH2 (SEQ ID NO: 247)

MW (calculated): 4973.6 Da
Synthesis and purification methods: S03; P02
LCMS: A02; Rt: 11.78 min; m/3: 1659.0 m/4: 1244.6 m/5: 995.5

Compound 244

N{alpha-4}-(3-methylbutanoyl)-N{epsilon-7}-[2-(2-{2-[2-(2-{2-[(4S)-4-carboxy-4-(17-carboxyheptadecanamido)butanamido]ethoxy}ethoxy)acetamido]ethoxy}ethoxy) acetamido]-[4A,7K,9E,13E,15A,18Q,22V,28Y,30W,31L]hPYY(4-36) iVal-APEK(C18DA-gGlu-OEG1-OEG2-)PEEDAEPAELQRYYVSLRHYYNWLTRQRY-NH2 (SEQ ID NO: 248)

MW (calculated): 4971.6 Da
Synthesis and purification methods: S01; P01
LCMS: A01; Rt: 10.08 min; m/3: 1658.0 m/4: – m/5: -

The following compound disclosed as Compound 38 in WO 2016/198682 A1 was synthesized as reference:

Ref. 1
iVal-RPEK(C18DA-gGlu-OEG1-OEG2-)PGE-DASPEELQRYYVSLRHYYNWLTRQRY-NH2 (SEQ ID NO: 249)

Further compounds were synthesized as references:

Ref. 2
iVal-RPEK(C18DA-gGlu-OEG1-OEG2-) PGE-DASPEELQRYYVSLAHYYNWLTRQRY-NH2 (SEQ ID NO: 250)

Ref. 3
iVal-RPEK(C18DA-gGlu-OEG1-OEG2-) PGE-DASPEELQRYYVSLRAYYNWLTRQRY-NH2 (SEQ ID NO: 251)

Ref. 4
iVal-RPEK(C18DA-gGlu-OEG1-OEG2-) PGE-DASPEELQRYYVSLRHYYNWLTAQRY-NH2 (SEQ ID NO: 252)

Ref. 5
iVal-RPEK(C18DA-gGlu-OEG1-OEG2-) PGE-DASPEELQRYYVSLRHYYNWLTRQAY-NH2 (SEQ ID NO: 253)

The structure of Ref. 1 is—except for alanine at position 4—identical to Compound 64. This R4A mutation leads to a compound that shows much higher solubility at pH 6.2 (0.5 mg/ml for Ref. 1 vs. 8.7 mg/ml for compound 64). At the same time high binding 25 affinity and receptor activity are maintained for compound 64 (see Table 2). Other arginine to alanine mutations at different positions (R25A in Ref. 2; R33A in Ref. 4; R35A in Ref. 5) or histidine to alanine mutation at position 26 (H26A in Ref. 3) negatively affect binding affinity and receptor activity or physical stability of the resulting compounds.

TABLE 2

| Comp. | Seq. mod. vs. Ref. 1 | hY2 RLB (nM) (Ex. 1) | hY2 cAMP (nM) (Ex. 2) | Sol pH 6 (mg/ml) [final pH] (Ex. 3) | Sol pH 7 (mg/ml) [final pH] (Ex. 3) | DLS pH 7.2 (Ex. 4) |
|---|---|---|---|---|---|---|
| Ref. 1 | — | 0.47 | 0.075 | 0.5 [6.2] | 8.7 [6.9] | n.d. |
| Comp. 64 | R4A | 0.76 | 0.157 | 8.7 [6.2] | 9.6 [6.8] | OK |
| Ref. 2 | R25A | 8.38 | 1.121 | 9.2 [6.0] | 9.0 [6.7] | n.d. |
| Ref. 3 | H26A | 1.69 | 0.375 | 10.0 [6.0] | 9.7 [6.7] | Not OK |
| Ref. 4 | R33A | 30.94 | 12.615 | 10.0 [6.1] | 10.0 [6.8] | n.d. |
| Ref. 5 | R35A | 316.00 | 293.059 | 9.7 [6.1] | 10.0 [6.8] | n.d. | n.d.: not determined

EXAMPLES

The following examples demonstrate certain specific embodiments of the present invention. The following examples were carried out using standard techniques that are well known and routine to those of skill in the art, except where otherwise described in detail.

Example 1: Radioligand Binding Competition Assays (RLB)

The filtration RLB assay was carried out in 96-well plates in a final volume of 100 μl per well. Freeze-dried test peptides were dissolved in 100% dimethyl sulfoxide (DMSO) to stock solutions of 1 mM and serial dilutions were performed in assay buffer (50 mM HEPES, 5 mM $MgCl_2$, 1 mM $CaCl_2$, pH 7.4) containing 0.2% ovalbumin. 10 μl/well of the test peptide solution was added to the plates to give final concentrations ranging from 1 PM to 3 pM. Subsequently, 10 μl of human $^{125}$I-PYY(1-36) (Perkin Elmer) in assay buffer containing 0.2% ovalbumin was added to wells to give a final concentration of 0.02 nM. Next, 80 μL membranes (HTS066M, ChemiSCREEN™ Human Neuropeptide Y2 Receptor Membrane Preparation, CHEMICON) were added to each well to give a final protein concentration of 0.5 μg/well. The plates were sealed and incubated at room temperature for 2 hours in a plate shaker set at 400 rpm. The incubation was stopped by vacuum filtration onto 0.5% poly-ethylene amine (PEI) presoaked GF/C filters using a 96-well FilterMate™ harvester (Perkin Elmer) followed by four washes with 300 μl/well ice-cold wash buffer (50 mM HEPES, 500 mM NaCl, pH7.4). Filter plates were then dried for 60 min at room temperature and the bottom of the plates was sealed with backing tape UniFilter-96. Finally, 50 μl/well scintillation counter cocktail (Microscint20, Packard) was added and the radioactivity was counted in the Packard TopCount NXT scintillation counter. $IC_{50}$ values (the half maximal inhibitory concentration of the agonist) were calculated by nonlinear regression analysis of sigmoidal dose-response curves. Ki values for binding affinity were acquired by the Cheng-Prusoff equation ($Ki=IC_{50}/(1+[L]/Kd)$, where Kd is the previously measured receptor specific dissociation constant (for NPY2R=0.07 nM) and [L] is $^{125}$I-PYY(1-36) radio-ligand concentration.

The RLB results are summarized in Table 3 below.

| Compound | Ki [nM] |
|---|---|
| 1 | 2.50 |
| 2 | 1.81 |
| 3 | 3.14 |
| 4 | 1.43 |
| 5 | 14.77 |
| 6 | 6.52 |
| 7 | 1.02 |
| 9 | 1.22 |
| 10 | 1.28 |
| 11 | 0.74 |
| 12 | 12.73 |
| 13 | 1.29 |
| 14 | 0.31 |
| 15 | 2.89 |
| 16 | 3.09 |
| 17 | 0.93 |
| 18 | 3.71 |
| 19 | 0.39 |
| 20 | 2.57 |
| 21 | 1.52 |
| 22 | 1.36 |
| 23 | 0.63 |
| 24 | 2.22 |
| 25 | 4.36 |
| 26 | 0.77 |
| 27 | 0.96 |
| 28 | 6.03 |
| 29 | 0.29 |
| 30 | 0.47 |
| 31 | 0.90 |
| 32 | 4.84 |
| 33 | 0.45 |
| 34 | 6.40 |
| 35 | 1.21 |
| 36 | 10.64 |
| 37 | 4.85 |
| 38 | 0.49 |
| 39 | 0.76 |
| 40 | 1.21 |
| 41 | 3.22 |
| 42 | 5.92 |
| 43 | 0.40 |
| 44 | 4.44 |
| 45 | 3.97 |
| 46 | 3.30 |
| 47 | 0.42 |
| 48 | 38.88 |
| 49 | 0.89 |
| 50 | 2.48 |
| 51 | 39.36 |
| 52 | 8.53 |
| 53 | 0.24 |
| 54 | 0.95 |
| 55 | 3.35 |
| 56 | 1.26 |
| 57 | 2.23 |
| 58 | 2.66 |
| 60 | 5.95 |
| 61 | 0.40 |
| 63 | 3.13 |
| 64 | 0.76 |
| 65 | 1.02 |
| 66 | 2.23 |
| 67 | 4.37 |
| 68 | 8.47 |
| 69 | 5.74 |
| 70 | 4.86 |
| 71 | 5.22 |
| 74 | 0.57 |
| 75 | 1.92 |
| 77 | 6.17 |
| 79 | 4.52 |
| 80 | 6.96 |
| 81 | 3.36 |
| 82 | 1.53 |
| 83 | 0.57 |

| Compound | Ki [nM] |
|---|---|
| 84 | 1.19 |
| 85 | 1.56 |
| 86 | 1.19 |
| 87 | 1.97 |
| 88 | 0.83 |
| 89 | 9.61 |
| 90 | 1.60 |
| 91 | 4.66 |
| 92 | 1.57 |
| 93 | 1.01 |
| 94 | 2.07 |
| 95 | 0.66 |
| 96 | 0.76 |
| 97 | 1.12 |
| 98 | 1.30 |
| 99 | 4.88 |
| 100 | 0.44 |
| 101 | 3.29 |
| 102 | 0.87 |
| 103 | 0.95 |
| 104 | 1.37 |
| 105 | 6.94 |
| 106 | 0.66 |
| 107 | 1.10 |
| 108 | 0.99 |
| 109 | 0.94 |
| 110 | 0.77 |
| 111 | 5.43 |
| 112 | 1.36 |
| 115 | 1.94 |
| 116 | 10.03 |
| 117 | 0.34 |
| 118 | 1.37 |
| 119 | 3.32 |
| 120 | 4.81 |
| 121 | 0.61 |
| 122 | 1.84 |
| 124 | 0.50 |
| 126 | 1.18 |
| 127 | 1.01 |
| 128 | 2.10 |
| 129 | 1.14 |
| 130 | 11.10 |
| 131 | 8.54 |
| 132 | 1.18 |
| 133 | 2.31 |
| 134 | 1.17 |
| 135 | 1.31 |
| 136 | 0.89 |
| 137 | 2.35 |
| 138 | 1.42 |
| 139 | 3.83 |
| 140 | 2.66 |
| 141 | 3.12 |
| 142 | 1.17 |
| 143 | 0.83 |
| 144 | 8.92 |
| 145 | 1.55 |
| 146 | 5.05 |
| 147 | 1.19 |
| 148 | 1.75 |
| 149 | 2.75 |
| 150 | 2.02 |
| 151 | 1.43 |
| 152 | 5.18 |
| 153 | 14.43 |
| 155 | 2.05 |
| 157 | 0.71 |
| 158 | 4.43 |
| 159 | 0.83 |
| 160 | 2.00 |
| 163 | 0.96 |
| 164 | 4.33 |
| 165 | 2.49 |
| 166 | 0.66 |
| 168 | 6.36 |
| 169 | 2.34 |
| 170 | 12.29 |
| 171 | 0.34 |
| 173 | 1.71 |
| 174 | 3.89 |
| 175 | 1.24 |
| 176 | 3.05 |
| 177 | 2.55 |
| 178 | 2.05 |
| 179 | 1.00 |
| 180 | 3.85 |
| 181 | 0.67 |
| 182 | 3.45 |
| 183 | 0.70 |
| 184 | 2.06 |
| 185 | 3.58 |
| 186 | 3.36 |
| 187 | 2.76 |
| 188 | 3.09 |
| 189 | 2.08 |
| 190 | 6.05 |
| 191 | 1.70 |
| 192 | 1.65 |
| 193 | 3.81 |
| 194 | 13.36 |
| 195 | 0.75 |
| 196 | 0.98 |
| 197 | 0.87 |
| 198 | 2.40 |
| 199 | 5.69 |
| 200 | 2.34 |
| 202 | 0.60 |
| 203 | 0.75 |
| 204 | 3.35 |
| 205 | 1.90 |
| 207 | 1.07 |
| 208 | 3.80 |
| 209 | 8.07 |
| 210 | 10.48 |
| 211 | 3.43 |
| 212 | 20.28 |
| 213 | 6.54 |
| 214 | 2.56 |
| 215 | 0.48 |
| 216 | 0.93 |
| 217 | 1.01 |
| 218 | 1.49 |
| 219 | 7.60 |
| 220 | 2.99 |
| 221 | 5.49 |
| 223 | 4.77 |
| 224 | 4.64 |
| 225 | 5.89 |
| 226 | 1.21 |
| 227 | 12.28 |
| 229 | 2.84 |
| 230 | 0.71 |
| 231 | 1.96 |
| 232 | 0.81 |
| 234 | 1.95 |
| 235 | 1.04 |
| 236 | 5.58 |
| 237 | 0.76 |
| 238 | 25.11 |
| 240 | 1.36 |
| 241 | 2.95 |
| 242 | 0.81 |
| 243 | 2.07 |
| 244 | 1.84 |

In general, the data from the RLB assay is predictive for the acute food intake inhibition in mice (Experiment 6).

Example 2: HTRF cAMP Gi Assay

The Homogenous Time Resolved fluorescence (HTRF) technology optimized for Gi coupled receptors has thoroughly been described in Cisbio cAMP Gi kit manual. Briefly, the production of intracellular cAMP will generate a competition between unlabeled cAMP and exogenously added d2-cAMP for anti-cAMP antibodies conjugated to cryptate. CHO-K1 cells stably expressing the human NPY1, NPY2, NPY4 and NPY5 receptors were used with the cells brought to life from a frozen stock immediately before assay performance. 2000 cells per well were applied for all four NPY receptor subtype assays. A 384-well format was used applying a total volume of 20 µl using 5 µl cells, 2.5 µl peptide agonist, 2.5 µl forskolin and 5 µl of each of the fluorophores. Cells were incubated with agonist peptides (11 points concentration response curves) and forskolin (~90% activity level, 3-11 µM forskolin) for 40 min at 37° C. using DPBS containing 0.5 mM IBMX as stimulation buffer. After addition of HTRF® detection reagents and incubation with shaking (2400 rpm) for one hour at room temperature signals at 620 and 665 nm (raw counts: ratio of 665/620) were detected. Concentration-response evaluation of compounds was performed with 11 concentrations of agonist peptides (covering 3 decades). EC50 values were calculated by nonlinear regression using sigmoid concentration-response with variable slope.

The in vitro activity results (expressed as $EC_{50}$ values) are summarized in Table 4, below.

TABLE 4

| Compound NO | hY2R (nM) | hY1R (nM) | hY4R (nM) | hY5R (nM) |
|---|---|---|---|---|
| hPYY3-36 | 0.160 | 250 | >5000 | 73.2 |
| 11 | 0.334 | >5000 | >5000 | >5000 |
| 18 | 0.167 | >5000 | >5000 | >5000 |
| 23 | 0.150 | >5000 | >5000 | >5000 |
| 41 | 0.159 | >5000 | >5000 | >5000 |
| 46 | 0.152 | >5000 | >5000 | >5000 |
| 53 | 0.119 | >5000 | >5000 | >5000 |
| 54 | 0.131 | >5000 | >5000 | >5000 |
| 74 | 0.129 | >5000 | >5000 | >5000 |
| 104 | 0.096 | >5000 | >5000 | >5000 |
| 105 | 0.284 | >5000 | >5000 | >5000 |
| 106 | 0.173 | >5000 | >5000 | >5000 |
| 117 | 0.129 | >5000 | >5000 | >5000 |
| 120 | 0.210 | >5000 | >5000 | >5000 |
| 164 | 0.235 | >5000 | >5000 | >5000 |
| 171 | 0.181 | >5000 | >5000 | >5000 |
| 188 | 0.106 | >5000 | >5000 | >5000 |
| 230 | 0.199 | >5000 | >5000 | >5000 |
| 231 | 0.107 | >5000 | >5000 | >5000 |

Example 3: Solubility Determination

Peptides (as TFA salts) were weighed out in a filter unit (Mini-UniPrep Syringeless Filter 0.45 pam, Whatman), and 0.1 M sodium diphosphate buffer at pH 6.4 or 7.0 was added to achieve 10 mg/ml final concentration. The peptide was dissolved by shaking the filter unit horizontally at 600 rpm for 2 hours at room temperature. The sample was filtered, to remove any insoluble particles and diluted to 1 mg/ml in 50% acetonitrile. The control was prepared by weighing out the corresponding peptide and dissolving it in 50% acetonitrile to final concentration of 1 mg/ml. Both the control and sample were analysed with reversed phase chromatography. The area under the peak of the sample was compared to the control and the solubility was calculated based on that ratio.

The pH was measured and recorded for each sample. Typically, buffer pH dropped by 0.2 to 0.3 pH units due to the TFA content of the peptide.

UPLC Method:
System: UltiMate 3000 UPLC, ThermoFisher
Mobile phase A: 5% acetonitrile, 95% water, 0.03% trifluoracetic acid.
Mobile phase B: 95% acetonitrile, 5% water, 0.03% trifluoracetic acid.
Flow: 1 ml/min
Gradient: 0-100% mobile phase B (2 mins.)
Column: Kinetix, 5 µm C8, 100 Å, 50×2.1 mm
Column temperature: 50° C.

The results from the solubility determination are summarized in Table 5, below.

TABLE 5

| Compound | Sol6 (mg/ml) | Sol6 pH | Sol7 (mg/ml) | Sol7 pH |
|---|---|---|---|---|
| 3 | 10.0 | 6.1 | 9.7 | 6.8 |
| 5 | 8.7 | 6.1 | 9.7 | 6.8 |
| 8 | 10.0 | 6.0 | 9.9 | 6.7 |
| 10 | 9.9 | 6.1 | 10.0 | 6.8 |
| 11 | 10.0 | 6.1 | 10.0 | 6.8 |
| 12 | 10.0 | 6.1 | 9.8 | 6.7 |
| 13 | 9.6 | 6.1 | 9.1 | 6.7 |
| 14 | 9.8 | 6.1 | 9.9 | 6.8 |
| 16 | 10.0 | 6.1 | 9.9 | 6.7 |
| 17 | 10.0 | 6.1 | 9.0 | 6.9 |
| 19 | 9.9 | 6.1 | 9.9 | 6.8 |
| 20 | 10.0 | 6.0 | 9.7 | 6.7 |
| 23 | 7.6 | 6.1 | 10.0 | 6.8 |
| 24 | 9.0 | 6.1 | 9.7 | 6.8 |
| 26 | 9.7 | 6.2 | 10.0 | 6.9 |
| 27 | 9.8 | 6.1 | 10.0 | 6.8 |
| 29 | 10.0 | 6.2 | 9.1 | 6.8 |
| 30 | 9.5 | 6.1 | 9.8 | 6.8 |
| 31 | 10.0 | 6.1 | 10.0 | 6.7 |
| 33 | 10.0 | 6.1 | 9.6 | 6.7 |
| 35 | 8.7 | 6.1 | 9.3 | 6.8 |
| 36 | 10.0 | 6.1 | 10.0 | 6.8 |
| 38 | 8.9 | 6.2 | 9.2 | 6.8 |
| 39 | 9.6 | 6.2 | 9.2 | 6.9 |
| 40 | 10.0 | 6.1 | 10.0 | 6.7 |
| 41 | 9.6 | 6.1 | 8.9 | 6.7 |
| 43 | 0.2 | 6.2 | 9.9 | 6.9 |
| 45 | 9.8 | 6.1 | 9.6 | 6.7 |
| 47 | 0.7 | 6.2 | 9.3 | 6.8 |
| 48 | 9.7 | 6.1 | 9.6 | 6.7 |
| 49 | 10.0 | 6.1 | 10.0 | 6.7 |
| 52 | 7.7 | 6.1 | 9.9 | 6.8 |
| 53 | 9.7 | 6.2 | 9.5 | 6.8 |
| 54 | 9.4 | 6.1 | 10.7 | 6.8 |
| 56 | 10.0 | 6.1 | 10.0 | 6.8 |
| 57 | 9.0 | 6.1 | 8.0 | 6.7 |
| 59 | 10.0 | 6.1 | 10.0 | 6.8 |
| 60 | 9.2 | 6.1 | 10.0 | 6.7 |
| 61 | 9.2 | 6.2 | 9.7 | 6.8 |
| 64 | 8.7 | 6.2 | 9.6 | 6.8 |
| 65 | 8.2 | 6.0 | 9.7 | 6.8 |
| 67 | 9.2 | 6.0 | 9.1 | 6.8 |
| 68 | 10.0 | 6.1 | 10.0 | 6.7 |
| 70 | 9.7 | 6.1 | 9.1 | 6.7 |
| 72 | 9.2 | 6.1 | 9.5 | 6.7 |
| 74 | 8.6 | 6.1 | 9.4 | 6.8 |
| 78 | 10.0 | 6.1 | 10.0 | 6.7 |
| 79 | 10.0 | 6.1 | 10.0 | 6.7 |
| 80 | 10.0 | 6.1 | 10.0 | 6.7 |
| 81 | 10.0 | 6.1 | 9.1 | 6.9 |
| 82 | 8.9 | 6.2 | 9.9 | 6.8 |
| 83 | 0.0 | 6.2 | 3.2 | 6.8 |
| 87 | 7.9 | 6.2 | 10.0 | 6.8 |
| 88 | 10.0 | 6.1 | 9.8 | 6.8 |
| 89 | 9.9 | 6.1 | 10.0 | 6.7 |
| 91 | 9.9 | 6.1 | 9.6 | 6.7 |
| 93 | 9.9 | 6.1 | 8.5 | 6.7 |
| 95 | 9.9 | 6.2 | 9.6 | 6.8 |
| 96 | 10.0 | 6.1 | 10.0 | 6.9 |
| 97 | 9.7 | 6.0 | 9.1 | 6.8 |
| 100 | 0.8 | 6.2 | 9.0 | 6.8 |

TABLE 5-continued

| Compound | Sol6 (mg/ml) | Sol6 pH | Sol7 (mg/ml) | Sol7 pH |
|---|---|---|---|---|
| 101 | 10.0 | 6.0 | 9.3 | 6.7 |
| 102 | 9.3 | 6.0 | 8.6 | 6.8 |
| 103 | 10.0 | 6.1 | 10.0 | 6.8 |
| 106 | 9.5 | 6.2 | 9.9 | 6.8 |
| 109 | 9.5 | 6.2 | 9.2 | 6.8 |
| 110 | 9.4 | 6.0 | 9.5 | 6.7 |
| 112 | 9.9 | 6.1 | 9.8 | 6.7 |
| 113 | 9.8 | 6.1 | 10.0 | 6.7 |
| 115 | 9.7 | 6.2 | 9.5 | 6.8 |
| 117 | 9.4 | 6.1 | 8.8 | 6.8 |
| 118 | 8.8 | 6.2 | 8.4 | 6.8 |
| 119 | 10.0 | 6.0 | 10.0 | 6.7 |
| 121 | 0.3 | 6.2 | 9.3 | 6.8 |
| 122 | 7.3 | 6.1 | 9.7 | 6.7 |
| 124 | 9.8 | 6.1 | 10.0 | 6.7 |
| 126 | 9.5 | 6.2 | 9.0 | 6.8 |
| 127 | 8.5 | 6.1 | 7.9 | 6.8 |
| 128 | 10.0 | 6.1 | 9.6 | 6.8 |
| 129 | 9.5 | 6.1 | 10.0 | 6.8 |
| 131 | 8.6 | 6.1 | 9.1 | 6.8 |
| 132 | 9.2 | 6.2 | 9.5 | 6.8 |
| 133 | 8.7 | 6.0 | 10.0 | 6.7 |
| 134 | 10.0 | 6.1 | 9.9 | 6.8 |
| 135 | 9.6 | 6.1 | 7.9 | 6.8 |
| 136 | 9.2 | 6.2 | 10.0 | 6.8 |
| 138 | 9.7 | 6.1 | 10.0 | 6.7 |
| 139 | 10.0 | 6.0 | 8.9 | 6.7 |
| 142 | 9.1 | 6.1 | 9.7 | 6.8 |
| 143 | 10.0 | 6.2 | 9.6 | 6.8 |
| 144 | 9.7 | 6.1 | 10.0 | 6.8 |
| 145 | 8.8 | 6.1 | 9.5 | 6.8 |
| 148 | 9.5 | 6.1 | 10.0 | 6.7 |
| 149 | 9.6 | 6.1 | 9.4 | 6.8 |
| 150 | 9.8 | 6.0 | 10.0 | 6.7 |
| 151 | 9.5 | 6.1 | 9.5 | 6.8 |
| 152 | 10.0 | 6.1 | 10.0 | 6.8 |
| 153 | 10.0 | 6.0 | 10.0 | 6.7 |
| 155 | 9.8 | 6.0 | 8.9 | 6.8 |
| 156 | 10.0 | 6.1 | 9.6 | 6.7 |
| 157 | 9.1 | 6.1 | 9.4 | 6.8 |
| 159 | 10.0 | 6.1 | 9.7 | 6.7 |
| 160 | 10.0 | 6.1 | 10.0 | 6.7 |
| 161 | 10.0 | 6.1 | 8.8 | 6.7 |
| 163 | 9.2 | 6.1 | 10.0 | 6.8 |
| 165 | 10.0 | 6.1 | 9.6 | 6.8 |
| 166 | 10.0 | 6.2 | 10.0 | 6.8 |
| 169 | 9.8 | 6.1 | 10.0 | 6.7 |
| 171 | 9.7 | 6.1 | 9.5 | 6.8 |
| 172 | 10.0 | 6.1 | 10.0 | 6.7 |
| 173 | 9.9 | 6.1 | 10.0 | 6.7 |
| 174 | 8.9 | 6.1 | 8.8 | 6.8 |
| 175 | 9.0 | 6.1 | 10.0 | 6.8 |
| 177 | 7.7 | 6.1 | 7.3 | 6.8 |
| 178 | 9.8 | 6.1 | 9.7 | 6.7 |
| 179 | 0.0 | 6.3 | 0.4 | 6.8 |
| 181 | 10.0 | 6.2 | 10.0 | 6.7 |
| 182 | 9.7 | 6.1 | 9.3 | 6.7 |
| 183 | 9.3 | 6.2 | 8.0 | 6.9 |
| 184 | 9.7 | 6.1 | 10.0 | 6.7 |
| 185 | 10.0 | 6.1 | 9.5 | 6.8 |
| 186 | 8.8 | 6.1 | 9.6 | 6.8 |
| 189 | 8.3 | 6.1 | 9.8 | 6.8 |
| 190 | 10.0 | 6.1 | 10.0 | 6.7 |
| 192 | 9.1 | 6.2 | 8.9 | 6.8 |
| 193 | 9.8 | 6.1 | 9.9 | 6.8 |
| 195 | 8.8 | 6.1 | 9.7 | 6.7 |
| 196 | 9.7 | 6.2 | 9.8 | 6.9 |
| 197 | 10.0 | 6.1 | 10.0 | 6.8 |
| 198 | 9.8 | 6.1 | 9.7 | 6.8 |
| 199 | 9.2 | 6.1 | 9.1 | 6.8 |
| 202 | 9.7 | 6.1 | 9.8 | 6.7 |
| 203 | 8.8 | 6.2 | 9.6 | 6.9 |
| 204 | 8.5 | 6.1 | 9.5 | 6.8 |
| 205 | 10.0 | 6.1 | 9.9 | 6.7 |
| 206 | 10.0 | 6.0 | 10.0 | 6.7 |
| 207 | 9.1 | 6.2 | 9.7 | 6.9 |
| 208 | 5.1 | 6.1 | 9.6 | 6.8 |
| 209 | 8.9 | 6.0 | 9.5 | 6.7 |
| 211 | 9.0 | 6.1 | 6.2 | 6.8 |
| 213 | 9.5 | 6.1 | 10.0 | 6.8 |
| 214 | 10.0 | 6.1 | 10.0 | 6.8 |
| 215 | 9.7 | 6.1 | 10.0 | 6.8 |
| 216 | 9.9 | 6.1 | 9.8 | 6.7 |
| 217 | 10.0 | 6.2 | 10.0 | 6.7 |
| 218 | 9.3 | 6.1 | 9.4 | 6.8 |
| 220 | 9.8 | 6.2 | 9.1 | 6.8 |
| 221 | 9.8 | 6.1 | 10.0 | 6.7 |
| 222 | 9.0 | 6.1 | 8.7 | 6.7 |
| 227 | 9.5 | 6.1 | 9.5 | 6.7 |
| 229 | 8.8 | 6.0 | 8.2 | 6.9 |
| 230 | 8.6 | 6.1 | 8.2 | 6.7 |
| 231 | 8.0 | 6.1 | 9.9 | 6.7 |
| 232 | 10.0 | 6.1 | 9.7 | 6.8 |
| 233 | 10.0 | 6.1 | — | — |
| 234 | 9.3 | 6.1 | 7.8 | 6.7 |
| 236 | 10.0 | 6.1 | 9.7 | 6.7 |
| 237 | 10.0 | 6.1 | 9.8 | 6.7 |
| 239 | 9.9 | 6.0 | 9.6 | 6.7 |
| 240 | 10.0 | 6.2 | 10.0 | 6.9 |
| 241 | 9.8 | 6.1 | 9.5 | 6.7 |
| 242 | 8.3 | 6.1 | 8.5 | 6.8 |
| 244 | 9.3 | 6.1 | 8.8 | 6.8 |
| Ref 1 | 0.5 | 6.2 | 8.7 | 6.9 |

Example 4: DLS Studies

Aggregation combined with particle growth in peptide solutions was detected by dynamic light scattering (DLS). Test peptides (5 mg/ml) were dissolved in 50 mM phosphate buffer with EDTA (0.05 mg/ml) which is adjusted to a final pH of 7.2. Solutions were filtered through a 0.2 µm filter and shaken with a lab shaker at approx. 150 rpm at room temperature for 5 to 7 days. Samples were analyzed with a particle size analyzer (DLS, Horiba Nano Particle Analyzer SZ-100) at day 0 and at the end of the study. Formation of aggregates was detected by an increase in particle size over time and rated as OK, indicating no increase in particle size, and NOK, indicating an increase in particle size.

The results from the DLS studies are summarized in Table 6.

TABLE 6

| Example | DLS |
|---|---|
| 23 | OK |
| 53 | OK |
| 64 | OK |
| 106 | OK |
| 117 | OK |
| 171 | OK |
| 230 | OK |

Example 5: Mouse PK

Pharmacokinetic parameters of the test compounds were determined after intravenous administration to NMRI mice.

Male NMRI mice were obtained either from Charles River (Germany) or from Janvier (France) weighing approximately 30 to 40 g. Mice were housed in standard cages with light cycle of 12-hour dark and 12-hour light. Standardized food and water were offered ad libitum to the animals during the whole experimental period.

The respective peptide was dissolved in 50 mM phosphate buffer (pH 7.0) containing 5% mannitol. Intravenous doses of 30 nmol/kg were given via a tail vein.

Serial blood samples were collected from the vena sephena into tubes containing EDTA as anticoagulant at different time points up to 48h post dosing. After centrifugation for approximately 5 minutes, plasma samples were transferred to 96-well PCR plates, immediately frozen and kept at approximately −20° C. until analyzed for plasma concentration by liquid chromatography mass spectrometry (LC-MS/MS). Individual plasma concentration-time profiles were analyzed by a non-compartmental approach, and the resulting pharmacokinetic parameters were determined.

| Compound | Mouse MRT (h) | Terminal half-life (h) |
| --- | --- | --- |
| Ref. 1 | 11 | 8.2 |

Mouse MRT of the PYY analogues according to the invention that have been measured were comparable to Ref. 1 and show very long half-lives as compared to the half-life of hPYY(3-36).

Example 6: Effect on Acute Food Intake in Normal NMRI Mice

Male NMRI mice were obtained from Charles River (Charles River, Research Models & Services Germany GmbH) or from JanVier (JanVier Labs, France) at 5 weeks of age. The animals were group housed 4 mice pr. cage under a 12/12 h dark-light cycle, light off at 3 PM. Room temperature was controlled to 21° C.±1° C., with 60%±20% humidity. Animals had ad libitum access to regular rodent chow (KLIBA Nafag 3430 or Altromin 1324, Brogaarden, Denmark) and tap water.

Animals were transferred 5-7 days before the start of the study to a real-time food intake monitoring system, HM-2 system (MBRose, Denmark), to allow acclimatization to experimental conditions. As the animals were uniquely identified with microchips, each individual animal was identified by its microchip upon entry and exit from the food channel. Randomization of the mice for each study group (n=7-8) was based on body weight measured the day before the start of the study. A vehicle-treated (50 mM phosphate buffer pH7 with 5% Mannitol) group was included in each experiment. Six hours before the start of the night phase animals were fasted. One hour before the dark phase animals were dosed once subcutaneously (10 nmol/kg) with test peptide. Food intake was reported hourly for a period of 24h. The food intake of the treated groups was normalized (in %) to the average food intake of the group receiving vehicle (Table 7). Statistical significance was evaluated using One-way analysis of variance with Turkey's multiple comparison test. P<0.05 was considered statistically significant.

TABLE 7

| Compound | Acute Food Intake 24 h [% vehicle] |
| --- | --- |
| 1 | 77 |
| 3 | 62 |
| 7 | 47 |
| 9 | 44 |
| 11 | 42 |
| 14 | 46 |
| 16 | 67 |
| 18 | 58 |
| 21 | 89 |
| 23 | 48 |
| 29 | 63 |
| 30 | 45 |
| 31 | 53 |
| 33 | 54 |
| 41 | 44 |
| 46 | 39 |
| 49 | 60 |
| 53 | 29 |
| 54 | 42 |
| 56 | 53 |
| 58 | 44 |
| 74 | 41 |
| 79 | 75 |
| 90 | 70 |
| 97 | 52 |
| 101 | 63 |
| 103 | 67 |
| 104 | 61 |
| 105 | 72 |
| 106 | 39 |
| 108 | 47 |
| 110 | 67 |
| 115 | 49 |
| 117 | 45 |
| 120 | 74 |
| 124 | 58 |
| 132 | 64 |
| 133 | 57 |
| 135 | 44 |
| 139 | 74 |
| 148 | 60 |
| 150 | 67 |
| 151 | 45 |
| 154 | 73 |
| 159 | 53 |
| 163 | 50 |
| 164 | 64 |
| 167 | 73 |
| 171 | 44 |
| 173 | 49 |
| 174 | 41 |
| 176 | 52 |
| 180 | 74 |
| 185 | 39 |
| 188 | 55 |
| 193 | 57 |
| 195 | 50 |
| 202 | 48 |
| 205 | 65 |
| 208 | 61 |
| 209 | 50 |
| 211 | 62 |
| 221 | 61 |
| 230 | 44 |
| 231 | 39 |
| 234 | 42 |
| 241 | 45 |
| 244 | 49 |
| Ref. 1 | 41 |

Example 7: Activity after Incubation in Solutions at Different pH Values

Peptides (as TFA salts) were weighed out in a filter unit (Mini-UniPrep Syringeless Filter 0.45 μm, Whatman), and 0.1 M sodium diphosphate buffer at pH 6.4 or 7.4, respectively, or 0.2 M TRIS buffer at pH 8.3 was added to achieve 10 mg/ml final concentration. The peptide was (partially)

dissolved by shaking the filter unit horizontally at approx. 400 rpm for 2 hours at room temperature. The sample was filtered to remove any insoluble particles. The filtrate was subsequently subjected to the binding assay as described in Example 1. The apparent binding affinity (Ki) reported in Table 8 is calculated based on an assumed concentration of 10 mg/ml.

Compounds of the invention are active in the binding assay after incubation in solutions at different pH values, including pH 6. This demonstrates the fundamental feasibility of a liquid formulation of the compounds according to the invention at ~pH 6 (in the pH range from ~6 to ~8).

Contrary hereto, after incubation at ~pH 6, solutions of Ref. 1 (after filtration) show a weak response in the binding assay (apparent significant (>35×) affinity loss due to low solubility of Ref. 1 in buffered media at pH 6). Therefore, the low intrinsic solubility of Ref. 1 at ~pH 6 limits the formulation space in the physiological pH range of 6-8 of a liquid formulation of Ref. 1.

TABLE 8

| Cpd. | hY2R RLB Ki (nM) DMSO | RLB 6 (pH6.1-6.2) (nM) | RLB 7 (pH7.1-7.2) (nM) | RLB 8 (pH8.1-8.2) (nM) | RLB ratio (RLB6/RLB7) | RLB ratio (RLB8/RLB7) |
|---|---|---|---|---|---|---|
| Ref. 1 | 3.0 | >216 | 2.9 | 2.4 | >74 | 0.8 |
| 23 | 4.9 | 6.3 | 6.3 | 6.3 | 1.0 | 1.0 |
| 29 | 4.6 | 3.8 | 4.4 | 2.3 | 0.9 | 0.5 |
| 53 | 2.0 | 3.4 | 3.1 | 2.5 | 1.1 | 0.8 |
| 84 | 3.5 | 6.6 | 2.9 | 4.1 | 2.3 | 1.4 |
| 106 | 6.0 | 7.7 | 9.3 | 7.5 | 0.8 | 0.8 |
| 117 | 4.1 | 6.7 | 2.1 | 8.8 | 3.2 | 4.2 |
| 171 | 6.7 | 3.0 | 6.1 | 5.6 | 0.5 | 0.9 |
| 203 | 3.0 | 4.6 | 11.1 | 8.8 | 0.4 | 0.8 |

```
                         SEQUENCE LISTING

Sequence total quantity: 259
SEQ ID NO: 1           moltype = AA  length = 36
FEATURE                Location/Qualifiers
REGION                 1..36
                       note = hNPY
SITE                   36
                       note = C-term amidation
source                 1..36
                       mol_type = protein
                       organism = Homo sapiens
SEQUENCE: 1
YPSKPDNPGE DAPAEDMARY YSALRHYINL ITRQRY                                 36

SEQ ID NO: 2           moltype = AA  length = 36
FEATURE                Location/Qualifiers
REGION                 1..36
                       note = hPYY(1-36)
SITE                   36
                       note = C-term amidation
source                 1..36
                       mol_type = protein
                       organism = Homo sapiens
SEQUENCE: 2
YPIKPEAPGE DASPEELNRY YASLRHYLNL VTRQRY                                 36

SEQ ID NO: 3           moltype = AA  length = 36
FEATURE                Location/Qualifiers
REGION                 1..36
                       note = hPP
SITE                   36
                       note = C-term amidation
source                 1..36
                       mol_type = protein
                       organism = Homo sapiens
SEQUENCE: 3
APLEPVYPGD NATPEQMAQY AADLRRYINM LTRPRY                                 36

SEQ ID NO: 4           moltype = AA  length = 34
FEATURE                Location/Qualifiers
REGION                 1..34
                       note = hPYY(3-36)
source                 1..34
                       mol_type = protein
                       organism = Homo sapiens
SEQUENCE: 4
IKPEAPGEDA SPEELNRYYA SLRHYLNLVT RQRY                                   34

SEQ ID NO: 5           moltype = AA  length = 33
FEATURE                Location/Qualifiers
REGION                 1..33
                       note = Synthetic PPY analogue polypeptide
SITE                   1
                       note = N-term 3-methylbutanoyl
SITE                   4
```

```
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 5
APEKPEEDAQ PEELQEYYVS LRHYYNWLTR QRY                                      33

SEQ ID NO: 6            moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    2
                        note = (4R)-4-hydroxy-L-proline
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 6
AXEKPEEDAS PEELQRYYVS LRHYYNWLTR QRY                                      33

SEQ ID NO: 7            moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 7
APEKPEEEAS PAELQRYYVS LRHYYNWLTR QRY                                      33

SEQ ID NO: 8            moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 8
```

```
APEKPEEDAS PEELQRYYVS LRHYYNWLQR QRY                                          33

SEQ ID NO: 9            moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 9
APEKPEEEVS PEELQRYYVS LRHYYNWLTR QRY                                          33

SEQ ID NO: 10           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 10
APEKPEEEAS PEELQRYYVS ARHYYNWLTR QRY                                          33

SEQ ID NO: 11           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 11
APEKPEEDAS PEELQAYYVS LRHYYNWLTR QRY                                          33

SEQ ID NO: 12           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-
```

```
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 12
APEKPEEDAS EEELQQYYVS LRHYYNWLTR QRY                                  33

SEQ ID NO: 13            moltype = AA  length = 33
FEATURE                  Location/Qualifiers
REGION                   1..33
                         note = Synthetic PPY analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 13
APEKPEEDAS PEEIQRYYVE LRHYYNWLTR QRY                                  33

SEQ ID NO: 14            moltype = AA  length = 33
FEATURE                  Location/Qualifiers
REGION                   1..33
                         note = Synthetic PPY analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 14
APEKPEADAS PEETQRYYVS LRHYYNWLTR QRY                                  33

SEQ ID NO: 15            moltype = AA  length = 33
FEATURE                  Location/Qualifiers
REGION                   1..33
                         note = Synthetic PPY analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 15
APEKPEEDAS PEEIQQYYVS LRHYYNWLTR QRY                                  33

SEQ ID NO: 16            moltype = AA  length = 33
FEATURE                  Location/Qualifiers
REGION                   1..33
                         note = Synthetic PPY analogue polypeptide
```

```
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 16
APEKPEEDAP GEELQRYYVS LRHYYNWLTR QRY                                              33

SEQ ID NO: 17           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 17
APEKPEEDAA PEELQQYYVS LRHYYNWLTR QRY                                              33

SEQ ID NO: 18           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 18
APEKPEADAT PEELQRYYVS LRHYYNWLTR QRY                                              33

SEQ ID NO: 19           moltype = AA  length = 33
FEATURE                 Location/Qualifiers
REGION                  1..33
                        note = Synthetic PPY analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 19
APEKPEEDAS PEEIQRYEVS LRHYYNWLTR QRY                                33

SEQ ID NO: 20            moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 20
APEKPEEDAS PEETQRYYVT LRHYYNWLTR QRY                                33

SEQ ID NO: 21            moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 21
APEKPEEDAS PAELQRYYVS LRHYYNWLTR QRY                                33

SEQ ID NO: 22            moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 22
APEKPEEDAE PEELQQYYVS LRHYYNWLTR QRY                                33

SEQ ID NO: 23            moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
```

```
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 23
APEKPEADAS PEELQQYYVS LRHYYNWLTR QRY                                      33

SEQ ID NO: 24           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 24
APEKPEEDAA PEELQRYYVE LRHYYNWLTR QRY                                      33

SEQ ID NO: 25           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 25
APEKPEEDAS PEELQKYYVS LRHYYNWLTR QRY                                      33

SEQ ID NO: 26           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
                                       -continued

SEQUENCE: 26
APEKPEEDAS PEELQRYYTS LRHYYNWLTR QRY                            33

SEQ ID NO: 27           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 27
APAKPEEDAS PEEIQRYYVS LRHYYNWLTR QRY                            33

SEQ ID NO: 28           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 28
APEKPEEDAS PEELQRYYVS LRKYYNWLTR QRY                            33

SEQ ID NO: 29           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 29
APEKPEEEAS AEELQRYYVS LRHYYNWLTR QRY                            33

SEQ ID NO: 30           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 30
APEKPPEDAT PEELQRYYVS LRHYYNWLTR QRY                                     33

SEQ ID NO: 31           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 31
APEKPPEDAE PEELQRYYVS LRHYYNWLTR QRY                                     33

SEQ ID NO: 32           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 32
APEKPEEDTS PEELQRYYVE LRHYYNWLTR QRY                                     33

SEQ ID NO: 33           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 33
APEKPEAPAS PEELQRYYVE LRHYYNWLTR QRY                              33

SEQ ID NO: 34           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 34
APEKPEADAS EEELQRYYVS LRHYYNWLTR QRY                              33

SEQ ID NO: 35           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 35
APEKPEEDAS PEETQRYYVA LRHYYNWLTR QRY                              33

SEQ ID NO: 36           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 36
APEKPEEDTS PEELQRYEVS LRHYYNWLTR QRY                              33

SEQ ID NO: 37           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                            note = The epsilon amino group of Lys has the following
                              substituent: [2-
                              (2-
                              )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 37
APEKPEEPAS PEELQRYYVE LRHYYNWLTR QRY                                   33

SEQ ID NO: 38               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                              )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 38
APEKPEEDAS PEELQRYYVS TRHYYNWLTR QRY                                   33

SEQ ID NO: 39               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                              )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 39
APEKPEEDAA PEETQRYYVS LRHYYNWLTR QRY                                   33

SEQ ID NO: 40               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                              )butan amido]ethoxy
ethoxy)acetamido]ethoxy
ethoxy)acetyl
SITE                        33
                            note = C-term amidation
source                      1..33
                            mol_type = protein
                            organism = synthetic construct
```

```
SEQUENCE: 40
APEKAEEDAE PEELQRYYVS LRHYYNWLTR QRY                                              33

SEQ ID NO: 41           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 41
APEKPEEDAS PEETQRYEVS LRHYYNWLTR QRY                                              33

SEQ ID NO: 42           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 42
APEKPPEDAS PEELQRYYVA LRHYYNWLTR QRY                                              33

SEQ ID NO: 43           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 43
APEKPPADAE PEELQRYYVS LRHYYNWLTR QRY                                              33

SEQ ID NO: 44           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 44
APEKPEEDAT PEETQRYYVS LRHYYNWLTR QRY                                            33

SEQ ID NO: 45           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 45
APEKPEEEAT PEELQRYYVS LRHYYNWLTR QRY                                            33

SEQ ID NO: 46           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 46
APEKPEEAAS PEELQRYYVS TRHYYNWLTR QRY                                            33

SEQ ID NO: 47           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 47
APEKPEAPAS PEELQRYYVS LRHYYNWLTR QRY                              33

SEQ ID NO: 48            moltype = AA   length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 48
APEKPEEEAS PEELQRYYVS LRHYYNWITR QRY                              33

SEQ ID NO: 49            moltype = AA   length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 49
APEKPEEEAS PESLQRYYVS LRHYYNWLTR QRY                              33

SEQ ID NO: 50            moltype = AA   length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 50
APEKPEEEAS PEELQRYYVS LRHYYNWLTR QRY                              33

SEQ ID NO: 51            moltype = AA   length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
```

-continued

```
                                note = The epsilon amino group of Lys has the following
                                  substituent: [2-
                                  (2-

)butan amido]ethoxy
ethoxy)acetamido]ethoxy
ethoxy)acetyl
SITE                            33
                                note = C-term amidation
source                          1..33
                                mol_type = protein
                                organism = synthetic construct
SEQUENCE: 51
APEKPPADAS PEELQRYYVS LRHYYNWLTR QRY                                         33

SEQ ID NO: 52              moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
SEQUENCE: 52
APEKPEEDTE PEELQRYYVS LRHYYNWLTR QRY                                         33

SEQ ID NO: 53              moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
SEQUENCE: 53
APEKPEEDAS PEELQQYYVE LRHYYNWLTR QRY                                         33

SEQ ID NO: 54              moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
```

```
SEQUENCE: 54
APEKPEEDAS AEELQRYYVS LRHYYNWITR QRY                                               33

SEQ ID NO: 55           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 55
APEKAEEEAS PEELQRYYVS LRHYYNWLTR QRY                                               33

SEQ ID NO: 56           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 56
APEKAEEDAS EEELQRYYVS LRHYYNWLTR QRY                                               33

SEQ ID NO: 57           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 57
APEKPEADAS PEEIQRYYVS LRHYYNWLTR QRY                                               33

SEQ ID NO: 58           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 58
APEKPEEDAS PEELQRYYVS LRHYYNWLTR QRY                                              33

SEQ ID NO: 59           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 59
APEKPEEDAS PEEAQRYYVS LRHYYNWLTR QRY                                              33

SEQ ID NO: 60           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 60
APEKPEADAE PEELQRYYVS LRHYYNWLTR QRY                                              33

SEQ ID NO: 61           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 61
APEKPEEDAS AEEIQRYYVS LRHYYNWLTR QRY                                          33

SEQ ID NO: 62           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 62
APEKPEEDAS PEELQQYYVS LRHYYNWLTR QRY                                          33

SEQ ID NO: 63           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 63
APEKPEEDAS PEETEQYYVS LRHYYNWLTR QRY                                          33

SEQ ID NO: 64           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 64
APEKPEEAAS PEELEQYYVS LRHYYNWLTR QRY                                          33

SEQ ID NO: 65           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 65
APEKPPEDAS PEEIQRYYVS LRHYYNWLTR QRY                                        33

SEQ ID NO: 66               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 66
APEKPGEDAS PEELERYYVS LRHYYNWLTR QRY                                        33

SEQ ID NO: 67               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 67
APEKPEEDAS PEELQRYYVS LRAYYNWLTR QRY                                        33

SEQ ID NO: 68               moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
```

```
SEQUENCE: 68
APEKPGEDAS PEELQRYYVS LRHYYNWLTR QRY                               33

SEQ ID NO: 69           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 69
APEKPEEDAS PEELQRYYVE IRHYYNWLTR QRY                               33

SEQ ID NO: 70           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 70
APEKPEEDAS AEETQRYYVS LRHYYNWLTR QRY                               33

SEQ ID NO: 71           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 71
APEKPEEDSA PEELQRYYVS LRHYYNWLTR QRY                               33

SEQ ID NO: 72           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 72
APEKPEEEAS PEELQAYYVS LRHYYNWLTR QRY                                          33

SEQ ID NO: 73           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 73
APEKPEEDSS AEELQRYYVS LRHYYNWLTR QRY                                          33

SEQ ID NO: 74           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 74
APEKPEEAAS PEELQRYEVS LRHYYNWLTR QRY                                          33

SEQ ID NO: 75           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 75
APEKPEEEAS PSELQRYYVS LRHYYNWLTR QRY                                              33

SEQ ID NO: 76           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 76
APEKPEEEGS PEELQRYYVS LRHYYNWLTR QRY                                              33

SEQ ID NO: 77           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 77
APEKPEEEAS PEELQRYYVS LRAYYNWLTR QRY                                              33

SEQ ID NO: 78           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 78
APEKPEEDAS AEELQRYYVA LRHYYNWLTR QRY                                              33

SEQ ID NO: 79           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                           substituent: [2-
                           (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 79
APEKPEEDAS AEELQRYYVT LRHYYNWLTR QRY                                        33

SEQ ID NO: 80           moltype = AA  length = 33
FEATURE                 Location/Qualifiers
REGION                  1..33
                        note = Description of Artificial Sequence: Synthetic PPY
                           analogue polypeptide
SITE                    1
                        note = N-term 3-methylbutanoyl
SITE                    4
                        note = The epsilon amino group of Lys has the following
                           substituent: [2-
                           (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 80
APEKPGEDAS PEELQRYYVS LRHYYNALTR QRY                                        33

SEQ ID NO: 81           moltype = AA  length = 33
FEATURE                 Location/Qualifiers
REGION                  1..33
                        note = Description of Artificial Sequence: Synthetic PPY
                           analogue polypeptide
SITE                    1
                        note = N-term 3-methylbutanoyl
SITE                    4
                        note = The epsilon amino group of Lys has the following
                           substituent: [2-
                           (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 81
APEKPEEDAS EEELQRYYVE LRHYYNWLTR QRY                                        33

SEQ ID NO: 82           moltype = AA  length = 33
FEATURE                 Location/Qualifiers
REGION                  1..33
                        note = Description of Artificial Sequence: Synthetic PPY
                           analogue polypeptide
SITE                    1
                        note = N-term 3-methylbutanoyl
SITE                    4
                        note = The epsilon amino group of Lys has the following
                           substituent: [2-
                           (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 82
APEKPEEDAE PEELQQYYVT LRHYYNWLTR QRY                                     33

SEQ ID NO: 83           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 83
APEKPEEEAS EEELQRYYVS LRHYYNWLTR QRY                                     33

SEQ ID NO: 84           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 84
APEKPEEEAS PEETQRYYVS LRHYYNWLTR QRY                                     33

SEQ ID NO: 85           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 85
APEKPEEDAS PEELQRYYVS IRHYYNWLTR QRY                                     33

SEQ ID NO: 86           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 86
APEKPEEDAS PEALQRYYVA LRHYYNWLTR QRY                                         33

SEQ ID NO: 87           moltype = AA   length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 87
APEKPEADAS PAELQRYYVS LRHYYNWLTR QRY                                         33

SEQ ID NO: 88           moltype = AA   length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 88
APEKPEEDAS PEEIQRYYVS LRHYYNWLTR QRY                                         33

SEQ ID NO: 89           moltype = AA   length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 89
APEKPEEDAS PEELQRYAVS LRHYYNWLTR QRY                              33

SEQ ID NO: 90           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 90
APEKPEADAS PEELQRYEVS LRHYYNWLTR QRY                              33

SEQ ID NO: 91           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 91
APEKPEEDSS PAELQRYYVS LRHYYNWLTR QRY                              33

SEQ ID NO: 92           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 92
APEKPPEDAS PEELQRYYVE LRHYYNWLTR QRY                              33

SEQ ID NO: 93           moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 93
APEKPEEEAE PEELQRYYVS LRHYYNWLTR QRY                                             33

SEQ ID NO: 94                 moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 94
APEKPEEDAS PEELQRYEVS LRHYYNWLTR QRY                                             33

SEQ ID NO: 95                 moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 95
APEKPEEDAP AEELQRYYVE LRHYYNWLTR QRY                                             33

SEQ ID NO: 96                 moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
```

```
SEQUENCE: 96
APEKPEEDTS PEELQRYYVS LRHYYNWLTR QRY                                    33

SEQ ID NO: 97           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 97
APEKPEEDAS AEELQKYYVS LRHYYNWLTR QRY                                    33

SEQ ID NO: 98           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 98
APEKPEEDAS PEETQRYYVE LRHYYNWLTR QRY                                    33

SEQ ID NO: 99           moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 99
APEKPEEDAS PAEIQRYYVS LRHYYNWLTR QRY                                    33

SEQ ID NO: 100          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 100
APEKPEADAS PEELQRYYVS LRHYYNWLTR QRY                                         33

SEQ ID NO: 101          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 101
APEKPEEDAS PEELQRYYVA LRHYYNWLTR QRY                                         33

SEQ ID NO: 102          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 102
APEKPEEDAS PEELQRYYSA LRHYYNWLTR QRY                                         33

SEQ ID NO: 103          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 103
APEKPEEDAE AEELQRYYVS LRHYYNWLTR QRY                                    33

SEQ ID NO: 104           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 104
APAKPPEDAS PEELQRYYVS LRHYYNWLTR QRY                                    33

SEQ ID NO: 105           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 105
APEKPEEDAT PEELQRYYVE LRHYYNWLTR QRY                                    33

SEQ ID NO: 106           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                           )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 106
APEKPEEDAS PEELQRYYVT LRHYYNWLTR QRY                                    33

SEQ ID NO: 107           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
```

```
                                note = The epsilon amino group of Lys has the following
                                  substituent: [2-
                                  (2-

)butan amido]ethoxy
ethoxy)acetamido]ethoxy
ethoxy)acetyl
SITE                            33
                                note = C-term amidation
source                          1..33
                                mol_type = protein
                                organism = synthetic construct
SEQUENCE: 107
APAKPEEDAS EEELQRYYVS LRHYYNWLTR QRY                                        33

SEQ ID NO: 108                  moltype = AA  length = 33
FEATURE                         Location/Qualifiers
REGION                          1..33
                                note = Description of Artificial Sequence: Synthetic PPY
                                  analogue polypeptide
SITE                            1
                                note = N-term 3-methylbutanoyl
SITE                            4
                                note = The epsilon amino group of Lys has the following
                                  substituent: [2-
                                  (2-

)butan amido]ethoxy
ethoxy)acetamido]ethoxy
ethoxy)acetyl
SITE                            33
                                note = C-term amidation
source                          1..33
                                mol_type = protein
                                organism = synthetic construct
SEQUENCE: 108
APEKPEEDAS AEELQRYYVS LRHYYNWLTR QRY                                        33

SEQ ID NO: 109                  moltype = AA  length = 33
FEATURE                         Location/Qualifiers
REGION                          1..33
                                note = Description of Artificial Sequence: Synthetic PPY
                                  analogue polypeptide
SITE                            1
                                note = N-term 3-methylbutanoyl
SITE                            4
                                note = The epsilon amino group of Lys has the following
                                  substituent: [2-
                                  (2-

)butan amido]ethoxy
ethoxy)acetamido]ethoxy
ethoxy)acetyl
SITE                            33
                                note = C-term amidation
source                          1..33
                                mol_type = protein
                                organism = synthetic construct
SEQUENCE: 109
APEKPEEDAE PEELQEYYVS LRHYYNWLTR QRY                                        33

SEQ ID NO: 110                  moltype = AA  length = 33
FEATURE                         Location/Qualifiers
REGION                          1..33
                                note = Description of Artificial Sequence: Synthetic PPY
                                  analogue polypeptide
SITE                            1
                                note = N-term 3-methylbutanoyl
SITE                            4
                                note = The epsilon amino group of Lys has the following
                                  substituent: [2-
                                  (2-

)butan amido]ethoxy
ethoxy)acetamido]ethoxy
ethoxy)acetyl
SITE                            33
                                note = C-term amidation
source                          1..33
                                mol_type = protein
                                organism = synthetic construct
```

```
SEQUENCE: 110
APAKPEEDAT PEELQRYYVS LRHYYNWLTR QRY                                33

SEQ ID NO: 111          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 111
APEKPEEDAS PEELQKYYVA LRHYYNWLTR QRY                                33

SEQ ID NO: 112          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 112
APEKPEEDAS PEELQRYYVE LRHYYNWLTR QRY                                33

SEQ ID NO: 113          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 113
APEKPEEAAS PEELQRYYVS LRHYYNWLTR QRY                                33

SEQ ID NO: 114          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

-continued

```
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 114
APEKPEEDAE PEEIQRYYVS LRHYYNWLTR QRY                                           33

SEQ ID NO: 115                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 115
APEKPEEDAE PEELQRYYVE LRHYYNWLTR QRY                                           33

SEQ ID NO: 116                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 116
APEKPEEDAT PEELQRYYVS LRHYYNWLTR QRY                                           33

SEQ ID NO: 117                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
```

```
SEQUENCE: 117
APEKAEEDAT PEELQRYYVS LRHYYNWLTR QRY                                33

SEQ ID NO: 118          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 118
APEKPEEDAS PEELQRYYVS LRHYHWYLTR QRY                                33

SEQ ID NO: 119          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 119
APEKPEEEAS PEALQRYYVS LRHYYNWLTR QRY                                33

SEQ ID NO: 120          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 120
APEKPEEDAA AEELQRYYVS LRHYYNWLTR QRY                                33

SEQ ID NO: 121          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                          substituent: [2-
                          (2-
                              )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 121
APAKPEEDAS PEELQRYYVA LRHYYNWLTR QRY                                33

SEQ ID NO: 122          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                              )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 122
APEKPEEDAS AAELQRYYVS LRHYYNWLTR QRY                                33

SEQ ID NO: 123          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                              )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 123
APEKPEEEAS PEELQRYYVT LRHYYNWLTR QRY                                33

SEQ ID NO: 124          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                              )butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 124
APEKPGEDAE EEELQEYYVS LRHYYNWLTR QRY                              33

SEQ ID NO: 125          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 125
APAKPEADAS PEELQRYYVS LRHYYNWLTR QRY                              33

SEQ ID NO: 126          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 126
APEKPEEDAA PEELQRYYVS LRHYYNWLTR QRY                              33

SEQ ID NO: 127          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 127
APEKPEEDAS PEELQRYYVS LRHYWYHLTR QRY                              33

SEQ ID NO: 128          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 128
APEKPEEDAA PEEIQRYYVS LRHYYNWLTR QRY                                              33

SEQ ID NO: 129          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 129
APEKPGEDAS PEELQRYYVS LRHYYNWATR QRY                                              33

SEQ ID NO: 130          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 130
APAKPEEDSS PEELQRYYVS LRHYYNWLTR QRY                                              33

SEQ ID NO: 131          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 131
APAKPEEDAS AEELQRYYVS LRHYYNWLTR QRY                              33

SEQ ID NO: 132           moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 132
APEKPEEDAP AEEIQRYYVS LRHYYNWLTR QRY                              33

SEQ ID NO: 133           moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 133
APEKPEEDAS PEETQRYYTA LRHYYNWLTR QRY                              33

SEQ ID NO: 134           moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
                         note = The epsilon amino group of Lys has the following
                          substituent: [2-
                          (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 134
APEKPEEDTS AEELQRYYVS LRHYYNWLTR QRY                              33

SEQ ID NO: 135           moltype = AA  length = 33
FEATURE                  Location/Qualifiers
REGION                   1..33
                         note = Description of Artificial Sequence: Synthetic PPY
                          analogue polypeptide
SITE                     1
                         note = N-term 3-methylbutanoyl
SITE                     4
```

```
                            note = The epsilon amino group of Lys has the following
                              substituent: [2-
                              (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 135
APEKAEEDAS PEELQRYYVE LRHYYNWLTR QRY                                        33

SEQ ID NO: 136              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 136
APEKPEEDAS PEELQKYYVT LRHYYNWLTR QRY                                        33

SEQ ID NO: 137              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 137
APEKPEEDAS PEEVQRYYVE LRHYYNWLTR QRY                                        33

SEQ ID NO: 138              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
```

```
SEQUENCE: 138
APEKPEEDAS PEEIQRYYTE LRHYYNWLTR QRY                        33

SEQ ID NO: 139          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 139
APEKPEADAS PEELQRYYVE LRHYYNWLTR QRY                        33

SEQ ID NO: 140          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 140
APEKPEADSS PEELQRYYVS LRHYYNWLTR QRY                        33

SEQ ID NO: 141          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 141
APEKPEEDAS PEELQRYYVS LRHYYNWITR QRY                        33

SEQ ID NO: 142          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 142
APAKPEEDAS PEELQQYYVS LRHYYNWLTR QRY                                      33

SEQ ID NO: 143          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 143
APEKPEEESS PEELQRYYVS LRHYYNWLTR QRY                                      33

SEQ ID NO: 144          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 144
APEKPGEDAS PEELEQYYVS LRHYYNWLTR QRY                                      33

SEQ ID NO: 145          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
```

-continued

```
SEQUENCE: 145
APEKPEEAAS PEELQRYYVS ARHYYNWLTR QRY                                    33

SEQ ID NO: 146          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 146
APEKPPEEAS PEELQRYYVS LRHYYNWLTR QRY                                    33

SEQ ID NO: 147          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 147
APEKPEEDAT PEELQRYYVA LRHYYNWLTR QRY                                    33

SEQ ID NO: 148          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 148
APEKAEEDAS PEELQQYYVS LRHYYNWLTR QRY                                    33

SEQ ID NO: 149          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 149
APEKPEEDSS PEEIQRYYVS LRHYYNWLTR QRY                                          33

SEQ ID NO: 150              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 150
APEKPEEEAS PEELQRYYVS TRHYYNWLTR QRY                                          33

SEQ ID NO: 151              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 151
APEKPEEDAS PEETQKYYVS LRHYYNWLTR QRY                                          33

SEQ ID NO: 152              moltype = AA  length = 33
FEATURE                     Location/Qualifiers
REGION                      1..33
                            note = Description of Artificial Sequence: Synthetic PPY
                              analogue polypeptide
SITE                        1
                            note = N-term 3-methylbutanoyl
SITE                        4
                            note = The epsilon amino group of Lys has the following
                              substituent: [2-
                              (2-
                            )butan amido]ethoxy
ethoxy)acetamido]ethoxy
ethoxy)acetyl
SITE                        33
                            note = C-term amidation
source                      1..33
                            mol_type = protein
                            organism = synthetic construct
```

```
SEQUENCE: 152
APEKPEEDAP AEELQRYYVS LRHYYNWLTR QRY                              33

SEQ ID NO: 153          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 153
APEKPEEAAS PEELQRYYVE LRHYYNWLTR QRY                              33

SEQ ID NO: 154          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 154
APEKPEEDAE PEELQKYYVS LRHYYNWLTR QRY                              33

SEQ ID NO: 155          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 155
APEKPEAEAS PEELQRYYVS LRHYYNWLTR QRY                              33

SEQ ID NO: 156          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 156
APEKAEEDAS PEEIQRYYVS LRHYYNWLTR QRY                                      33

SEQ ID NO: 157          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 157
APEKVEEEAS PEELQRYYVS LRHYYNWLTR QRY                                      33

SEQ ID NO: 158          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 158
APEKPEEEAS PEELQRYEVS LRHYYNWLTR QRY                                      33

SEQ ID NO: 159          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 159
APEKPEEDAS PEETQRYYVS LRHYYNWLTR QRY                                  33

SEQ ID NO: 160          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 160
APEKPEEDAS EEELEQYYVS LRHYYNWLTR QRY                                  33

SEQ ID NO: 161          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 161
APAKPEEDAS PEETQRYYVS LRHYYNWLTR QRY                                  33

SEQ ID NO: 162          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 162
APEKPEEDAS PEELQRYYVS LRHYWNYLTR QRY                                  33

SEQ ID NO: 163          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                            note = The epsilon amino group of Lys has the following
                               substituent: [2-
                               (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 163
APEKPEADAS PEELEQYYVS LRHYYNWLTR QRY                                             33

SEQ ID NO: 164              moltype = AA  length = 33
FEATURE                     Location/Qualifiers
REGION                      1..33
                            note = Description of Artificial Sequence: Synthetic PPY
                               analogue polypeptide
SITE                        1
                            note = N-term 3-methylbutanoyl
SITE                        4
                            note = The epsilon amino group of Lys has the following
                               substituent: [2-
                               (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 164
APEKPEADAE PEELQRYYTS LRHYYNWLTR QRY                                             33

SEQ ID NO: 165              moltype = AA  length = 33
FEATURE                     Location/Qualifiers
REGION                      1..33
                            note = Description of Artificial Sequence: Synthetic PPY
                               analogue polypeptide
SITE                        1
                            note = N-term 3-methylbutanoyl
SITE                        4
                            note = The epsilon amino group of Lys has the following
                               substituent: [2-
                               (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
SEQUENCE: 165
APEKPEEDAT PEELQQYYVS LRHYYNWLTR QRY                                             33

SEQ ID NO: 166              moltype = AA  length = 33
FEATURE                     Location/Qualifiers
REGION                      1..33
                            note = Description of Artificial Sequence: Synthetic PPY
                               analogue polypeptide
SITE                        1
                            note = N-term 3-methylbutanoyl
SITE                        4
                            note = The epsilon amino group of Lys has the following
                               substituent: [2-
                               (2-

)butan amido]ethoxy
ethoxy)acetamido]ethoxy
ethoxy)acetyl
SITE                        33
                            note = C-term amidation
source                      1..33
                            mol_type = protein
                            organism = synthetic construct
```

```
SEQUENCE: 166
APEKPEEDAS PEELQRYEVS LRAYYNWLTR QRY                                 33

SEQ ID NO: 167          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 167
APEKPEEAAS PEELQRYYVA LRHYYNWLTR QRY                                 33

SEQ ID NO: 168          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 168
APEKPEEDAS EEELQEYYVS LRHYYNWLTR QRY                                 33

SEQ ID NO: 169          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-
                          )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 169
APEKPEEDAS PEELQRYQVS LRHYYNWLTR QRY                                 33

SEQ ID NO: 170          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
```

```
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
SEQUENCE: 170
APEKPPADAS PEELQRYYVE LRHYYNWLTR QRY                                            33

SEQ ID NO: 171             moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
SEQUENCE: 171
APEKPEEDAS PEELQQYEVS LRHYYNWLTR QRY                                            33

SEQ ID NO: 172             moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
SEQUENCE: 172
APEKPEEDAE PEELQRYYVS LRHYYNWITR QRY                                            33

SEQ ID NO: 173             moltype = AA  length = 33
FEATURE                    Location/Qualifiers
REGION                     1..33
                           note = Description of Artificial Sequence: Synthetic PPY
                             analogue polypeptide
SITE                       1
                           note = N-term 3-methylbutanoyl
SITE                       4
                           note = The epsilon amino group of Lys has the following
                             substituent: [2-
                             (2-

)butan amido]ethoxy
ethoxy)acetamido]ethoxy
ethoxy)acetyl
SITE                       33
                           note = C-term amidation
source                     1..33
                           mol_type = protein
                           organism = synthetic construct
```

```
SEQUENCE: 173
APEKPEEEAS PEELQRYYVA LRHYYNWLTR QRY                                         33

SEQ ID NO: 174          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 174
APEKPEEEAS PEELEQYYVS LRHYYNWLTR QRY                                         33

SEQ ID NO: 175          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 175
APEKPEEDAT PEEIQRYYVS LRHYYNWLTR QRY                                         33

SEQ ID NO: 176          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 176
APEKPEEDAE PEELQRYYVA LRHYYNWLTR QRY                                         33

SEQ ID NO: 177          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 177
APAKPEEDAS PEELQRYYVE LRHYYNWLTR QRY                                     33

SEQ ID NO: 178          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 178
APAKPEEDAE PEELQRYYVS LRHYYNWLTR QRY                                     33

SEQ ID NO: 179          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 179
APEKPEEDAA PEELQRYYVA LRHYYNWLTR QRY                                     33

SEQ ID NO: 180          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 180
APEKPEEDAS EEELQRYYVS LRHYYNWLTR QRY                                33

SEQ ID NO: 181          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 181
APEKPEEDSS PEELQRYYVE LRHYYNWLTR QRY                                33

SEQ ID NO: 182          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 182
APEKPEEDAT PEETERYYVS LRHYYNWLTR QRY                                33

SEQ ID NO: 183          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 183
APAKPEEDAS PAELQRYYVS LRHYYNWLTR QRY                                33

SEQ ID NO: 184          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
```

```
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 184
APEKPEEDAS PEETQQYYVS LRHYYNWLTR QRY                                 33

SEQ ID NO: 185          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 185
APEKPEADAS PEELQRYYVA LRHYYNWLTR QRY                                 33

SEQ ID NO: 186          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 186
APEKPEEDGS PEELQRYYVE LRHYYNWLTR QRY                                 33

SEQ ID NO: 187          moltype = AA  length = 33
FEATURE                 Location/Qualifiers
REGION                  1..33
                        note = Description of Artificial Sequence: Synthetic PPY
                          analogue polypeptide
SITE                    1
                        note = N-term 3-methylbutanoyl
SITE                    4
                        note = The epsilon amino group of Lys has the following
                          substituent: [2-
                          (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
```

```
SEQUENCE: 187
APEKPPEDAS PEELQRYYVS LRHYYNWLTR QRY                                          33

SEQ ID NO: 188           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 188
APEKPEEAAS PEELQRYYVT LRHYYNWLTR QRY                                          33

SEQ ID NO: 189           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 189
APEKPEEEAS PEELQRYYVE LRHYYNWLTR QRY                                          33

SEQ ID NO: 190           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
                         note = The epsilon amino group of Lys has the following
                           substituent: [2-
                           (2-
                         )butan amido]ethoxy
ethoxy)acetamido]ethoxy
ethoxy)acetyl
SITE                     33
                         note = C-term amidation
source                   1..33
                         mol_type = protein
                         organism = synthetic construct
SEQUENCE: 190
APEKPEEDAS AEELQRYYVE LRHYYNWLTR QRY                                          33

SEQ ID NO: 191           moltype = AA  length = 33
FEATURE                  Location/Qualifiers
REGION                   1..33
                         note = Description of Artificial Sequence: Synthetic PPY
                           analogue polypeptide
SITE                     1
                         note = N-term 3-methylbutanoyl
SITE                     4
```

```
                          note = The epsilon amino group of Lys has the following
                             substituent: [2-
                             (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 191
APEKPEEDAS PEELQRYYVS LRHQYNWLTR QRY                                        33

SEQ ID NO: 192            moltype = AA  length = 33
FEATURE                   Location/Qualifiers
REGION                    1..33
                          note = Description of Artificial Sequence: Synthetic PPY
                            analogue polypeptide
SITE                      1
                          note = N-term 3-methylbutanoyl
SITE                      4
                          note = The epsilon amino group of Lys has the following
                             substituent: [2-
                             (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 192
APEKPEEDAE PEELQRYYVS LRHYYNWLTR QRY                                        33

SEQ ID NO: 193            moltype = AA  length = 33
FEATURE                   Location/Qualifiers
REGION                    1..33
                          note = Description of Artificial Sequence: Synthetic PPY
                            analogue polypeptide
SITE                      1
                          note = N-term 3-methylbutanoyl
SITE                      4
                          note = The epsilon amino group of Lys has the following
                             substituent: [2-
                             (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 193
APEKPEEDAS EAELQRYYVS LRHYYNWLTR QRY                                        33

SEQ ID NO: 194            moltype = AA  length = 33
FEATURE                   Location/Qualifiers
REGION                    1..33
                          note = Description of Artificial Sequence: Synthetic PPY
                            analogue polypeptide
SITE                      1
                          note = N-term 3-methylbutanoyl
SITE                      4
                          note = The epsilon amino group of Lys has the following
                             substituent: [2-
                             (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
```

```
SEQUENCE: 194
APEKPEEEAP PEELQRYYVS LRHYYNWLTR QRY                                              33

SEQ ID NO: 195          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 195
APEKPEEDAS PEELQRYYIS LRHYYNWLTR QRY                                              33

SEQ ID NO: 196          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 196
APEKPEEDAA PAELQRYYVS LRHYYNWLTR QRY                                              33

SEQ ID NO: 197          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 197
APEKPEEDAS EEEIQRYYVS LRHYYNWLTR QRY                                              33

SEQ ID NO: 198          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    2
```

```
                              note = (4R)-4-hydroxy-L-proline
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 198
AXEKPEEDAS PEELQRYYVS LRHYYNWTLR QRY                                           33

SEQ ID NO: 199                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 199
APEKPEEDAS PEALQRYYVE LRHYYNWLTR QRY                                           33

SEQ ID NO: 200                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 200
APAKPPEDAE PEELQRYYVS LRHYYNWLTR QRY                                           33

SEQ ID NO: 201                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
```

```
                        mol_type = protein
                        organism = synthetic construct
SEQUENCE: 201
APAKPEADAS PEELQRYYVE LRHYYNWLTR QRY                                33

SEQ ID NO: 202          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 202
APEKPEEDAE PEALQRYYVS LRHYYNWLTR QRY                                33

SEQ ID NO: 203          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 203
APEKPEEDAE PEETQRYYVS LRHYYNWLTR QRY                                33

SEQ ID NO: 204          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    5
                        note = (4R)-4-hydroxy-L-proline
SITE                    33
                        note = C-term amidation
source                  1..33
                        mol_type = protein
                        organism = synthetic construct
SEQUENCE: 204
APEKXEEDAS PEELQRYYVS LRHYYNWLTR QRY                                33

SEQ ID NO: 205          moltype = AA   length = 33
FEATURE                 Location/Qualifiers
REGION                  1..33
                        note = Description of Artificial Sequence: Synthetic PPY
```

```
                          analogue polypeptide
SITE                      1
                          note = N-term 3-methylbutanoyl
SITE                      4
                          note = The epsilon amino group of Lys has the following
                           substituent: [2-
                           (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 205
APEKPQEDAE PEELQEYYVS LRHYYNWLTR QRY                                        33

SEQ ID NO: 206            moltype = AA  length = 33
FEATURE                   Location/Qualifiers
REGION                    1..33
                          note = Description of Artificial Sequence: Synthetic PPY
                           analogue polypeptide
SITE                      1
                          note = N-term 3-methylbutanoyl
SITE                      4
                          note = The epsilon amino group of Lys has the following
                           substituent: [2-
                           (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 206
APEKPEEDAA PEELQKYYVS LRHYYNWLTR QRY                                        33

SEQ ID NO: 207            moltype = AA  length = 33
FEATURE                   Location/Qualifiers
REGION                    1..33
                          note = Description of Artificial Sequence: Synthetic PPY
                           analogue polypeptide
SITE                      1
                          note = N-term 3-methylbutanoyl
SITE                      4
                          note = The epsilon amino group of Lys has the following
                           substituent: [2-
                           (2-

)butan amido]ethoxy
ethoxy)acetamido]ethoxy
ethoxy)acetyl
SITE                      33
                          note = C-term amidation
source                    1..33
                          mol_type = protein
                          organism = synthetic construct
SEQUENCE: 207
APAKPEEDAS PEELQRYYVS LRHYYNWLTR QRY                                        33

SEQ ID NO: 208            moltype = AA  length = 33
FEATURE                   Location/Qualifiers
REGION                    1..33
                          note = Description of Artificial Sequence: Synthetic PPY
                           analogue polypeptide
SITE                      1
                          note = N-term 3-methylbutanoyl
SITE                      4
                          note = The epsilon amino group of Lys has the following
                           substituent: [2-
                           (2-

)butan amido]ethoxy
ethoxy)acetamido]ethoxy
ethoxy)acetyl
SITE                      33
```

```
                        note = C-term amidation
source                  1..33
                        mol_type = protein
                        organism = synthetic construct
SEQUENCE: 208
APEKPEEEAS PEEVQRYYVS LRHYYNWLTR QRY                                   33

SEQ ID NO: 209          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 209
APEKPEEEAS PEELQKYYVS LRHYYNWLTR QRY                                   33

SEQ ID NO: 210          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 210
APEKPEEDAS PEELEQYEVS LRHYYNWLTR QRY                                   33

SEQ ID NO: 211          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 211
APAKPEADAE PEELQRYYVS LRHYYNWLTR QRY                                   33

SEQ ID NO: 212          moltype = AA  length = 33
FEATURE                 Location/Qualifiers
REGION                  1..33
                        note = Description of Artificial Sequence: Synthetic PPY
```

```
                                    analogue polypeptide
SITE                                1
                                    note = N-term 3-methylbutanoyl
SITE                                4
                                    note = The epsilon amino group of Lys has the following
                                     substituent: [2-
                                     (2-

)butan amido]ethoxy
ethoxy)acetamido]ethoxy
ethoxy)acetyl
SITE                                33
                                    note = C-term amidation
source                              1..33
                                    mol_type = protein
                                    organism = synthetic construct
SEQUENCE: 212
APEKPEEDAS EEETQRYYVS LRHYYNWLTR QRY                                           33

SEQ ID NO: 213                      moltype = AA  length = 33
FEATURE                             Location/Qualifiers
REGION                              1..33
                                    note = Description of Artificial Sequence: Synthetic PPY
                                     analogue polypeptide
SITE                                1
                                    note = N-term 3-methylbutanoyl
SITE                                4
                                    note = The epsilon amino group of Lys has the following
                                     substituent: [2-
                                     (2-

)butan amido]ethoxy
ethoxy)acetamido]ethoxy
ethoxy)acetyl
SITE                                33
                                    note = C-term amidation
source                              1..33
                                    mol_type = protein
                                    organism = synthetic construct
SEQUENCE: 213
APEKPEEDSE PEELQRYYVS LRHYYNWLTR QRY                                           33

SEQ ID NO: 214                      moltype = AA  length = 33
FEATURE                             Location/Qualifiers
REGION                              1..33
                                    note = Description of Artificial Sequence: Synthetic PPY
                                     analogue polypeptide
SITE                                1
                                    note = N-term 3-methylbutanoyl
SITE                                4
                                    note = The epsilon amino group of Lys has the following
                                     substituent: [2-
                                     (2-

)butan amido]ethoxy
ethoxy)acetamido]ethoxy
ethoxy)acetyl
SITE                                33
                                    note = C-term amidation
source                              1..33
                                    mol_type = protein
                                    organism = synthetic construct
SEQUENCE: 214
APEKIEEEAS PEELQRYYVS LRHYYNWLTR QRY                                           33

SEQ ID NO: 215                      moltype = AA  length = 33
FEATURE                             Location/Qualifiers
REGION                              1..33
                                    note = Description of Artificial Sequence: Synthetic PPY
                                     analogue polypeptide
SITE                                1
                                    note = N-term 3-methylbutanoyl
SITE                                4
                                    note = The epsilon amino group of Lys has the following
                                     substituent: [2-
                                     (2-

)butan amido]ethoxy
ethoxy)acetamido]ethoxy
ethoxy)acetyl
SITE                                33
```

```
                              note = C-term amidation
source                        1..33
                              mol_type = protein
                              organism = synthetic construct
SEQUENCE: 215
APEKPEEDAT AEELQRYYVS LRHYYNWLTR QRY                                  33

SEQ ID NO: 216                moltype = AA  length = 33
FEATURE                       Location/Qualifiers
REGION                        1..33
                              note = Description of Artificial Sequence: Synthetic PPY
                               analogue polypeptide
SITE                          1
                              note = N-term 3-methylbutanoyl
SITE                          4
                              note = The epsilon amino group of Lys has the following
                               substituent: [2-
                               (2-
                              )butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 216
APEKPEEDTA PEELQRYYVS LRHYYNWLTR QRY                                  33

SEQ ID NO: 217                moltype = AA  length = 33
FEATURE                       Location/Qualifiers
REGION                        1..33
                              note = Description of Artificial Sequence: Synthetic PPY
                               analogue polypeptide
SITE                          1
                              note = N-term 3-methylbutanoyl
SITE                          4
                              note = The epsilon amino group of Lys has the following
                               substituent: [2-
                               (2-
                              )butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 217
APEKPEEETS PEELQRYYVS LRHYYNWLTR QRY                                  33

SEQ ID NO: 218                moltype = AA  length = 33
FEATURE                       Location/Qualifiers
REGION                        1..33
                              note = Description of Artificial Sequence: Synthetic PPY
                               analogue polypeptide
SITE                          1
                              note = N-term 3-methylbutanoyl
SITE                          4
                              note = The epsilon amino group of Lys has the following
                               substituent: [2-
                               (2-
                              )butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 218
APEKPEEDAS EEELQRYYVA LRHYYNWLTR QRY                                  33

SEQ ID NO: 219                moltype = AA  length = 33
FEATURE                       Location/Qualifiers
REGION                        1..33
                              note = Description of Artificial Sequence: Synthetic PPY
```

```
                              analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 219
APEKPEEDAS PAELQRYYVE LRHYYNWLTR QRY                                          33

SEQ ID NO: 220          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 220
APAKPEEDAS PEELEQYYVS LRHYYNWLTR QRY                                          33

SEQ ID NO: 221          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 221
APEKPEEDAS PAELQRYYVA LRHYYNWLTR QRY                                          33

SEQ ID NO: 222          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
```

```
                        note = C-term amidation
source                  1..33
                        mol_type = protein
                        organism = synthetic construct
SEQUENCE: 222
APEKPEEDSS PEELQRYYVA LRHYYNWLTR QRY                                        33

SEQ ID NO: 223          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 223
APEKPEEEAA PEELQRYYVS LRHYYNWLTR QRY                                        33

SEQ ID NO: 224          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 224
APEKPEEAAS AEELQRYYVS LRHYYNWLTR QRY                                        33

SEQ ID NO: 225          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 225
APEKPEEDAP EEELQRYYVS LRHYYNWLTR QRY                                        33

SEQ ID NO: 226          moltype = AA  length = 33
FEATURE                 Location/Qualifiers
REGION                  1..33
                        note = Description of Artificial Sequence: Synthetic PPY
```

```
                        analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 226
APEKPEEDAS AEELQQYYVS LRHYYNWLTR QRY                                       33

SEQ ID NO: 227          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 227
APEKPEEAAE PEELQRYYVS LRHYYNWLTR QRY                                       33

SEQ ID NO: 228          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 228
APEKPGEEAS PEELEQYYVS LRHYYNWLTR QRY                                       33

SEQ ID NO: 229          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
```

```
                    note = C-term amidation
source              1..33
                    mol_type = protein
                    organism = synthetic construct
SEQUENCE: 229
APEKPGEDAE PEELEQYYVS LRHYYNWLTR QRY                                      33

SEQ ID NO: 230      moltype = AA  length = 33
FEATURE             Location/Qualifiers
REGION              1..33
                    note = Description of Artificial Sequence: Synthetic PPY
                     analogue polypeptide
SITE                1
                    note = N-term 3-methylbutanoyl
SITE                4
                    note = The epsilon amino group of Lys has the following
                     substituent: [2-
                     (2-
                    )butan amido]ethoxy
ethoxy)acetamido]ethoxy
ethoxy)acetyl
SITE                33
                    note = C-term amidation
source              1..33
                    mol_type = protein
                    organism = synthetic construct
SEQUENCE: 230
APEKPEEAAS PEETQRYYVS LRHYYNWLTR QRY                                      33

SEQ ID NO: 231      moltype = AA  length = 33
FEATURE             Location/Qualifiers
REGION              1..33
                    note = Description of Artificial Sequence: Synthetic PPY
                     analogue polypeptide
SITE                1
                    note = N-term 3-methylbutanoyl
SITE                4
                    note = The epsilon amino group of Lys has the following
                     substituent: [2-
                     (2-
                    )butan amido]ethoxy
ethoxy)acetamido]ethoxy
ethoxy)acetyl
SITE                33
                    note = C-term amidation
source              1..33
                    mol_type = protein
                    organism = synthetic construct
SEQUENCE: 231
APEKAEEDAS PEELEQYYVS LRHYYNWLTR QRY                                      33

SEQ ID NO: 232      moltype = AA  length = 33
FEATURE             Location/Qualifiers
REGION              1..33
                    note = Description of Artificial Sequence: Synthetic PPY
                     analogue polypeptide
SITE                1
                    note = N-term 3-methylbutanoyl
SITE                4
                    note = The epsilon amino group of Lys has the following
                     substituent: [2-
                     (2-
                    )butan amido]ethoxy
ethoxy)acetamido]ethoxy
ethoxy)acetyl
SITE                33
                    note = C-term amidation
source              1..33
                    mol_type = protein
                    organism = synthetic construct
SEQUENCE: 232
APEKPEEDAS PEELQQYYVS LRAYYNWLTR QRY                                      33

SEQ ID NO: 233      moltype = AA  length = 33
FEATURE             Location/Qualifiers
REGION              1..33
                    note = Description of Artificial Sequence: Synthetic PPY
```

```
                              analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 233
APEKPEEDAS PEELQRYYVS ARHYYNWLTR QRY                                         33

SEQ ID NO: 234                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 234
APEKPEEDAS PEEIQRYYVA LRHYYNWLTR QRY                                         33

SEQ ID NO: 235                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
                              note = C-term amidation
source                        1..33
                              mol_type = protein
                              organism = synthetic construct
SEQUENCE: 235
APEKPEEDAT PEELQKYYVS LRHYYNWLTR QRY                                         33

SEQ ID NO: 236                moltype = AA  length = 33
FEATURE                       Location/Qualifiers
REGION                        1..33
                              note = Description of Artificial Sequence: Synthetic PPY
                                analogue polypeptide
SITE                          1
                              note = N-term 3-methylbutanoyl
SITE                          4
                              note = The epsilon amino group of Lys has the following
                                substituent: [2-
                                (2-

)butan amido]ethoxy
ethoxy)acetamido]ethoxy
ethoxy)acetyl
SITE                          33
```

-continued

```
                        note = C-term amidation
source                  1..33
                        mol_type = protein
                        organism = synthetic construct
SEQUENCE: 236
APAKPPEDAS PEELQRYYVE LRHYYNWLTR QRY                                 33

SEQ ID NO: 237          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 237
APEKPEEAAS PEELQQYYVS LRHYYNWLTR QRY                                 33

SEQ ID NO: 238          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 238
APAKPEEEAS PEELQRYYVS LRHYYNWLTR QRY                                 33

SEQ ID NO: 239          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                        )butan amido]ethoxy
ethoxy)acetamido]ethoxy
ethoxy)acetyl
SITE                    11
                        note = (4R)-4-hydroxy-L-proline
SITE                    33
                        note = C-term amidation
source                  1..33
                        mol_type = protein
                        organism = synthetic construct
SEQUENCE: 239
APEKPEEDAS XEELQRYYVS LRHYYNWLTR QRY                                 33

SEQ ID NO: 240          moltype = AA  length = 33
FEATURE                 Location/Qualifiers
```

```
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 240
APEKPEEEAP AEELQRYYVS LRHYYNWLTR QRY                                       33

SEQ ID NO: 241          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 241
APEKPEEDAS PEELQRYYVE VRHYYNWLTR QRY                                       33

SEQ ID NO: 242          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 242
APEKTEEEAS PEELQRYYVS LRHYYNWLTR QRY                                       33

SEQ ID NO: 243          moltype = AA   length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
```

```
                      )butan amido]ethoxy
ethoxy)acetamido]ethoxy
ethoxy)acetyl
SITE                   33
                       note = C-term amidation
source                 1..33
                       mol_type = protein
                       organism = synthetic construct
SEQUENCE: 243
APEKPEEDAS EEELQRYEVS LRHYYNWLTR QRY                                   33

SEQ ID NO: 244         moltype = AA  length = 33
FEATURE                Location/Qualifiers
REGION                 1..33
                       note = Description of Artificial Sequence: Synthetic PPY
                         analogue polypeptide
SITE                   1
                       note = N-term 3-methylbutanoyl
SITE                   4
                       note = The epsilon amino group of Lys has the following
                         substituent: [2-
                         (2-
                      )butan amido]ethoxy
ethoxy)acetamido]ethoxy
ethoxy)acetyl
SITE                   33
                       note = C-term amidation
source                 1..33
                       mol_type = protein
                       organism = synthetic construct
SEQUENCE: 244
APEKPEEDAS PEALQRYYVS LRHYYNWLTR QRY                                   33

SEQ ID NO: 245         moltype = AA  length = 33
FEATURE                Location/Qualifiers
REGION                 1..33
                       note = Description of Artificial Sequence: Synthetic PPY
                         analogue polypeptide
SITE                   1
                       note = N-term 3-methylbutanoyl
SITE                   4
                       note = The epsilon amino group of Lys has the following
                         substituent: [2-
                         (2-
                      )butan amido]ethoxy
ethoxy)acetamido]ethoxy
ethoxy)acetyl
SITE                   33
                       note = C-term amidation
source                 1..33
                       mol_type = protein
                       organism = synthetic construct
SEQUENCE: 245
APEKPEEEAS PEEIQRYYVS LRHYYNWLTR QRY                                   33

SEQ ID NO: 246         moltype = AA  length = 33
FEATURE                Location/Qualifiers
REGION                 1..33
                       note = Description of Artificial Sequence: Synthetic PPY
                         analogue polypeptide
SITE                   1
                       note = N-term 3-methylbutanoyl
SITE                   4
                       note = The epsilon amino group of Lys has the following
                         substituent: [2-
                         (2-
                      )butan amido]ethoxy
ethoxy)acetamido]ethoxy
ethoxy)acetyl
SITE                   33
                       note = C-term amidation
source                 1..33
                       mol_type = protein
                       organism = synthetic construct
SEQUENCE: 246
APEKPEADAS AEELQRYYVS LRHYYNWLTR QRY                                   33

SEQ ID NO: 247         moltype = AA  length = 33
```

```
FEATURE                 Location/Qualifiers
REGION                  1..33
                        note = Description of Artificial Sequence: Synthetic PPY
                        analogue polypeptide
SITE                    1
                        note = N-term 3-methylbutanoyl
SITE                    4
                        note = The epsilon amino group of Lys has the following
                        substituent: [2-
                        (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 247
APEKPEEEAS PEELQQYYVS LRHYYNWLTR QRY                                        33

SEQ ID NO: 248          moltype = AA  length = 33
FEATURE                 Location/Qualifiers
REGION                  1..33
                        note = Description of Artificial Sequence: Synthetic PPY
                        analogue polypeptide
SITE                    1
                        note = N-term 3-methylbutanoyl
SITE                    4
                        note = The epsilon amino group of Lys has the following
                        substituent: [2-
                        (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 248
APEKPEEDAE PAELQRYYVS LRHYYNWLTR QRY                                        33

SEQ ID NO: 249          moltype = AA  length = 33
FEATURE                 Location/Qualifiers
REGION                  1..33
                        note = Description of Artificial Sequence: Synthetic PPY
                        analogue polypeptide
SITE                    1
                        note = N-term 3-methylbutanoyl
SITE                    4
                        note = The epsilon amino group of Lys has the following
                        substituent: [2-
                        (2-

)butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 249
RPEKPGEDAS PEELQRYYVS LRHYYNWLTR QRY                                        33

SEQ ID NO: 250          moltype = AA  length = 33
FEATURE                 Location/Qualifiers
REGION                  1..33
                        note = Description of Artificial Sequence: Synthetic PPY
                        analogue polypeptide
SITE                    1
                        note = N-term 3-methylbutanoyl
SITE                    4
                        note = The epsilon amino group of Lys has the following
                        substituent: [2-
                        (2-
```

```
SITE                    33
                        note = C-term amidation
source                  1..33
                        mol_type = protein
                        organism = synthetic construct
SEQUENCE: 250
RPEKPGEDAS PEELQRYYVS LAHYYNWLTR QRY                                   33

SEQ ID NO: 251          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 251
RPEKPGEDAS PEELQRYYVS LRAYYNWLTR QRY                                   33

SEQ ID NO: 252          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 252
RPEKPGEDAS PEELQRYYVS LRHYYNWLTA QRY                                   33

SEQ ID NO: 253          moltype = AA  length = 33
FEATURE                 Location/Qualifiers
REGION                  1..33
                        note = Description of Artificial Sequence: Synthetic PPY
                         analogue polypeptide
SITE                    1
                        note = N-term 3-methylbutanoyl
SITE                    4
                        note = The epsilon amino group of Lys has the following
                         substituent: [2-
                         (2-
                         )butan amido]ethoxy
ethoxy)acetamido]ethoxy
ethoxy)acetyl
SITE                    33
                        note = C-term amidation
source                  1..33
                        mol_type = protein
                        organism = synthetic construct
SEQUENCE: 253
RPEKPGEDAS PEELQRYYVS LRHYYNWLTR QAY                                   33

SEQ ID NO: 254          moltype = AA  length = 33
```

```
FEATURE              Location/Qualifiers
REGION               1..33
                     note = Amino acid sequence of formula I
REGION               1..33
                     note = Description of Artificial Sequence: Synthetic
                      polypeptide
VARIANT              2
                     note = Pro or 4Hyp
VARIANT              3
                     note = Ala or Glu
VARIANT              5
                     note = Ala, Ile, Pro, Thr, Val or 4Hyp
VARIANT              6
                     note = Glu, Gly, Gln or Pro
VARIANT              7
                     note = Ala or Glu
VARIANT              8
                     note = Ala, Asp, Glu or Pro
VARIANT              9
                     note = Ala, Gly, Ser, Thr or Val
VARIANT              10
                     note = Ala, Glu, Ser, Gln, Thr or Pro
VARIANT              11
                     note = Ala, Glu, Gly, Pro or 4Hyp
VARIANT              12
                     note = Ala, Glu or Ser
VARIANT              13
                     note = Ala, Glu or Ser
VARIANT              14
                     note = Ala, Ile, Leu, Thr or Val
VARIANT              15
                     note = Glu or Gln
VARIANT              16
                     note = Ala, Glu, Arg, Lys or Gln
VARIANT              18
                     note = Ala, Glu, Gln or Tyr
VARIANT              19
                     note = Ile, Ser, Thr or Val
VARIANT              20
                     note = Ala, Glu, Ser or Thr
VARIANT              21
                     note = Ala, Ile, Leu, Thr or Val
VARIANT              23
                     note = Ala, His or Lys
VARIANT              24
                     note = Gln or Tyr
VARIANT              25
                     note = His, Trp or Tyr
VARIANT              26
                     note = Asn, Trp or Tyr
VARIANT              27
                     note = Ala, His, Trp or Tyr
VARIANT              28
                     note = Ala, Ile, Leu or Thr
VARIANT              29
                     note = Gln, Leu or Thr
source               1..33
                     mol_type = protein
                     organism = synthetic construct
SEQUENCE: 254
AXXKXXXXXX XXXXXYXXX XRXXXXXXXR QRY                                  33

SEQ ID NO: 255       moltype = AA  length = 33
FEATURE              Location/Qualifiers
REGION               1..33
                     note = Description of Artificial Sequence: Synthetic
                      polypeptide
REGION               1..33
                     note = Amino acid sequence of formula II
VARIANT              2
                     note = Pro or 4Hyp
VARIANT              3
                     note = Ala or Glu
VARIANT              5
                     note = Ala, Pro or 4Hyp
VARIANT              6
                     note = Gln, Gly, Glu or Pro
VARIANT              7
                     note = Ala or Glu
```

```
VARIANT           8
                  note = Ala, Asp, Glu or Pro
VARIANT           9
                  note = Ala, Gly or Ser
VARIANT           10
                  note = Ala, Glu, Ser, Thr or Pro
VARIANT           11
                  note = Ala, Glu, Pro or 4Hyp
VARIANT           12
                  note = Ala, Glu or Ser
VARIANT           13
                  note = Ala, Glu or Ser
VARIANT           14
                  note = Ile, Leu, Thr or Val
VARIANT           15
                  note = Gln or Glu
VARIANT           16
                  note = Ala, Glu, Arg, Lys or Gln
VARIANT           18
                  note = Ala, Glu, Gln or Tyr
VARIANT           19
                  note = Ile, Ser, Thr or Val
VARIANT           20
                  note = Ala, Glu, Ser or Thr
VARIANT           21
                  note = Ala, Ile, Leu, Thr or Val
VARIANT           23
                  note = Ala, His or Lys
VARIANT           25
                  note = Trp or Tyr
VARIANT           26
                  note = Asn or Tyr
VARIANT           27
                  note = His, Trp or Tyr
VARIANT           28
                  note = Ala, Ile or Leu
VARIANT           29
                  note = Gln or Thr
source            1..33
                  mol_type = protein
                  organism = synthetic construct
SEQUENCE: 255
AXXKXXXXXX XXXXXXYXXX XRXYXXXXXR QRY                                33

SEQ ID NO: 256    moltype = AA  length = 33
FEATURE           Location/Qualifiers
REGION            1..33
                  note = Description of Artificial Sequence: Synthetic
                   polypeptide
REGION            1..33
                  note = Amino acid sequence of formula III
VARIANT           3
                  note = Ala or Glu
VARIANT           6
                  note = Glu or Gly
VARIANT           7
                  note = Ala or Glu
VARIANT           8
                  note = Ala, Asp, Glu or Pro
VARIANT           9
                  note = Ala or Ser
VARIANT           10
                  note = Ala, Glu, Ser, Thr or Pro
VARIANT           11
                  note = Ala, Glu or Pro
VARIANT           12
                  note = Ala or Glu
VARIANT           13
                  note = Ala or Glu
```

```
                        -continued

VARIANT                 14
                        note = Ile, Leu, Thr or Val
VARIANT                 15
                        note = Glu or Gln
VARIANT                 16
                        note = Ala, Glu, Arg, Lys or Gln
VARIANT                 18
                        note = Glu or Tyr
VARIANT                 20
                        note = Ala, Glu, Ser or Thr
source                  1..33
                        mol_type = protein
                        organism = synthetic construct
SEQUENCE: 256
APXKPXXXXX XXXXXXYXVX LRHYYNWLTR QRY                                    33

SEQ ID NO: 257          moltype = AA  length = 33
FEATURE                 Location/Qualifiers
REGION                  1..33
                        note = Description of Artificial Sequence: Synthetic
                         polypeptide
REGION                  1..33
                        note = Amino acid sequence of formula IV
VARIANT                 3
                        note = Ala or Glu
VARIANT                 7
                        note = Ala or Glu
VARIANT                 8
                        note = Ala, Asp or Glu
VARIANT                 10
                        note = Ala, Glu, Ser or Thr
VARIANT                 11
                        note = Ala, Pro or 4Hyp
VARIANT                 14
                        note = Ile or Leu
VARIANT                 16
                        note = Arg, Lys or Gln
VARIANT                 20
                        note = Ala, Glu or Ser
source                  1..33
                        mol_type = protein
                        organism = synthetic construct
SEQUENCE: 257
APXKPEXXAX XEEXQXYYVX LRHYYNWLTR QRY                                    33

SEQ ID NO: 258          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 258
RQRY                                                                     4

SEQ ID NO: 259          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 259
WLTRQRY                                                                  7
```

What is claimed is:
1. A PYY analogue comprising:
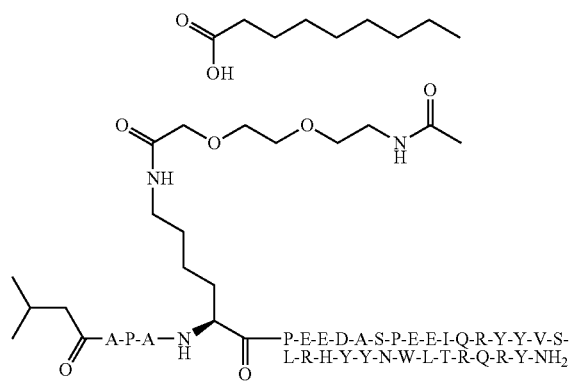
or a pharmaceutically acceptable salt thereof.
2. A PYY analogue, wherein the PYY analogue is:
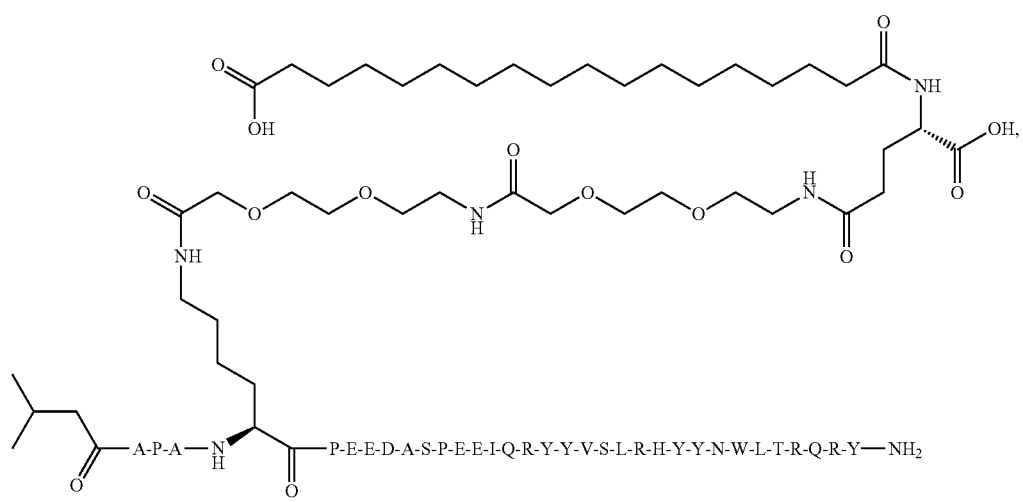
or a pharmaceutically acceptable salt thereof.

3. A PYY analogue comprising:
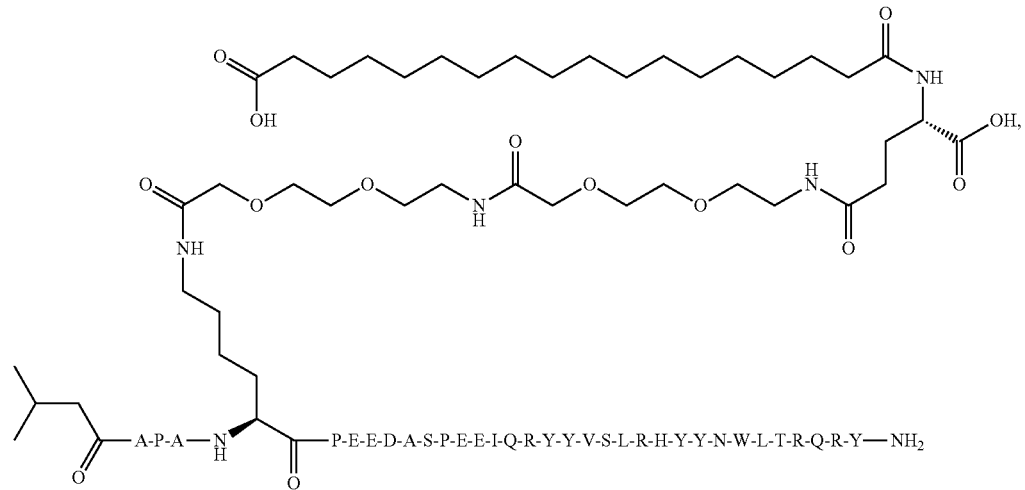
4. A PYY analogue, wherein the PYY analogue is:
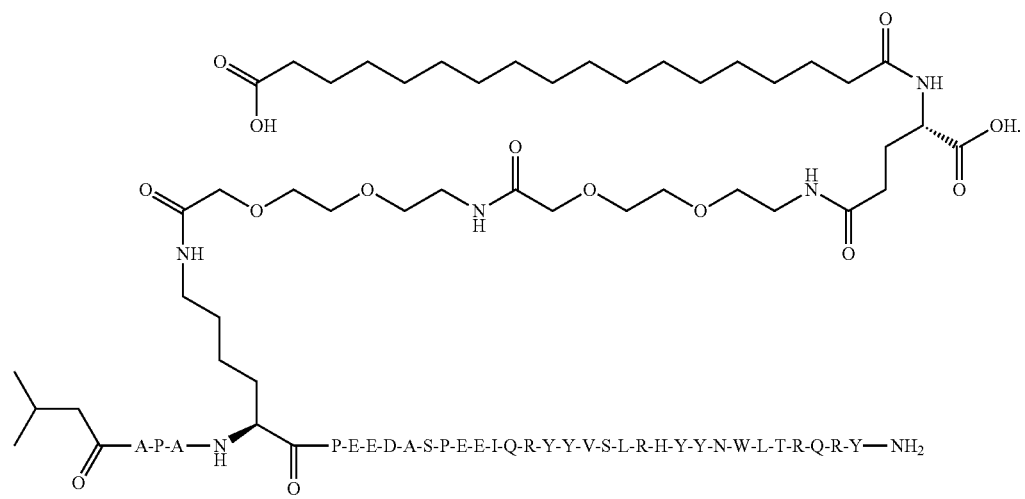

5. A PYY analogue comprising:

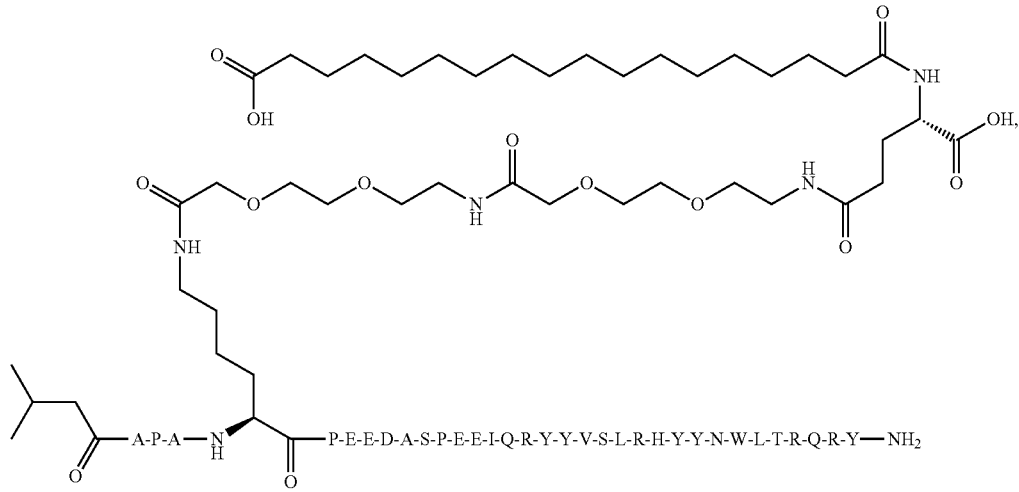

wherein the PYY analogue is in the form of a pharmaceutically acceptable salt.

6. A PYY analogue, wherein the PYY analogue is:

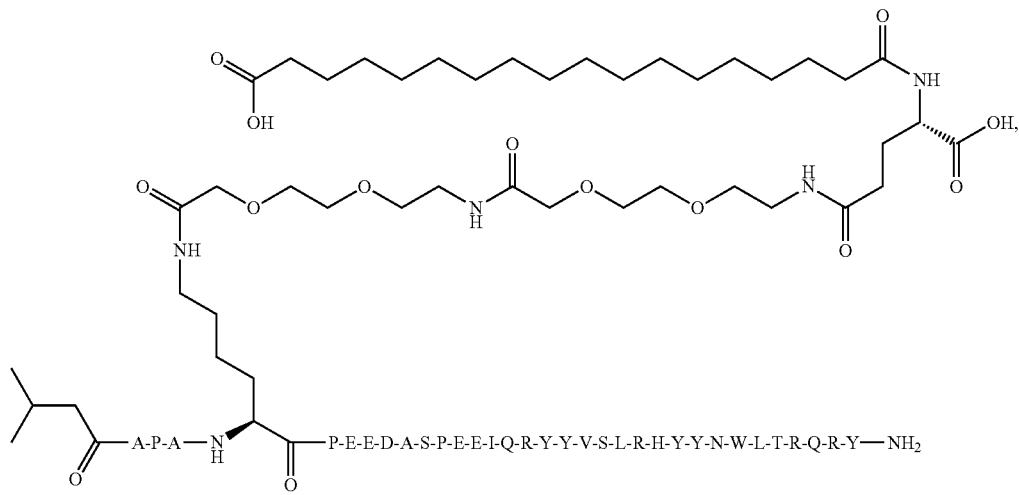

wherein the PYY analogue is in the form of a pharmaceutically acceptable salt.

7. A pharmaceutical composition comprising the PYY analogue or pharmaceutically acceptable salt thereof according to claim 1, and one or more pharmaceutically acceptable excipients.

8. A pharmaceutical composition comprising the PYY analogue or pharmaceutically acceptable salt thereof according to claim 2, and one or more pharmaceutically acceptable excipients.

9. A pharmaceutical composition comprising the PYY analogue according to claim 3, and one or more pharmaceutically acceptable excipients.

10. A pharmaceutical composition comprising the PYY analogue according to claim 4, and one or more pharmaceutically acceptable excipients.

11. A pharmaceutical composition comprising the salt form of the PYY analogue according to claim 5, and one or more pharmaceutically acceptable excipients.

12. A pharmaceutical composition comprising the salt form of the PYY analogue according to claim 6, and one or more pharmaceutically acceptable excipients.

* * * * *

UNITED STATES PATENT AND TRADEMARK OFFICE
CERTIFICATE OF CORRECTION

PATENT NO. : 12,054,525 B2
APPLICATION NO. : 18/068641
DATED : August 6, 2024
INVENTOR(S) : Peter Wilhelm Haebel et al.

Page 1 of 1

It is certified that error appears in the above-identified patent and that said Letters Patent is hereby corrected as shown below:

In the Claims

At Column 279, Lines 1-36, the compound structure in the claim is represented incorrectly. Please replace Claim 1, as represented below:

1. A PYY analogue comprising:

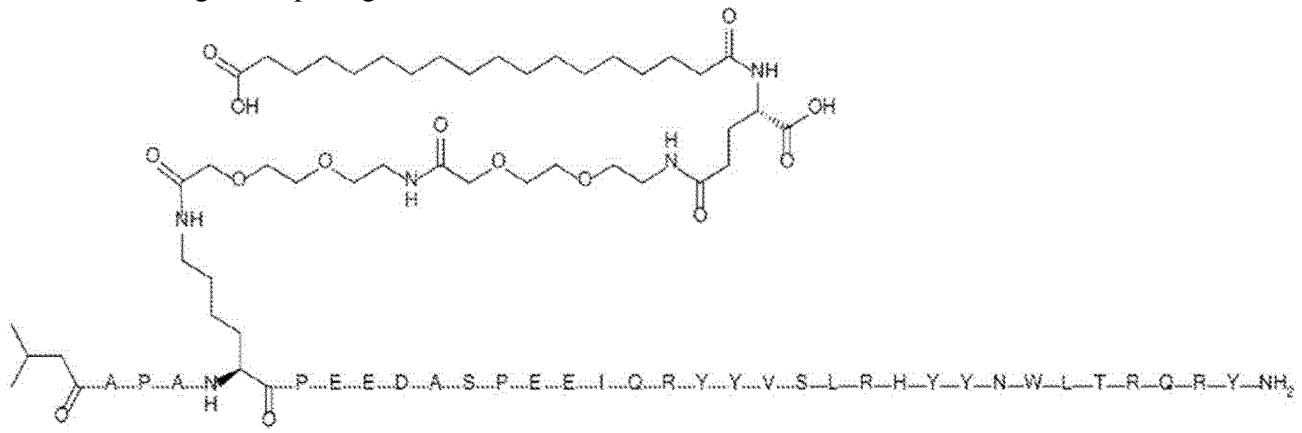

or a pharmaceutically acceptable salt thereof.

Signed and Sealed this
Twenty-ninth Day of April, 2025

Coke Morgan Stewart
*Acting Director of the United States Patent and Trademark Office*